(12) United States Patent
Graff et al.

(10) Patent No.: US 10,325,951 B2
(45) Date of Patent: *Jun. 18, 2019

(54) METHODS AND APPLICATIONS OF NON-PLANAR IMAGING ARRAYS

(71) Applicant: MC10, Inc., Lexington, MA (US)

(72) Inventors: Bassel de Graff, San Juan (TT); Gilman Callsen, Charlottesville, VA (US); William J. Arora, Bellevue, WA (US); Roozbeh Ghaffari, Cambridge, MA (US)

(73) Assignee: MC10, INC., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/620,181

(22) Filed: Jun. 12, 2017

(65) Prior Publication Data

US 2018/0190704 A1    Jul. 5, 2018

Related U.S. Application Data

(63) Continuation of application No. 14/812,197, filed on Jul. 29, 2015, now Pat. No. 9,704,908, which is a
(Continued)

(51) Int. Cl.
*H01L 27/146* (2006.01)
*A61B 1/04* (2006.01)
(Continued)

(52) U.S. Cl.
CPC ......... *H01L 27/14636* (2013.01); *A61B 1/04* (2013.01); *H01L 27/14621* (2013.01); *H01L 27/14683* (2013.01); *H01L 27/14687* (2013.01); *A61B 5/01* (2013.01); *A61B 5/145* (2013.01); *A61B 2562/02* (2013.01);
(Continued)

(58) Field of Classification Search
CPC ......... H01L 27/14609; H01L 27/14621; H01L 27/14636; H01L 27/14683; H01L 27/14687
See application file for complete search history.

(56) References Cited

U.S. PATENT DOCUMENTS 3,207,694 A    9/1965  Gogek
3,716,861 A    2/1973  Root
(Continued)

FOREIGN PATENT DOCUMENTS

CN    202068986 U    12/2011
DE    10 2006 011 596 A1    9/2007
(Continued)

OTHER PUBLICATIONS

Carvalhal et al., "Electrochemical Detection in a Paper-Based Separation Device", Analytical Chemistry, vol. 82, No. 3, (1162-1165) (4 pages) (Jan. 7, 2010).
(Continued)

*Primary Examiner* — Seahvosh Nikmanesh
(74) *Attorney, Agent, or Firm* — Nixon Peabody LLP

(57) ABSTRACT

System, devices and methods are presented that provide an imaging array fabrication process method, comprising fabricating an array of semiconductor imaging elements, interconnecting the elements with stretchable interconnections, and transfer printing the array with a pre-strained elastomeric stamp to a secondary non-planar surface.

15 Claims, 59 Drawing Sheets

Related U.S. Application Data continuation of application No. 13/747,826, filed on Jan. 23, 2013, now Pat. No. 9,123,614, which is a continuation of application No. 12/686,076, filed on Jan. 12, 2010, now Pat. No. 8,372,726, and a continuation-in-part of application No. 12/636,071, filed on Dec. 11, 2009, now Pat. No. 8,886,334, which is a continuation-in-part of application No. 12/616,922, filed on Nov. 12, 2009, now Pat. No. 8,389,862, which is a continuation-in-part of application No. 12/575,008, filed on Oct. 7, 2009, now Pat. No. 9,289,132.

(60) Provisional application No. 61/144,149, filed on Jan. 12, 2009, provisional application No. 61/156,906, filed on Mar. 3, 2009, provisional application No. 61/121,541, filed on Dec. 11, 2008, provisional application No. 61/121,568, filed on Dec. 11, 2008, provisional application No. 61/140,169, filed on Dec. 23, 2008, provisional application No. 61/113,622, filed on Nov. 12, 2008, provisional application No. 61/103,361, filed on Oct. 7, 2008, provisional application No. 61/113,007, filed on Nov. 10, 2008.

(51) Int. Cl.
*A61B 5/145* (2006.01)
*A61B 5/01* (2006.01)

(52) U.S. Cl.
CPC ............... *A61B 2562/0204* (2013.01); *A61B 2562/0209* (2013.01); *A61B 2562/0233* (2013.01); *A61B 2562/0247* (2013.01); *A61B 2562/046* (2013.01); *A61B 2562/164* (2013.01); *H01L 27/14609* (2013.01); *H01L 2224/18* (2013.01); *H01L 2224/24* (2013.01); *H01L 2224/24137* (2013.01); *H01L 2224/82* (2013.01); *H01L 2924/3512* (2013.01)

(56) References Cited

U.S. PATENT DOCUMENTS

| | | |
|---|---|---|
| 3,805,427 A | 4/1974 | Epstein |
| 3,838,240 A | 9/1974 | Schelhorn |
| 3,892,905 A | 7/1975 | Albert |
| 4,136,162 A | 1/1979 | Fuchs |
| 4,278,474 A | 7/1981 | Blakeslee |
| 4,304,235 A | 12/1981 | Kaufman |
| 4,416,288 A | 11/1983 | Freeman |
| 4,658,153 A | 4/1987 | Brosh |
| 4,911,169 A | 3/1990 | Ferrari |
| 5,059,424 A | 10/1991 | Cartmell |
| 5,064,576 A | 11/1991 | Suto |
| 5,272,375 A | 12/1993 | Belopolsky |
| 5,306,917 A | 4/1994 | Black |
| 5,326,521 A | 7/1994 | East |
| 5,331,966 A | 7/1994 | Bennett |
| 5,360,987 A | 11/1994 | Shibib |
| 5,471,982 A | 5/1995 | Edwards |
| 5,454,270 A | 10/1995 | Brown |
| 5,491,651 A | 2/1996 | Janic |
| 5,567,975 A | 10/1996 | Walsh |
| 5,580,794 A | 12/1996 | Allen |
| 5,617,870 A | 4/1997 | Hastings |
| 5,811,790 A | 9/1998 | Endo |
| 5,817,008 A | 10/1998 | Rafert |
| 5,907,477 A | 5/1999 | Tuttle |
| 6,063,046 A | 5/2000 | Allum |
| 6,220,916 B1 | 4/2001 | Bart |
| 6,265,090 B1 | 7/2001 | Nishide |
| 6,270,872 B1 | 8/2001 | Cline |
| 6,282,960 B1 | 9/2001 | Samuels |
| 6,343,514 B1 | 2/2002 | Smith |
| 6,387,052 B1 | 5/2002 | Quinn |
| 6,410,971 B1 | 6/2002 | Otey |
| 6,421,016 B1 | 7/2002 | Phillips |
| 6,450,026 B1 | 9/2002 | Desarnaud |
| 6,455,931 B1 | 9/2002 | Hamilton |
| 6,567,158 B1 | 5/2003 | Falcial |
| 6,626,940 B2 | 9/2003 | Crowley |
| 6,628,987 B1 | 9/2003 | Hill |
| 6,641,860 B1 | 11/2003 | Kaiserman |
| 6,775,906 B1 | 8/2004 | Silverbrook |
| 6,784,844 B1 | 8/2004 | Boakes |
| 6,825,539 B2 | 11/2004 | Tai |
| 6,965,160 B2 | 11/2005 | Cobbley |
| 6,987,314 B1 | 1/2006 | Yoshida |
| 7,259,030 B2 | 8/2007 | Daniels |
| 7,265,298 B2 | 9/2007 | Maghribi |
| 7,302,751 B2 | 12/2007 | Hamburgen |
| 7,337,012 B2 | 2/2008 | Maghribi |
| 7,487,587 B2 | 2/2009 | Vanfleteren |
| 7,491,892 B2 | 2/2009 | Wagner |
| 7,521,292 B2 | 4/2009 | Rogers |
| 7,557,367 B2 | 7/2009 | Rogers |
| 7,618,260 B2 | 11/2009 | Daniel |
| 7,622,367 B1 | 11/2009 | Nuzzo |
| 7,727,228 B2 | 6/2010 | Abboud |
| 7,739,791 B2 | 6/2010 | Brandenburg |
| 7,759,167 B2 | 7/2010 | Vanfleteren |
| 7,815,095 B2 | 10/2010 | Fujisawa |
| 7,960,246 B2 | 6/2011 | Flamand |
| 7,982,296 B2 | 7/2011 | Nuzzo |
| 8,097,926 B2 | 1/2012 | De Graff |
| 8,198,621 B2 | 6/2012 | Rogers |
| 8,207,473 B2 | 6/2012 | Axisa |
| 8,217,381 B2 | 7/2012 | Rogers |
| 8,332,053 B1 | 12/2012 | Patterson |
| 8,372,726 B2 | 2/2013 | De Graff |
| 8,389,862 B2 | 3/2013 | Arora |
| 8,431,828 B2 | 4/2013 | Vanfleteren |
| 8,440,546 B2 | 5/2013 | Nuzzo |
| 8,536,667 B2 | 9/2013 | de Graff |
| 8,552,299 B2 | 10/2013 | Rogers |
| 8,609,471 B2 | 12/2013 | Xu |
| 8,618,656 B2 | 12/2013 | Oh |
| 8,664,699 B2 | 3/2014 | Nuzzo |
| 8,679,888 B2 | 3/2014 | Rogers |
| 8,729,524 B2 | 5/2014 | Rogers |
| 8,754,396 B2 | 6/2014 | Rogers |
| 8,865,489 B2 | 10/2014 | Rogers |
| 8,886,334 B2 | 11/2014 | Ghaffari |
| 8,905,772 B2 | 12/2014 | Rogers |
| 9,012,784 B2 | 4/2015 | Arora |
| 9,082,025 B2 | 7/2015 | Fastert |
| 9,105,555 B2 | 8/2015 | Rogers |
| 9,105,782 B2 | 8/2015 | Rogers |
| 9,107,592 B2 | 8/2015 | Litt |
| 9,119,533 B2 | 9/2015 | Ghaffari |
| 9,123,614 B2 | 9/2015 | Graff |
| 9,159,635 B2 | 10/2015 | Elolampi |
| 9,168,094 B2 | 10/2015 | Lee |
| 9,171,794 B2 | 10/2015 | Rafferty |
| 9,186,060 B2 | 11/2015 | De Graff |
| 9,226,402 B2 | 12/2015 | Hsu |
| 9,247,637 B2 | 1/2016 | Hsu |
| 9,289,132 B2 | 3/2016 | Ghaffari |
| 9,295,842 B2 | 3/2016 | Ghaffari |
| 9,320,907 B2 | 4/2016 | Bogie |
| 9,324,733 B2 | 4/2016 | Rogers |
| 9,372,123 B2 | 6/2016 | Li |
| 9,408,305 B2 | 8/2016 | Hsu |
| 9,420,953 B2 | 8/2016 | Litt |
| 9,450,043 B2 | 9/2016 | Nuzzo |
| 9,515,025 B2 | 12/2016 | Rogers |
| 9,516,758 B2 | 12/2016 | Arora |
| 9,545,216 B2 | 1/2017 | D'Angelo |
| 9,545,285 B2 | 1/2017 | Ghaffari |
| 9,554,850 B2 | 1/2017 | Lee |
| 9,579,040 B2 | 2/2017 | Rafferty |
| 9,583,428 B2 | 2/2017 | Rafferty |

(56) References Cited

U.S. PATENT DOCUMENTS

| | | |
|---|---|---|
| D781,270 S | 3/2017 | Li |
| 9,622,680 B2 | 4/2017 | Ghaffari |
| 9,629,586 B2 | 4/2017 | Ghaffari |
| 9,647,171 B2 | 5/2017 | Rogers |
| 9,655,560 B2 | 5/2017 | Ghaffari |
| 9,662,069 B2 | 5/2017 | De Graff |
| 9,702,839 B2 | 7/2017 | Ghaffari |
| 9,704,908 B2 | 7/2017 | De Graff |
| 9,706,647 B2 | 7/2017 | Hsu |
| 9,723,122 B2 | 8/2017 | Ghaffari |
| 9,723,711 B2 | 8/2017 | Elolampi |
| 9,750,421 B2 | 9/2017 | Ghaffari |
| 9,757,050 B2 | 9/2017 | Ghaffari |
| 9,761,444 B2 | 9/2017 | Nuzzo |
| 9,768,086 B2 | 9/2017 | Nuzzo |
| 9,801,557 B2 | 10/2017 | Ghaffari |
| 9,844,145 B2 | 10/2017 | Hsu |
| 9,810,623 B2 | 11/2017 | Ghaffari |
| 9,833,190 B2 | 12/2017 | Ghaffari |
| 9,839,367 B2 | 12/2017 | Litt |
| 9,846,829 B2 | 12/2017 | Fastert |
| 9,894,757 B2 | 2/2018 | Arora |
| 9,899,330 B2 | 2/2018 | Dalal |
| 2001/0012918 A1 | 8/2001 | Swanson |
| 2001/0021867 A1 | 9/2001 | Kordis |
| 2002/0000813 A1 | 1/2002 | Hirono |
| 2002/0026127 A1 | 2/2002 | Balbierz |
| 2002/0077534 A1 | 6/2002 | Durousseau |
| 2002/0079572 A1 | 6/2002 | Khan |
| 2002/0082515 A1 | 6/2002 | Campbell |
| 2002/0094701 A1 | 7/2002 | Biegelsen |
| 2002/0107436 A1 | 8/2002 | Barton |
| 2002/0113739 A1 | 8/2002 | Howard |
| 2002/0118464 A1 | 8/2002 | Nishioka et al. |
| 2002/0128700 A1 | 9/2002 | Cross, Jr. |
| 2002/0145467 A1 | 10/2002 | Minch |
| 2002/0151934 A1 | 10/2002 | Levine |
| 2002/0158330 A1 | 10/2002 | Moon |
| 2002/0173730 A1 | 11/2002 | Pottgen |
| 2002/0193724 A1 | 12/2002 | Stebbings |
| 2003/0017848 A1 | 1/2003 | Engstrom |
| 2003/0045025 A1 | 3/2003 | Coyle |
| 2003/0097165 A1 | 5/2003 | Krulevitch |
| 2003/0120271 A1 | 6/2003 | Burnside |
| 2003/0162507 A1 | 8/2003 | Vatt |
| 2003/0214408 A1 | 11/2003 | Grajales |
| 2003/0236455 A1 | 12/2003 | Swanson |
| 2004/0006264 A1 | 1/2004 | Mojarradi |
| 2004/0085469 A1 | 5/2004 | Johnson |
| 2004/0092806 A1 | 5/2004 | Sagon |
| 2004/0106334 A1 | 6/2004 | Suzuki |
| 2004/0118831 A1 | 6/2004 | Martin |
| 2004/0135094 A1 | 7/2004 | Niigaki |
| 2004/0138558 A1 | 7/2004 | Dunki-Jacobs |
| 2004/0149921 A1 | 8/2004 | Smyk |
| 2004/0178466 A1 | 9/2004 | Merrill |
| 2004/0192082 A1 | 9/2004 | Wagner |
| 2004/0201134 A1 | 10/2004 | Kawai |
| 2004/0203486 A1 | 10/2004 | Shepherd |
| 2004/0221370 A1 | 11/2004 | Hannula |
| 2004/0238819 A1 | 12/2004 | Maghribi |
| 2004/0243204 A1 | 12/2004 | Maghribi |
| 2005/0021103 A1 | 1/2005 | DiLorenzo |
| 2005/0029680 A1 | 2/2005 | Jung |
| 2005/0030408 A1 | 2/2005 | Ito |
| 2005/0067293 A1 | 3/2005 | Naito |
| 2005/0070778 A1 | 3/2005 | Lackey |
| 2005/0096513 A1 | 5/2005 | Ozguz |
| 2005/0113744 A1 | 5/2005 | Donoghue |
| 2005/0139683 A1 | 6/2005 | Yi |
| 2005/0171524 A1 | 8/2005 | Stern |
| 2005/0203366 A1 | 9/2005 | Donoghue |
| 2005/0204811 A1 | 9/2005 | Neff |
| 2005/0248312 A1 | 11/2005 | Cao |
| 2005/0261617 A1 | 11/2005 | Hall |
| 2005/0258050 A1 | 12/2005 | Bruce |
| 2005/0285262 A1 | 12/2005 | Knapp |
| 2006/0003709 A1 | 1/2006 | Wood |
| 2006/0038182 A1 | 2/2006 | Rogers |
| 2006/0071349 A1 | 4/2006 | Tokushige |
| 2006/0084394 A1 | 4/2006 | Engstrom |
| 2006/0106321 A1 | 5/2006 | Lewinsky |
| 2006/0122298 A1 | 6/2006 | Menon |
| 2006/0128346 A1 | 6/2006 | Yasui |
| 2006/0154398 A1 | 7/2006 | Qing |
| 2006/0160560 A1 | 7/2006 | Josenhans |
| 2006/0235314 A1 | 10/2006 | Migliuolo |
| 2006/0248946 A1 | 11/2006 | Howell |
| 2006/0257945 A1 | 11/2006 | Masters |
| 2006/0264767 A1 | 11/2006 | Shennib |
| 2006/0270135 A1 | 11/2006 | Chrysler |
| 2006/0276702 A1 | 12/2006 | McGinnis |
| 2006/0286785 A1 | 12/2006 | Rogers |
| 2007/0027514 A1 | 2/2007 | Gerber |
| 2007/0031283 A1 | 2/2007 | Davis |
| 2007/0069894 A1 | 3/2007 | Lee |
| 2007/0108389 A1 | 5/2007 | Makela |
| 2007/0113399 A1 | 5/2007 | Kumar |
| 2007/0123756 A1 | 5/2007 | Kitajima |
| 2007/0139451 A1 | 6/2007 | Somasiri |
| 2007/0151358 A1 | 7/2007 | Chien |
| 2007/0179373 A1 | 8/2007 | Pronovost |
| 2007/0190880 A1 | 8/2007 | Dubrow |
| 2007/0270672 A1 | 11/2007 | Hayter |
| 2007/0270674 A1 | 11/2007 | Kane |
| 2008/0036097 A1 | 2/2008 | Ito |
| 2008/0046080 A1 | 2/2008 | Vanden Bulcke |
| 2008/0074383 A1 | 3/2008 | Dean |
| 2008/0091089 A1 | 4/2008 | Guillory |
| 2008/0096620 A1 | 4/2008 | Lee |
| 2008/0139894 A1 | 6/2008 | Szydlo-Moore |
| 2008/0157235 A1 | 7/2008 | Rogers |
| 2008/0185534 A1 | 8/2008 | Simon |
| 2008/0188912 A1 | 8/2008 | Stone |
| 2008/0193749 A1 | 8/2008 | Thompson |
| 2008/0200973 A1 | 8/2008 | Mallozzi |
| 2008/0204021 A1 | 8/2008 | Leussler |
| 2008/0211087 A1 | 9/2008 | Mueller-Hipper |
| 2008/0237840 A1 | 10/2008 | Alcoe |
| 2008/0259576 A1 | 10/2008 | Johnson |
| 2008/0262381 A1 | 10/2008 | Kolen |
| 2008/0275327 A1 | 11/2008 | Faarbaek |
| 2008/0287167 A1 | 11/2008 | Caine |
| 2008/0297350 A1 | 12/2008 | Iwasa |
| 2008/0309807 A1 | 12/2008 | Kinoshita |
| 2008/0313552 A1 | 12/2008 | Buehler |
| 2009/0000377 A1 | 1/2009 | Shipps |
| 2009/0001550 A1 | 1/2009 | Li |
| 2009/0015560 A1 | 1/2009 | Robinson |
| 2009/0017884 A1 | 1/2009 | Rotschild |
| 2009/0048556 A1 | 2/2009 | Durand |
| 2009/0076363 A1 | 3/2009 | Bly |
| 2009/0088750 A1 | 4/2009 | Hushka |
| 2009/0107704 A1 | 4/2009 | Vanfleteren |
| 2009/0154736 A1 | 6/2009 | Lee |
| 2009/0184254 A1 | 7/2009 | Miura |
| 2009/0204168 A1 | 8/2009 | Kallmeyer |
| 2009/0215385 A1 | 8/2009 | Waters |
| 2009/0225751 A1 | 9/2009 | Koenck |
| 2009/0261828 A1 | 10/2009 | Nordmeyer-Massner |
| 2009/0273909 A1 | 11/2009 | Shin |
| 2009/0283891 A1 | 11/2009 | Dekker |
| 2009/0291508 A1 | 11/2009 | Babu |
| 2009/0294803 A1 | 12/2009 | Nuzzo |
| 2009/0317639 A1 | 12/2009 | Axisa |
| 2009/0322480 A1 | 12/2009 | Benedict |
| 2010/0002402 A1 | 1/2010 | Rogers |
| 2010/0030167 A1 | 2/2010 | Thirstrup |
| 2010/0036211 A1 | 2/2010 | La Rue |
| 2010/0059863 A1 | 3/2010 | Rogers |
| 2010/0072577 A1 | 3/2010 | Nuzzo |
| 2010/0073669 A1 | 3/2010 | Colvin |
| 2010/0087782 A1 | 4/2010 | Ghaffari |
| 2010/0090781 A1 | 4/2010 | Yamamoto |

(56) References Cited

U.S. PATENT DOCUMENTS

| | | |
|---|---|---|
| 2010/0090824 A1 | 4/2010 | Rowell |
| 2010/0116526 A1 | 5/2010 | Arora |
| 2010/0117660 A1 | 5/2010 | Douglas |
| 2010/0178722 A1 | 7/2010 | De Graff |
| 2010/0245011 A1 | 9/2010 | Chatzopoulos |
| 2010/0254092 A1 | 10/2010 | Dong |
| 2010/0271191 A1 | 10/2010 | De Graff |
| 2010/0298895 A1 | 11/2010 | Ghaffari |
| 2010/0317132 A1 | 12/2010 | Rogers |
| 2010/0321161 A1 | 12/2010 | Isabell |
| 2010/0327387 A1 | 12/2010 | Kasai |
| 2011/0011179 A1 | 1/2011 | Gustafsson |
| 2011/0019370 A1 | 1/2011 | Koh |
| 2011/0034760 A1 | 2/2011 | Brynelsen |
| 2011/0034912 A1 | 2/2011 | De Graff |
| 2011/0051384 A1 | 3/2011 | Kriechbaum |
| 2011/0054583 A1 | 3/2011 | Litt |
| 2011/0071603 A1 | 3/2011 | Moore |
| 2011/0098583 A1 | 4/2011 | Pandia |
| 2011/0101789 A1 | 5/2011 | Salter |
| 2011/0121822 A1 | 5/2011 | Parsche |
| 2011/0136436 A1 | 6/2011 | Hoyt |
| 2011/0140856 A1 | 6/2011 | Downie |
| 2011/0140897 A1 | 6/2011 | Purks |
| 2011/0175735 A1 | 7/2011 | Forster |
| 2011/0184320 A1 | 7/2011 | Shipps |
| 2011/0185611 A1 | 8/2011 | Adams |
| 2011/0213559 A1 | 9/2011 | Pollack |
| 2011/0215931 A1 | 9/2011 | Callsen |
| 2011/0218756 A1 | 9/2011 | Callsen |
| 2011/0218757 A1 | 9/2011 | Callsen |
| 2011/0220890 A1 | 9/2011 | Nuzzo |
| 2011/0222375 A1 | 9/2011 | Tsubata |
| 2011/0263950 A1 | 10/2011 | Larson |
| 2011/0270049 A1 | 11/2011 | Katra |
| 2011/0277813 A1 | 11/2011 | Rogers |
| 2011/0284268 A1 | 11/2011 | Palaniswamy |
| 2011/0306851 A1 | 12/2011 | Wang |
| 2011/0317737 A1 | 12/2011 | Klewer |
| 2012/0016258 A1 | 1/2012 | Webster |
| 2012/0051005 A1 | 3/2012 | Vanfleteren |
| 2012/0052268 A1 | 3/2012 | Axisa |
| 2012/0065937 A1 | 3/2012 | De Graff |
| 2012/0068848 A1 | 3/2012 | Campbell |
| 2012/0074546 A1 | 3/2012 | Chong |
| 2012/0087216 A1 | 4/2012 | Keung |
| 2012/0091594 A1 | 4/2012 | Landesberger |
| 2012/0092178 A1 | 4/2012 | Callsen |
| 2012/0092222 A1 | 4/2012 | Kato |
| 2012/0101413 A1 | 4/2012 | Beetel |
| 2012/0101538 A1 | 4/2012 | Ballakur |
| 2012/0108012 A1 | 5/2012 | Yasuda |
| 2012/0126418 A1 | 5/2012 | Feng |
| 2012/0150072 A1 | 6/2012 | Revol-Cavalier |
| 2012/0150074 A1 | 6/2012 | Yanev |
| 2012/0157804 A1 | 6/2012 | Rogers |
| 2012/0165759 A1 | 6/2012 | Rogers |
| 2012/0172697 A1 | 7/2012 | Urman |
| 2012/0178367 A1 | 7/2012 | Matsumoto |
| 2012/0179075 A1 | 7/2012 | Perry |
| 2012/0206097 A1 | 8/2012 | Scar |
| 2012/0215127 A1 | 8/2012 | Shikida |
| 2012/0220835 A1 | 8/2012 | Chung |
| 2012/0226130 A1 | 9/2012 | De Graff |
| 2012/0244848 A1 | 9/2012 | Ghaffari |
| 2012/0245444 A1 | 9/2012 | Otis |
| 2012/0256308 A1 | 10/2012 | Helin |
| 2012/0256492 A1 | 10/2012 | Song |
| 2012/0314382 A1 | 12/2012 | Wesselmann |
| 2012/0316455 A1 | 12/2012 | Rahman |
| 2012/0327608 A1 | 12/2012 | Rogers |
| 2013/0035751 A1 | 2/2013 | Shalev |
| 2013/0041235 A1 | 2/2013 | Rogers |
| 2013/0044215 A1 | 2/2013 | Rothkopf |
| 2013/0066365 A1 | 3/2013 | Belson |
| 2013/0079693 A1 | 3/2013 | Ranky |
| 2013/0085552 A1 | 4/2013 | Mandel |
| 2013/0099358 A1 | 4/2013 | Elolampi |
| 2013/0100618 A1 | 4/2013 | Rogers |
| 2013/0116520 A1 | 5/2013 | Roham |
| 2013/0118255 A1 | 5/2013 | Callsen |
| 2013/0123587 A1 | 5/2013 | Sarrafzadeh |
| 2013/0131660 A1 | 5/2013 | Monson |
| 2013/0147063 A1 | 6/2013 | Park |
| 2013/0150693 A1 | 6/2013 | D'Angelo |
| 2013/0185003 A1 | 7/2013 | Carbeck |
| 2013/0192356 A1 | 8/2013 | De Graff |
| 2013/0197319 A1 | 8/2013 | Monty |
| 2013/0200268 A1 | 8/2013 | Rafferty |
| 2013/0211761 A1 | 8/2013 | Brandsma |
| 2013/0214300 A1 | 8/2013 | Lerman |
| 2013/0215467 A1 | 8/2013 | Fein |
| 2013/0225965 A1 | 8/2013 | Ghaffari |
| 2013/0237150 A1 | 9/2013 | Royston |
| 2013/0245387 A1 | 9/2013 | Patel |
| 2013/0245388 A1 | 9/2013 | Rafferty |
| 2013/0253285 A1 | 9/2013 | Bly |
| 2013/0261415 A1 | 10/2013 | Ashe |
| 2013/0261464 A1 | 10/2013 | Singh |
| 2013/0274562 A1 | 10/2013 | Ghaffari |
| 2013/0285836 A1 | 10/2013 | Proud |
| 2013/0313713 A1 | 11/2013 | Arora |
| 2013/0316442 A1 | 11/2013 | Meurville |
| 2013/0316487 A1 | 11/2013 | De Graff |
| 2013/0316645 A1 | 11/2013 | Li |
| 2013/0320503 A1 | 12/2013 | Nuzzo |
| 2013/0321373 A1 | 12/2013 | Yoshizumi |
| 2013/0325357 A1 | 12/2013 | Walerow |
| 2013/0328219 A1 | 12/2013 | Chau |
| 2013/0331914 A1 | 12/2013 | Lee |
| 2014/0001058 A1 | 1/2014 | Ghaffari |
| 2014/0002242 A1 | 1/2014 | Fenkanyn |
| 2014/0012160 A1 | 1/2014 | Ghaffari |
| 2014/0012242 A1 | 1/2014 | Lee |
| 2014/0022746 A1 | 1/2014 | Hsu |
| 2014/0039290 A1 | 2/2014 | De Graff |
| 2014/0097944 A1 | 4/2014 | Fastert |
| 2014/0110859 A1 | 4/2014 | Rafferty |
| 2014/0125458 A1 | 5/2014 | Bachman |
| 2014/0140020 A1 | 5/2014 | Rogers |
| 2014/0188426 A1 | 7/2014 | Fastert |
| 2014/0191236 A1 | 7/2014 | Nuzzo |
| 2014/0206976 A1 | 7/2014 | Thompson |
| 2014/0216524 A1 | 8/2014 | Rogers |
| 2014/0240932 A1 | 8/2014 | Hsu |
| 2014/0249520 A1 | 9/2014 | Ghaffari |
| 2014/0275835 A1 | 9/2014 | Lamego |
| 2014/0303452 A1 | 10/2014 | Ghaffari |
| 2014/0303520 A1 | 10/2014 | Telfort |
| 2014/0303680 A1 | 10/2014 | Donnelly |
| 2014/0308930 A1 | 10/2014 | Tran |
| 2014/0340857 A1 | 11/2014 | Hsu |
| 2014/0342174 A1 | 11/2014 | Tominaga |
| 2014/0350883 A1 | 11/2014 | Carter |
| 2014/0371547 A1 | 12/2014 | Gartenberg |
| 2014/0371823 A1 | 12/2014 | Mashiach |
| 2014/0374872 A1 | 12/2014 | Rogers |
| 2014/0375465 A1 | 12/2014 | Fenuccio |
| 2015/0001462 A1 | 1/2015 | Rogers |
| 2015/0019135 A1 | 1/2015 | Kacyvenski |
| 2015/0025394 A1 | 1/2015 | Hong |
| 2015/0035680 A1 | 2/2015 | Li |
| 2015/0035743 A1 | 2/2015 | Rosener |
| 2015/0069617 A1 | 3/2015 | Arora |
| 2015/0099976 A1 | 4/2015 | Ghaffari |
| 2015/0100135 A1 | 4/2015 | Ives |
| 2015/0126878 A1 | 5/2015 | An |
| 2015/0150505 A1 | 6/2015 | Kaskoun |
| 2015/0164377 A1 | 6/2015 | Nathan |
| 2015/0178806 A1 | 6/2015 | Nuzzo |
| 2015/0181700 A1 | 6/2015 | Rogers |
| 2015/0194817 A1 | 7/2015 | Lee |
| 2015/0237711 A1 | 8/2015 | Rogers |
| 2015/0241288 A1 | 8/2015 | Keen |

(56) References Cited

U.S. PATENT DOCUMENTS

| | | |
|---|---|---|
| 2015/0248833 A1 | 9/2015 | Arne |
| 2015/0260713 A1 | 9/2015 | Ghaffari |
| 2015/0272652 A1 | 10/2015 | Ghaffari |
| 2015/0286913 A1 | 10/2015 | Fastert |
| 2015/0320472 A1 | 11/2015 | Ghaffari |
| 2015/0335254 A1 | 11/2015 | Fastert |
| 2015/0342036 A1 | 11/2015 | Elolampi |
| 2015/0371511 A1 | 12/2015 | Miller |
| 2015/0373487 A1 | 12/2015 | Miller |
| 2016/0006123 A1 | 1/2016 | Li |
| 2016/0015962 A1 | 1/2016 | Shokoueinejad Maragheh |
| 2016/0027834 A1 | 1/2016 | de Graff |
| 2016/0037478 A1 | 2/2016 | Skaaksrud |
| 2016/0045162 A1 | 2/2016 | de Graff |
| 2016/0058380 A1 | 3/2016 | Lee |
| 2016/0066854 A1 | 3/2016 | Mei |
| 2016/0081192 A1 | 3/2016 | Hsu |
| 2016/0086909 A1 | 3/2016 | Garlock |
| 2016/0095652 A1 | 4/2016 | Lee |
| 2016/0099214 A1 | 4/2016 | Dalal |
| 2016/0099227 A1 | 4/2016 | Dalal |
| 2016/0111353 A1 | 4/2016 | Rafferty |
| 2016/0135740 A1 | 5/2016 | Ghaffari |
| 2016/0178251 A1 | 6/2016 | Johnson |
| 2016/0213262 A1 | 7/2016 | Ghaffari |
| 2016/0213424 A1 | 7/2016 | Ghaffari |
| 2016/0228640 A1 | 8/2016 | Pindado |
| 2016/0232807 A1 | 8/2016 | Ghaffari |
| 2016/0240061 A1 | 8/2016 | Li |
| 2016/0249174 A1 | 8/2016 | Patel |
| 2016/0256070 A1 | 9/2016 | Murphy |
| 2016/0271290 A1 | 9/2016 | Humayun |
| 2016/0284544 A1 | 9/2016 | Nuzzo |
| 2016/0287177 A1 | 10/2016 | Huppert |
| 2016/0293794 A1 | 10/2016 | Nuzzo |
| 2016/0309594 A1 | 10/2016 | Hsu |
| 2016/0322283 A1 | 11/2016 | McMahon |
| 2016/0338646 A1 | 11/2016 | Lee |
| 2016/0361015 A1 | 12/2016 | Wang |
| 2016/0371957 A1 | 12/2016 | Ghaffari |
| 2016/0381789 A1 | 12/2016 | Rogers |
| 2017/0019988 A1 | 1/2017 | McGrane |
| 2017/0049397 A1 | 2/2017 | Sun |
| 2017/0071491 A1 | 3/2017 | Litt |
| 2017/0079588 A1 | 3/2017 | Ghaffari |
| 2017/0079589 A1 | 3/2017 | Ghaffari |
| 2017/0083312 A1 | 3/2017 | Pindado |
| 2017/0086747 A1 | 3/2017 | Ghaffari |
| 2017/0086748 A1 | 3/2017 | Ghaffari |
| 2017/0086749 A1 | 3/2017 | Ghaffari |
| 2017/0095670 A1 | 4/2017 | Ghaffari |
| 2017/0095732 A1 | 4/2017 | Ghaffari |
| 2017/0105795 A1 | 4/2017 | Lee |
| 2017/0110417 A1 | 4/2017 | Arora |
| 2017/0164865 A1 | 6/2017 | Rafferty |
| 2017/0164866 A1 | 6/2017 | Rafferty |
| 2017/0181659 A1 | 6/2017 | Rafferty |
| 2017/0186727 A1 | 6/2017 | Dalal |
| 2017/0188942 A1 | 7/2017 | Ghaffari |
| 2017/0200670 A1 | 7/2017 | Rafferty |
| 2017/0200679 A1 | 7/2017 | Rogers |
| 2017/0200707 A1 | 7/2017 | Rogers |
| 2017/0223846 A1 | 8/2017 | Elolampi |
| 2017/0244285 A1 | 8/2017 | Raj |
| 2017/0244543 A1 | 8/2017 | Raj |
| 2017/0296114 A1 | 10/2017 | Ghaffari |
| 2017/0331524 A1 | 11/2017 | Aranyosi |
| 2017/0340236 A1 | 11/2017 | Ghaffari |
| 2018/0076336 A1 | 3/2018 | de Graff |

FOREIGN PATENT DOCUMENTS

| | | |
|---|---|---|
| DE | 10 2007 046 886 A1 | 4/2009 |
| DE | 10 2008 044 902 A1 | 3/2010 |
| EP | 0526855 A1 | 2/1993 |
| EP | 0585670 A2 | 3/1994 |
| EP | 0779059 A1 | 6/1997 |
| EP | 0952542 A1 | 10/1999 |
| EP | 1808124 A2 | 7/2007 |
| EP | 2259062 A2 | 12/2010 |
| EP | 2498196 A2 | 9/2012 |
| EP | 2541995 A1 | 1/2013 |
| JP | H 04-290489 A | 10/1992 |
| JP | 05-087511 A | 4/1993 |
| JP | 2001-156278 A | 6/2001 |
| JP | 2002-190971 | 7/2002 |
| JP | 2005-052212 A | 3/2005 |
| JP | 2005-278133 | 10/2005 |
| JP | 2008-312050 | 12/2008 |
| JP | 2009-170173 A | 7/2009 |
| WO | WO 1999/038211 A | 7/1999 |
| WO | WO 2002/047162 A2 | 6/2002 |
| WO | WO 2003/021679 A2 | 3/2003 |
| WO | WO 2004/084720 A2 | 10/2004 |
| WO | WO 2005/083546 A1 | 9/2005 |
| WO | WO 2005/122285 A2 | 12/2005 |
| WO | WO 2006/013573 A2 | 2/2006 |
| WO | WO 2007/003019 A2 | 1/2007 |
| WO | WO 2007/024983 A2 | 3/2007 |
| WO | WO 2007/116344 A1 | 10/2007 |
| WO | WO 2007/136726 A2 | 11/2007 |
| WO | WO 2008/030960 A2 | 3/2008 |
| WO | WO 2008/055212 A2 | 5/2008 |
| WO | WO 2009/036260 A1 | 3/2009 |
| WO | WO 2009/111641 A1 | 9/2009 |
| WO | WO 2009/114689 A1 | 9/2009 |
| WO | WO 2010/036807 A1 | 4/2010 |
| WO | WO 2010/042653 A1 | 4/2010 |
| WO | WO 2010/042957 A2 | 4/2010 |
| WO | WO 2010/046883 A1 | 4/2010 |
| WO | WO 2010/056857 A2 | 5/2010 |
| WO | WO 2010/081137 A2 | 7/2010 |
| WO | WO 2010/082993 A2 | 7/2010 |
| WO | WO 2010/102310 A2 | 9/2010 |
| WO | WO 2010/132552 A1 | 11/2010 |
| WO | WO 2011/003181 A1 | 1/2011 |
| WO | WO 2011/041727 A1 | 4/2011 |
| WO | WO 2011/084450 A1 | 7/2011 |
| WO | WO 2011/084709 A2 | 7/2011 |
| WO | WO 2011/124898 A1 | 10/2011 |
| WO | WO 2011/127331 A2 | 10/2011 |
| WO | WO 2012/094264 A2 | 7/2012 |
| WO | WO 2012/125494 A2 | 9/2012 |
| WO | WO 2012/166686 A2 | 12/2012 |
| WO | WO 2013/010171 A1 | 1/2013 |
| WO | WO 2013/022853 A1 | 2/2013 |
| WO | WO 2013/033724 A1 | 3/2013 |
| WO | WO 2013/034987 A3 | 3/2013 |
| WO | WO 2013/049716 A1 | 4/2013 |
| WO | WO 2013/052919 A2 | 4/2013 |
| WO | WO 2013/144738 A2 | 10/2013 |
| WO | WO 2013/144866 A1 | 10/2013 |
| WO | WO 2013/170032 A2 | 11/2013 |
| WO | WO 2014/007871 A1 | 1/2014 |
| WO | WO 2014/058473 A1 | 4/2014 |
| WO | WO 2014/059032 A1 | 4/2014 |
| WO | WO 2014/106041 A1 | 7/2014 |
| WO | WO 2014/110176 A1 | 7/2014 |
| WO | WO 2014/124044 A1 | 8/2014 |
| WO | WO 2014/124049 A2 | 8/2014 |
| WO | WO 2014/130928 A2 | 8/2014 |
| WO | WO 2014/130931 A1 | 8/2014 |
| WO | WO 2014/186467 A2 | 11/2014 |
| WO | WO 2014/197443 A1 | 12/2014 |
| WO | WO 2014/205434 A2 | 12/2014 |
| WO | WO 2015/021039 A1 | 2/2015 |
| WO | WO 2015/054312 A1 | 4/2015 |
| WO | WO 2015/077559 A1 | 5/2015 |
| WO | WO 2015/080991 A1 | 6/2015 |
| WO | WO 2015/102951 A2 | 7/2015 |
| WO | WO 2015/103483 A1 | 7/2015 |
| WO | WO 2015/103580 A2 | 7/2015 |
| WO | WO 2015/127458 A1 | 8/2015 |
| WO | WO 2015/134588 A1 | 9/2015 |

(56) References Cited

FOREIGN PATENT DOCUMENTS

| WO | WO 2015/138712 A1 | 9/2015 |
|---|---|---|
| WO | WO 2015/145471 A1 | 10/2015 |
| WO | WO 2016/010983 A1 | 1/2016 |
| WO | WO 2016/048888 A1 | 3/2016 |
| WO | WO 2016/054512 A1 | 4/2016 |
| WO | WO 2016/057318 A1 | 4/2016 |
| WO | WO 2016/081244 A1 | 5/2016 |
| WO | WO 2016/0127050 A1 | 8/2016 |
| WO | WO 2016/134306 A1 | 8/2016 |
| WO | WO 2016-140961 A1 | 9/2016 |
| WO | WO 2016/205385 A1 | 12/2016 |
| WO | WO 2017/015000 A1 | 1/2017 |
| WO | WO 2017/059215 A1 | 4/2017 |
| WO | WO 2017/062508 A1 | 4/2017 |
| WO | WO 2017/184705 A1 | 10/2017 |
| WO | WO 2018/013569 A1 | 1/2018 |
| WO | WO 2018/013656 A1 | 1/2018 |
| WO | WO 2018/057911 A1 | 3/2018 |

OTHER PUBLICATIONS

Demura et al., "Immobilization of Glucose Oxidase with *Bombyx Mori* Silk Fibroin by Only Stretching Treatment and its Application to Glucose Sensor," Biotechnology and Bioengineering, vol. 33, 598-603 (6 pages) (1989).

Ellerbee et al., "Quantifying Colorimetric Assays in Paper-Based Microfluidic Devices by Measuring the Transmission of Light through Paper," Analytical Chemistry, vol. 81, No. 20 8447-8452, (6 pages) (Oct. 15, 2009).

Halsted, "Ligature and Suture Material," Journal of the American Medical Association, vol. LX, No. 15, 1119-1126, (8 pages) (Apr. 12, 1913).

Kim et al., "Complementary Metal Oxide Silicon Integrated Circuits Incorporating Monolithically Integrated Stretchable Wavy Interconnects," Applied Physics Letters, vol. 93, 044102-044102.3 (3 pages) (Jul. 31, 2008).

Kim et al., "Dissolvable Films of Silk Fibroin for Ultrathin Conformal Bio-Integrated Electronics," Nature, 1-8 (8 pages) (Apr. 18, 2010).

Kim et al., "Materials and Noncoplanar Mesh Designs for Integrated Circuits with Linear Elastic Responses to Extreme Mechanical Deformations," PNAS, vol. 105, No. 48, 18675-18680 (6 pages) (Dec. 2, 2008).

Kim et al., "Stretchable and Foldable Silicon Integrated Circuits," Science, vol. 320, 507-511 (5 pages) (Apr. 25, 2008).

Kim et al., "Electrowetting on Paper for Electronic Paper Display," ACS Applied Materials & Interfaces, vol. 2, No. 11, (3318-3323) (6 pages) (Nov. 24, 2010).

Ko et al., "A Hemispherical Electronic Eye Camera Based on Compressible Silicon Optoelectronics," Nature, vol. 454, 748-753 (6 pages) (Aug. 7, 2008).

Lawrence et al., "Bioactive Silk Protein Biomaterial Systems for Optical Devices," Biomacromolecules, vol. 9, 1214-1220 (7 pages) (Nov. 4, 2008).

Meitl et al., "Transfer Printing by Kinetic Control of Adhesion to an Elastomeric Stamp," Nature, vol. 5, 33-38 (6 pages) (Jan. 2006).

Omenetto et al., "A New Route for Silk," Nature Photonics, vol. 2, 641-643 (3 pages) (Nov. 2008).

Omenetto et al., "New Opportunities for an Ancient Material," Science, vol. 329, 528-531 (5 pages) (Jul. 30, 2010).

Siegel et al., "Foldable Printed Circuit Boards on Paper Substrates," Advanced Functional Materials, vol. 20, No. 1, 28-35, (8 pages) (Jan. 8, 2010).

Tsukada et al., "Structural Changes of Silk Fibroin Membranes Induced by Immersion in Methanol Aqueous Solutions," Journal of Polymer Science, vol. 32, 961-968 (8 pages) (1994).

Wang et al., "Controlled Release From Multilayer Silk Biomaterial Coatings to Modulate Vascular Cell Responses" Biomaterials, 29, 894-903 (10 pages) (Nov. 28, 2008).

Wikipedia, "Ball bonding" article [online]. Cited in PCT/US2015/051210 search report dated Mar. 1, 2016 with the following information "Jun. 15, 2011 [retrieved on Nov. 15, 2015}. Retrieved 12-18, 29 from the Internet: <URL: https://web.archive.org/web/20110615221003/hltp://en.wikipedia.org/wiki/Ball_bonding>., entire document, especially para 1, 4, 5, 6," 2 pages, last page says ("last modified on May 11, 2011").

Bossuyt et al., "Stretchable Electronics Technology for Large Area Applications: Fabrication and Mechanical Characterizations", vol. 3, pp. 229-235 (7 pages) (Feb. 2013).

Jones et al., "Stretchable Interconnects for Elastic Electronic Surfaces". vol. 93, pp. 1459-1467 (9 pages) (Aug. 2005).

Lin et al., "Design and Fabrication of Large-Area, Redundant, Stretchable Interconnect Meshes Using Excimer Laser Photoablation and In Situ Masking", (10 pages) (Aug. 2010).

Kim et al., "A Biaxial Stretchable Interconnect With Liquid-Alloy-Covered Joints on Elastomeric Substrate", vol. 18, pp. 138-146 (9 pages) (Feb. 2009).

Kinkeldi et al., "Encapsulation for Flexible Electronic Devices", IEE Electron Device Letters, 32(12): 1743-5 (2011).

Hsu et al., "Epidermal electronics: Skin sweat patch", Microsystems, Packaging, Assembly and Circuits Technology Conference (IMPACT), 2012 7th International. IEEE, 2012.

Siegel et al.,"Foldable printed circuit boards on paper substrates", Advanced Functional Materials, 20:28-35 (2010).

Ellerbee et al.,"Quantifying colorimetric assays in paper-based microfluidic devices by measuring the transmission of light through paper", Anal. Chem.,81(20):8447-52 (2009).

Wehner et al.; "A Lightweight Soft Exosuit for Gait Assistance"; IEEE International Conference on Robotics and Automation (ICRA), May 6-10, 2013. Retrieved from https://micro.seas.harvard.edu/papers/Wehner_ICRA13.pdf (8 pages).

Cauwe et al., "Flexible and Stretchable Circuit Technologies for Space Applications," 5th Electronic Materials, Processes and Packaging for Space, May 20-22, 2014 (18 pages).

Hild, "Surface Energy of Plastics," Dec. 16, 2009. Retrieved from https://www.tstar.com/blog/bid/33845/surface-energy-of-plastics (3 pages).

Hodge et al., "A Microcolorimetric Method for the Determination of Chloride," Microchemical Journal, vol. 7, Issue 3, Sep. 30, 1963, pp. 326-330 (5 pages).

Bonifácio et al., "An improved flow system for chloride determination in natural waters exploiting solid-phase reactor and long pathlength spectrophotometry," Talanta, vol. 72, Issue 2, Apr. 30, 2007, pp. 663-667 (5 pages).

Meyer et al., "The Effect of Gelatin Cross-Linking on the Bioequivalence of Hard and Soft Gelatin Acetaminophen Capsules," Pharmaceutical Research, vol. 17, No. 8, Aug. 31, 2000, pp. 962-966 (5 pages).

Japanese Office Action dated Aug. 2, 2016, Japanese Patent Application No. 2011-545508, 4 pages.

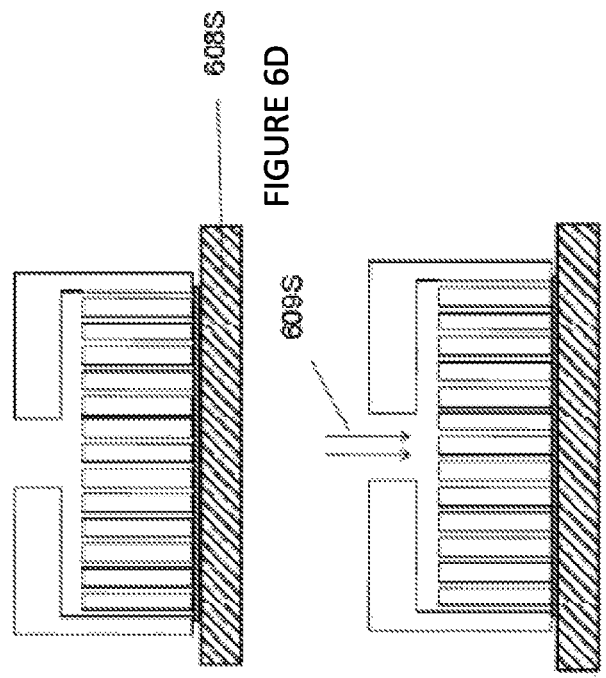
FIGURE 6A
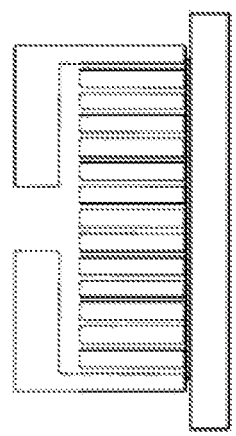
FIGURE 6B
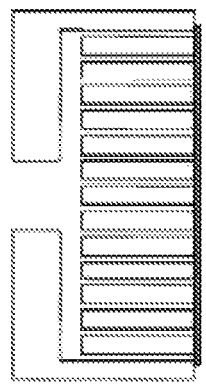
FIGURE 6C
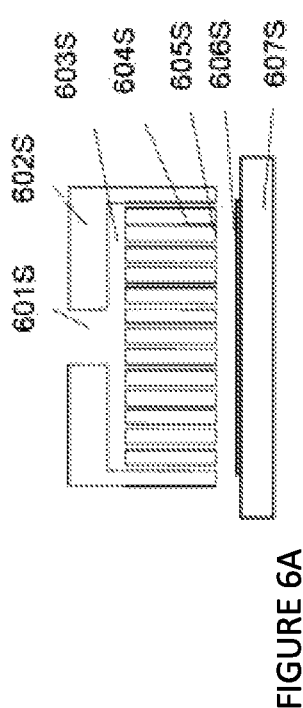
FIGURE 6D
FIGURE 6E
FIGURE 6F

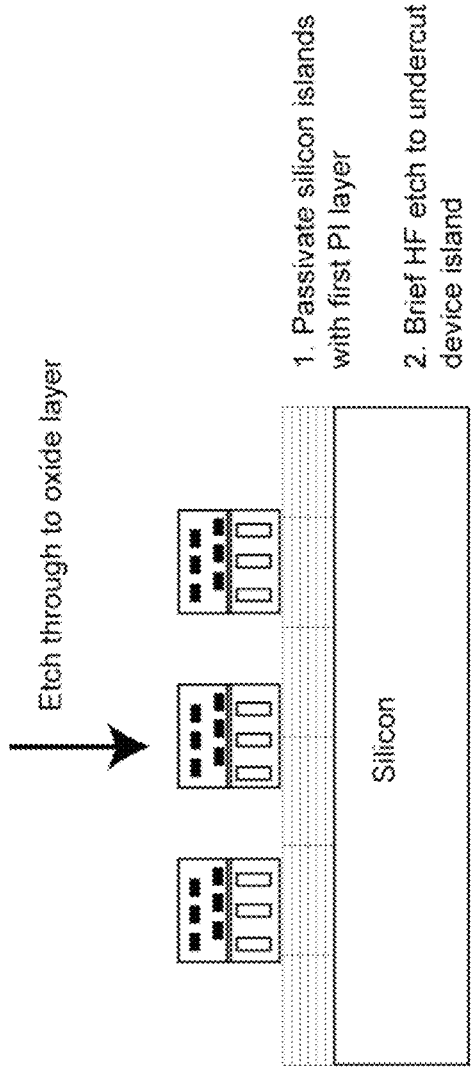
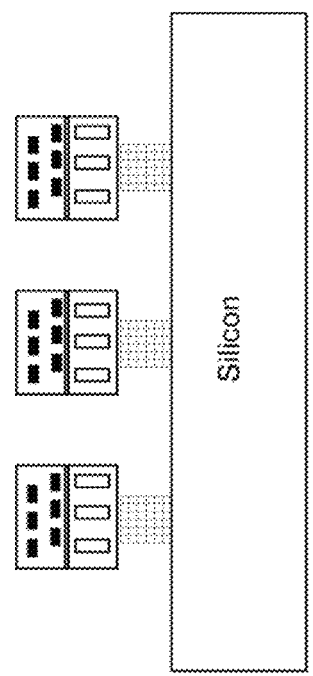
Figure 7C
Figure 7D

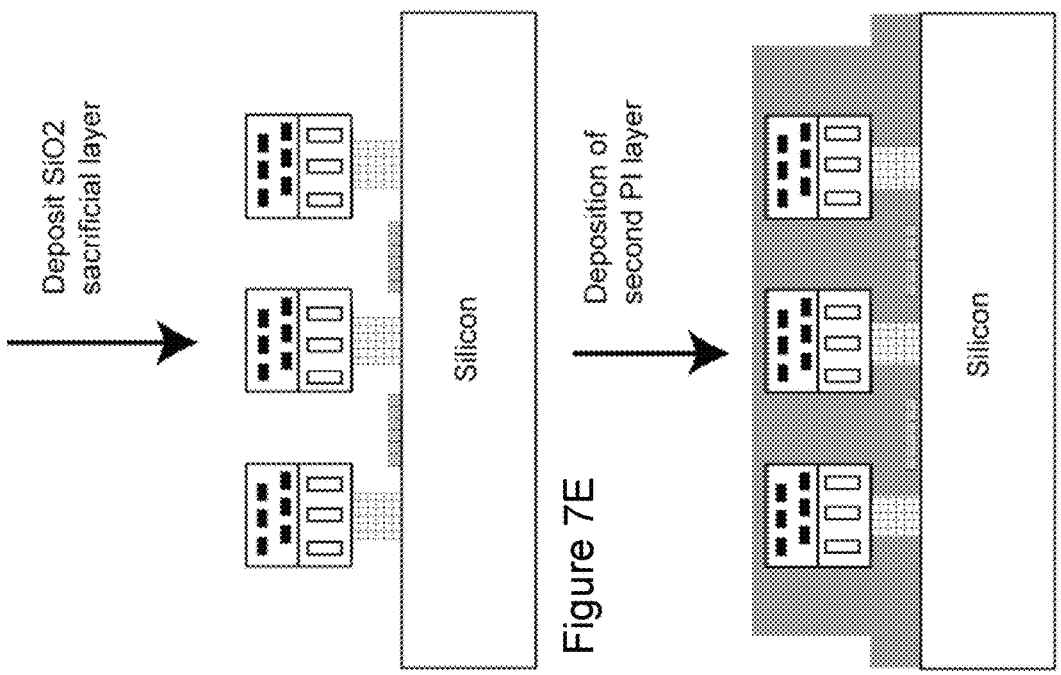

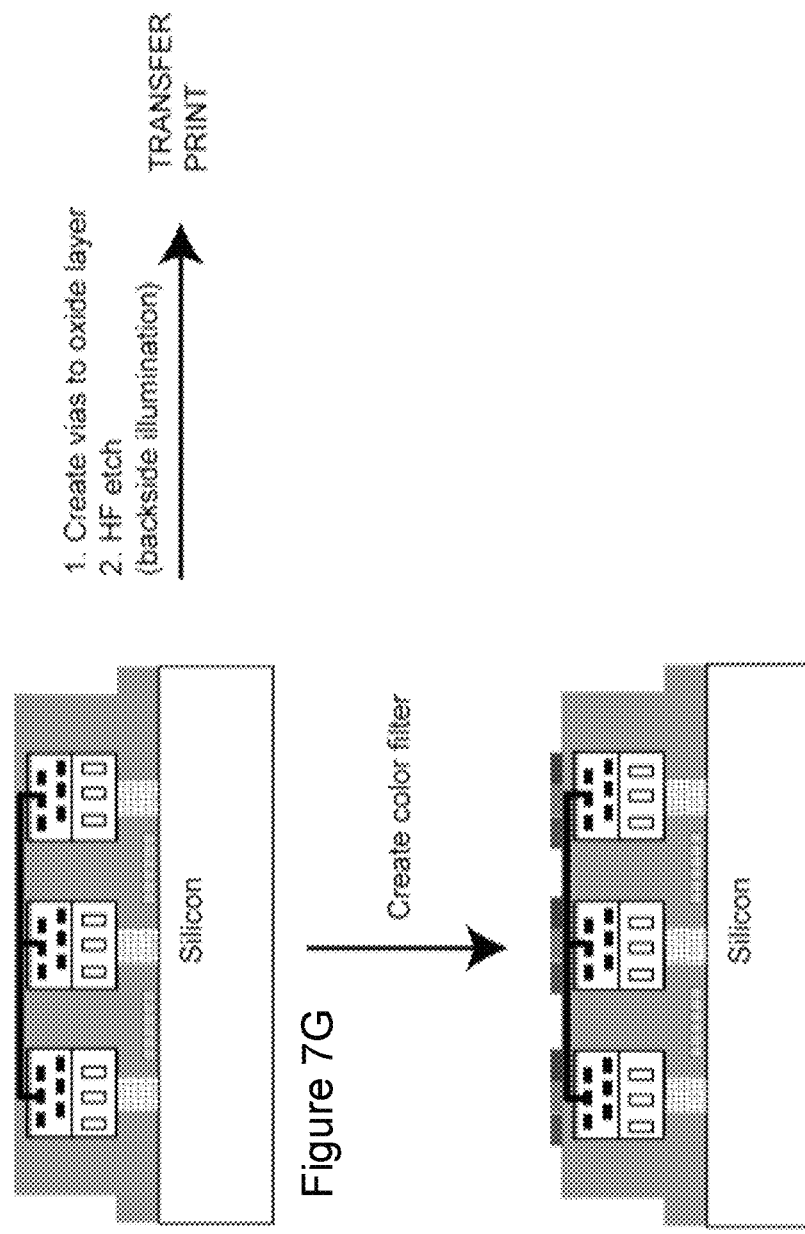

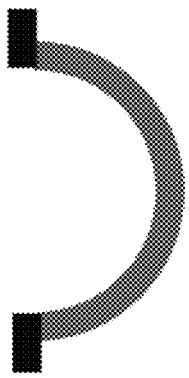
Figure 16A — Non-planar elastomeric stamp
Introduce strain by gentle heating or mechanical tool
Figure 16B — Planar, pre-strained elastomeric stamp

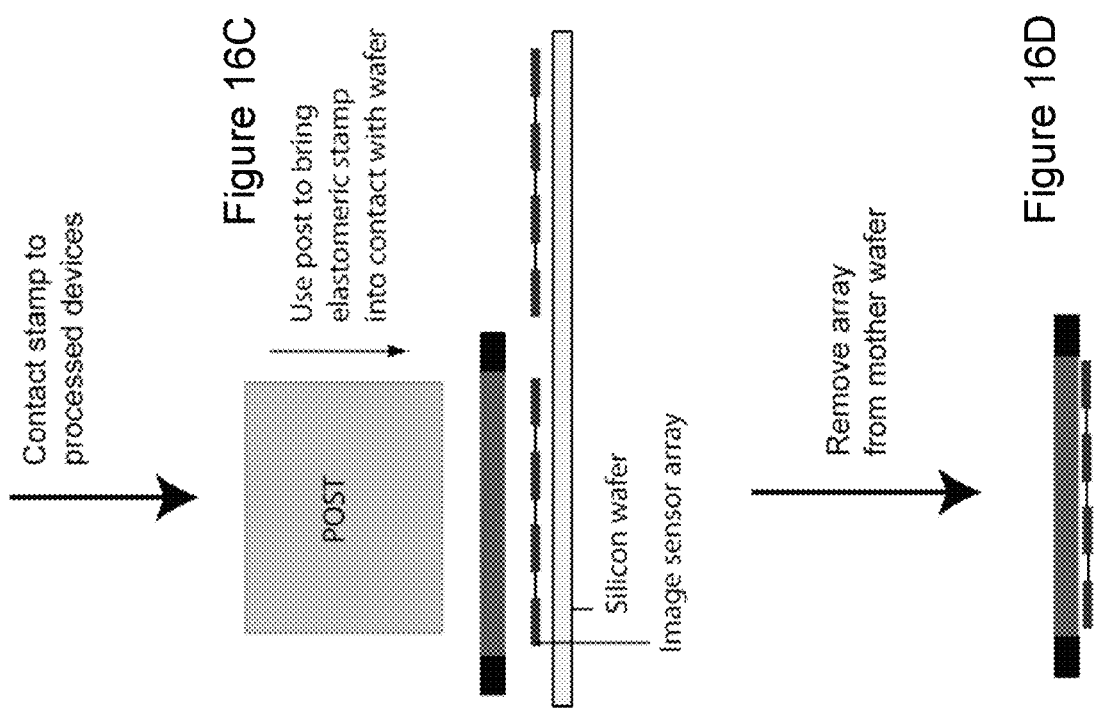

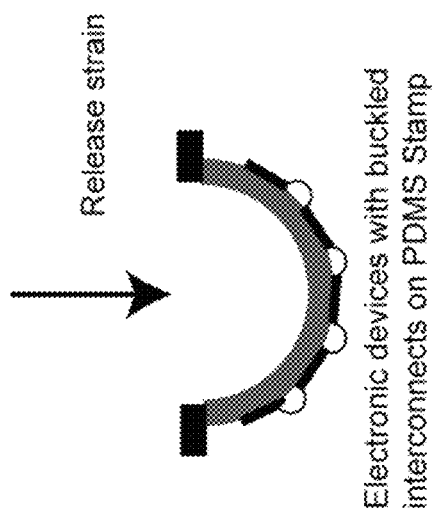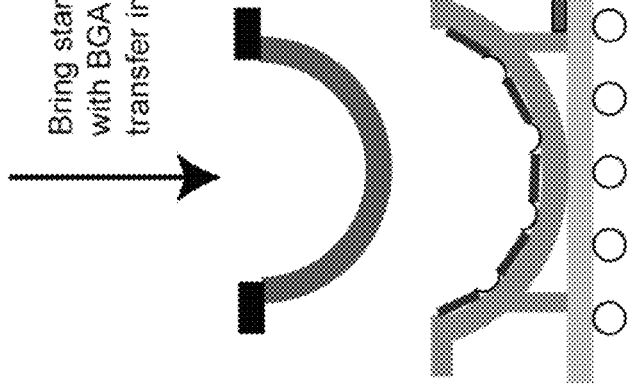

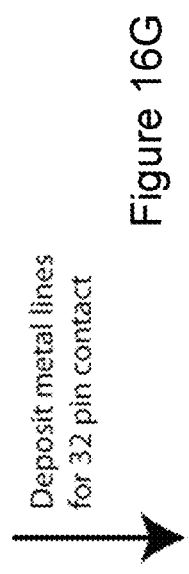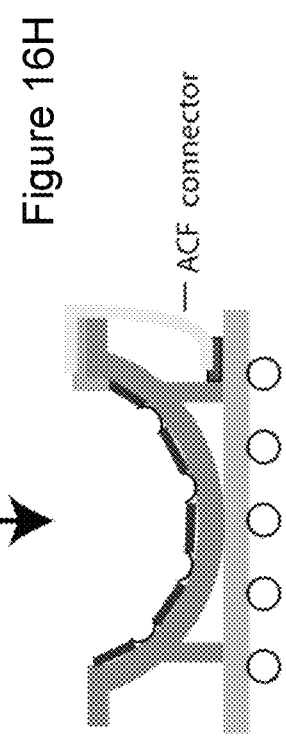

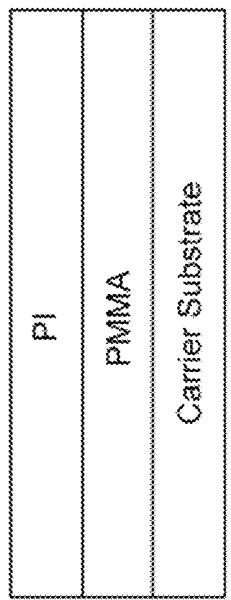
Figure 18A
Create color filter (pigmented photoresist)
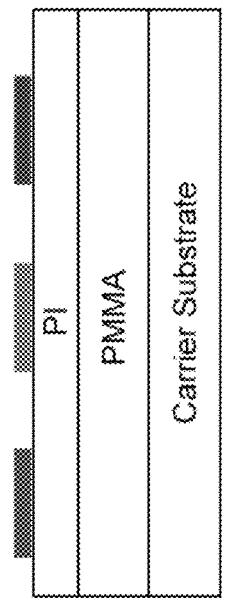
Figure 18B

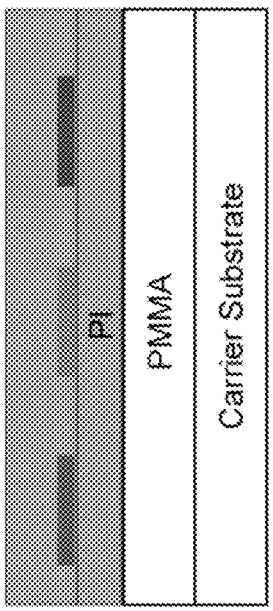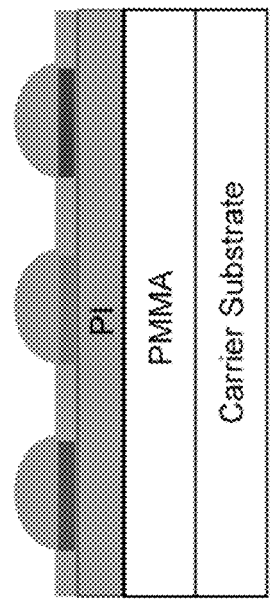

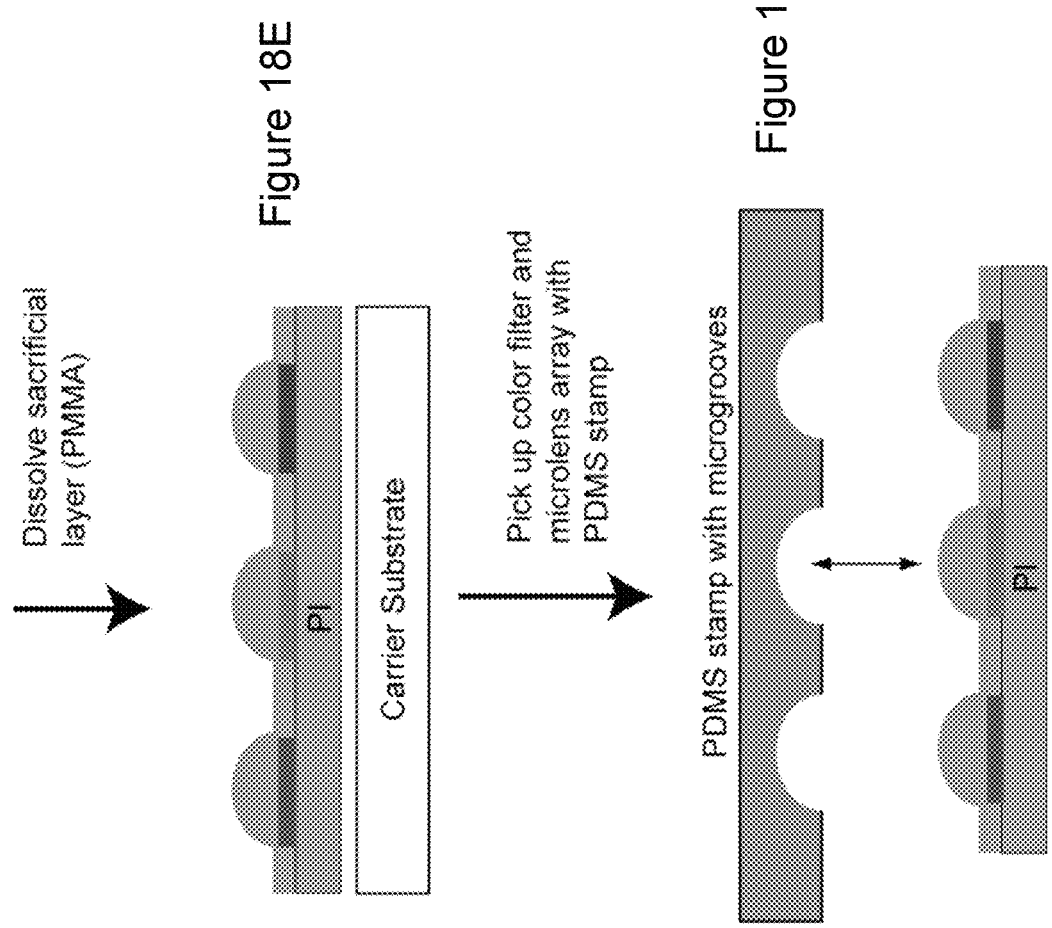

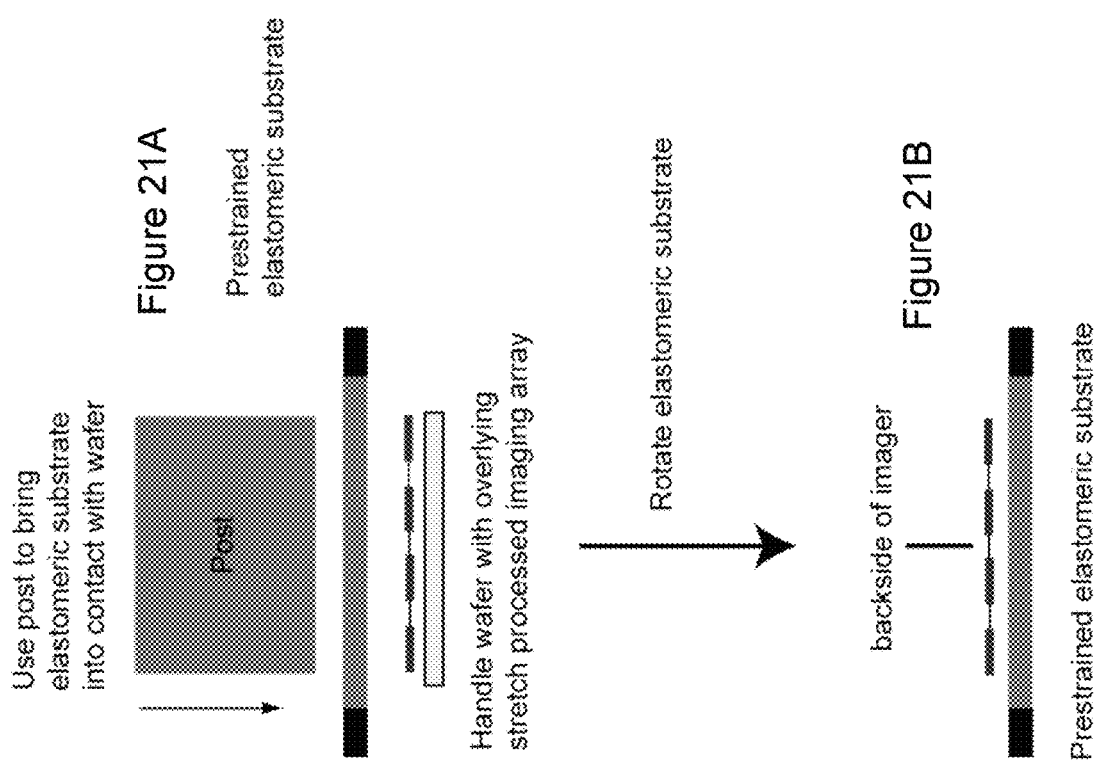

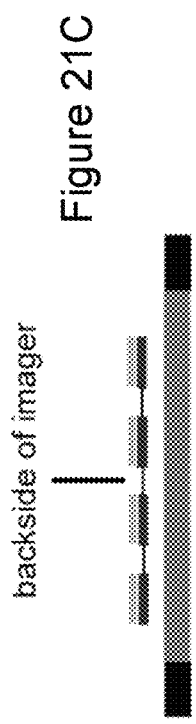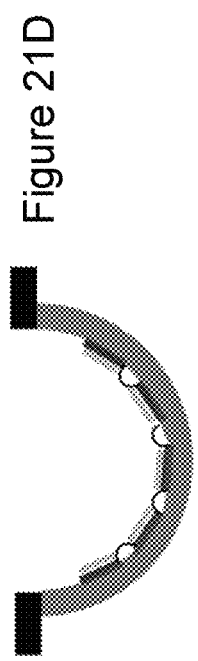

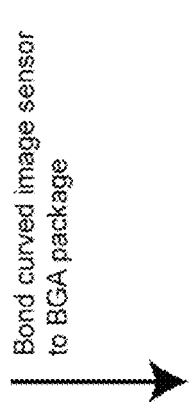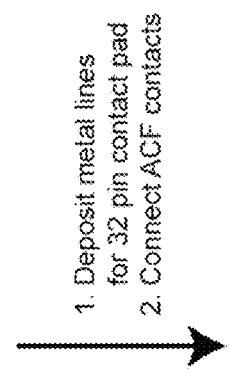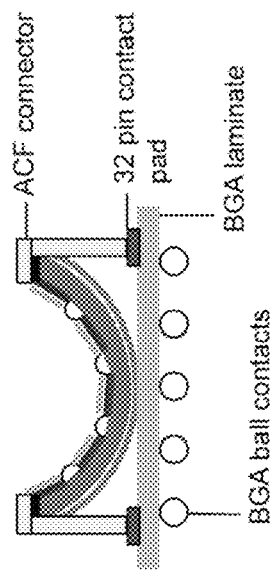

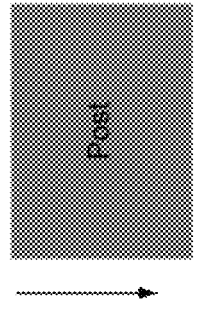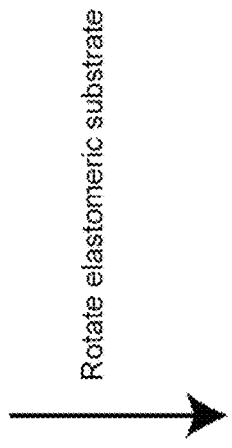
Figure 22A
Figure 22B

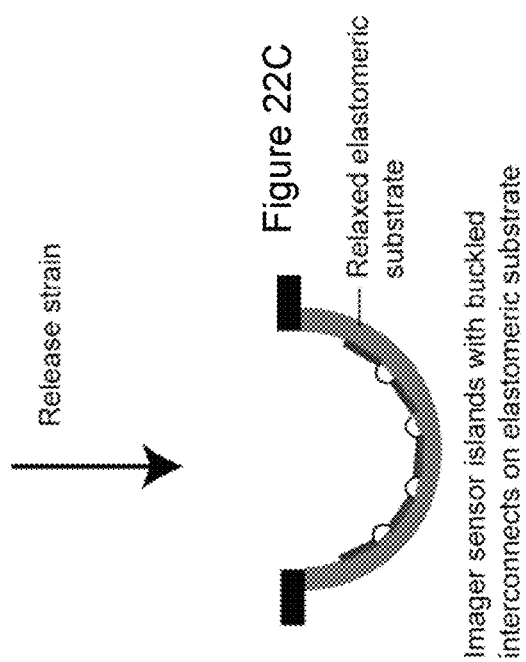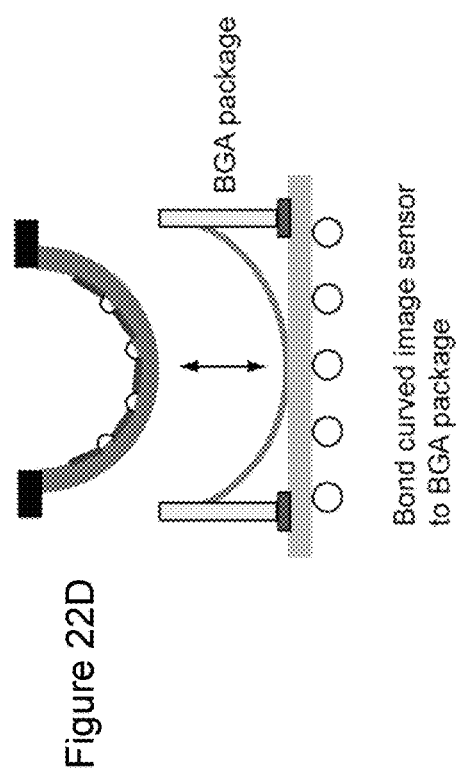

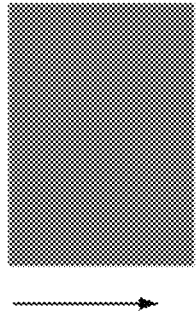
Figure 23A
Figure 23B

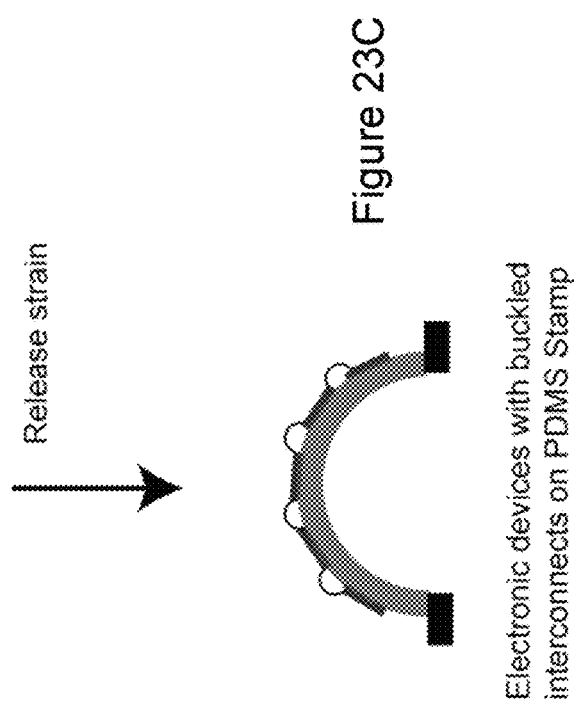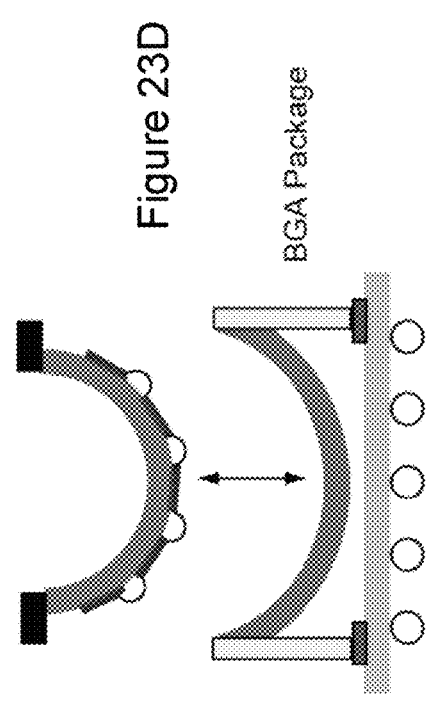

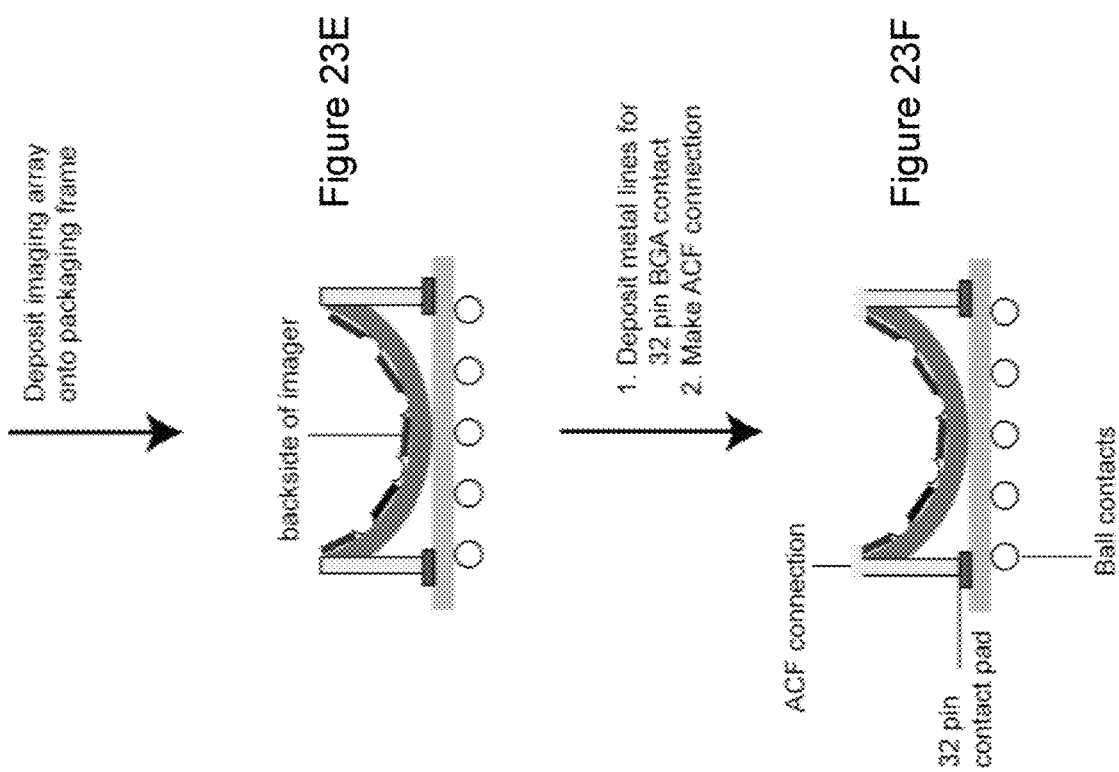

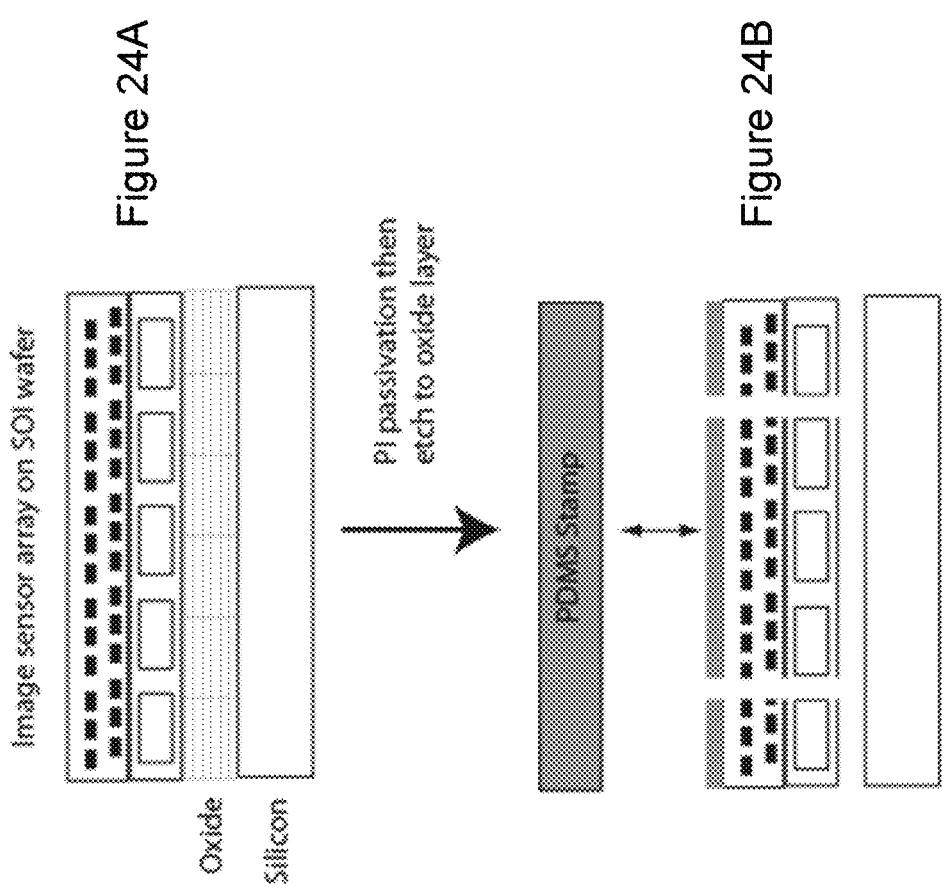

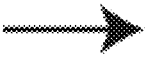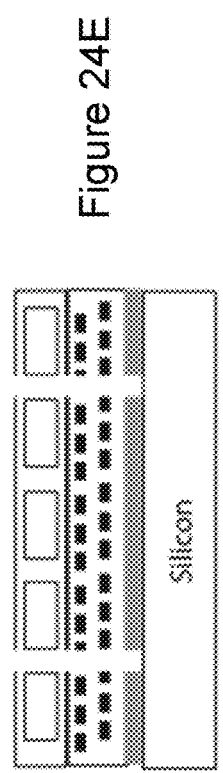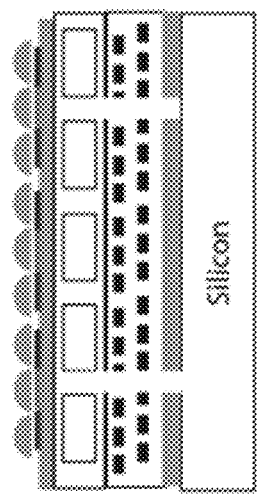

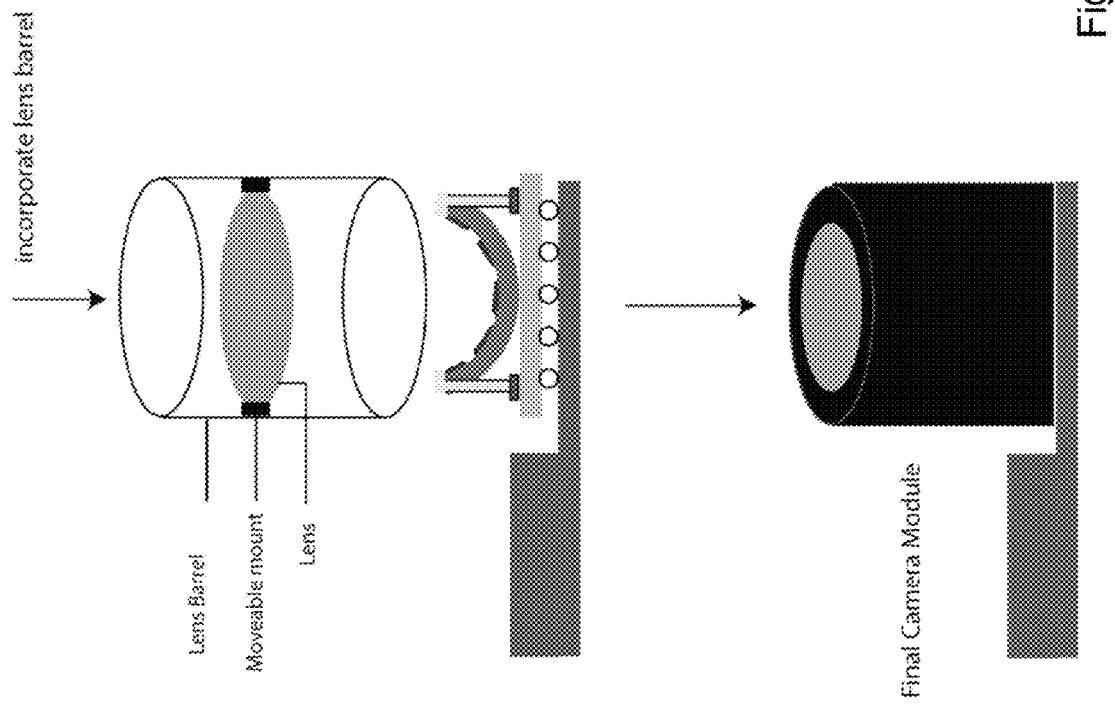

METHODS AND APPLICATIONS OF NON-PLANAR IMAGING ARRAYS

CROSS REFERENCE TO RELATED APPLICATIONS

This application is a continuation of U.S. Ser. No. 14/812,197 filed on Jul. 29, 2015, which is a continuation of U.S. patent application Ser. No. 13/747,826 filed on Jan. 23, 2013, which is a continuation of U.S. patent application Ser. No. 12/686,076, filed on Jan. 12, 2010, now U.S. Pat. No. 8,372,726, which is continuation in part of U.S. patent application Ser. No. 12/636,071, filed on Dec. 11, 2009, now U.S. Pat. No. 8,886,334, which is continuation in part of U.S. patent application Ser. No. 12/616,922, filed on Nov. 12, 2009, now U.S. Pat. No. 8,389,862, which is a continuation in part of U.S. patent application Ser. No. 12/575,008, filed on Oct. 7, 2009, which claims the benefit of the following U.S. Provisional Applications, each of which is incorporated herein by reference in its entirety: U.S. Provisional Patent Application having Ser. No. 61/144,149 filed Jan. 12, 2009 entitled "Non-planar imaging arrays"; and U.S. Provisional Patent Application having Ser. No. 61/156,906 filed Mar. 16, 2009 entitled "Curved imaging array".

This application is a continuation-in-part of copending U.S. Nonprovisional patent application having Ser. No. 12/636,071 filed Dec. 11, 2009 entitled "Systems, Methods, and Devices Using Stretchable Electronics for Medical Applications", which is incorporated herein by reference in its entirety. U.S. Nonprovisional patent application having Ser. No. 12/636,071 claims priority to the following U.S. Provisional Applications: Ser. No. 61/121,568 entitled "Endoscopy Device" filed Dec. 11, 2008; Ser. No. 61/121,541 entitled "Nerve Bundle Prosthesis" filed Dec. 11, 2008; and Ser. No. 61/140,169 entitled "Body Tissue Screener" filed Dec. 23, 2008, the entirety of each of which is incorporated herein by reference. Further, U.S. Nonprovisional patent application having Ser. No. 12/636,071 is a continuation-in-part of and claims the benefit of copending U.S. Nonprovisional patent application Ser. No. 12/616,922 entitled "Extremely Stretchable Electronics" filed Nov. 12, 2009, the entirety of which is incorporated herein by reference. Nonprovisional patent application Ser. No. 12/616,922 claims the benefit of U.S. Provisional Application No. 61/113,622 entitled "Extremely Stretchable Interconnects" filed on Nov. 12, 2008, the entirety of which is incorporated herein by reference. Also, Nonprovisional patent application Ser. No. 12/616,922 is a continuation-in-part of, and claims the benefit of copending U.S. Non-Provisional application Ser. No. 12/575,008, entitled "Catheter Balloon Having Stretchable Integrated Circuitry and Sensor Array" filed on Oct. 7, 2009, the entirety of which is incorporated herein by reference. Nonprovisional application Ser. No. 12/575,008 claims priority to U.S. Provisional Application No. 61/103,361 entitled "Catheter Balloon Sensor and Imaging Arrays", filed Oct. 7, 2008, the entirety of which is incorporated herein by reference; and U.S. Provisional Application No. 61/113,007 entitled "Catheter Balloon with Sensor and Imaging Array", filed Nov. 10, 2008 the entirety of which is incorporated herein by reference.

FIELD OF THE INVENTION

The present invention relates to systems, apparatuses, and methods utilizing expandable or stretchable integrated circuitry and sensor arrays on expandable, flexible or stretchable substrates in or on non-planar imaging arrays.

BACKGROUND OF THE INVENTION

For the purpose of this invention we may consider two types of optical imaging systems: planar and non-planar electronic systems. There are many advantages to using non-planar image sensor arrays including wide field of view, low aberrations and reduced complexity of the systems. However, the majority of available optical imaging systems used today are planar due to restrictions imposed by current techniques used for fabricating optoelectronic systems. Existing technologies are to a large extent geared toward the production of rigid devices on flat surfaces. The resulting systems do not have the ability to absorb strains as required for non-planar designs.

In order to achieve non-planar optoelectronic systems one may process devices directly onto curved surfaces or alternatively onto flat surfaces which are then deformed into the desired shape. Both methods have been actively researched in the past decade with varying degrees of success.

Alternative routes to creating curved focal plane arrays include template generation by ion beam proximity lithography and relief transfer by step and flash imprint lithography; large-scale, heterogeneous integration of nanowire arrays by contact printing; and soft lithographic printing of amorphous silicon on curved substrates. The above-mentioned techniques suffer from limitations with multilevel registration of circuit layers and use of low performance materials which struggle to compete with single crystalline silicon devices currently in use.

Other relevant methods include wet chemical thinning of silicon wafers to produce curved silicon substrates for subsequent processing; and micro-structuring of monolithic silicon die using a deep reactive ion etch on SOI wafers. The prior is not compatible with current semiconductor fabrication processes and the latter is undeveloped due to the plethora of manufacturing challenges. Therefore a need exists for viable routes for production of curved imaging arrays with the utilization of conventional planar processing technology and subsequent deformation to produce different shapes of imaging arrays.

SUMMARY OF THE INVENTION

The present invention pertains to the field of imaging, more specifically the production of curved imaging arrays and its integration into camera modules. These camera modules may be integrated directly into a number of applications for image capture and video recording such as camera phones, web cams, compact camera systems, and the like.

Embodiments of the invention pertain specifically to Complementary Metal Oxide Semiconductor (CMOS) imagers, though one skilled in the art will recognize that Charge-Coupled Device (CCD) imagers can be created in a similar manner. The imaging arrays may be fabricated in hemispherical, ellipsoid, parabolic and other non planar shapes. Methods for creating the above mentioned imaging arrays are described.

The advantages of having a curved imaging array have been known for a long time within the field of optics. The present invention allows the manufacture of cameras with few lenses. This new degree of freedom will further enable the push toward smaller and more discrete imaging devices while reducing the total cost of systems with expensive composite lens components. Fewer lenses results in less reflection and diffraction defects in images. Therefore there is the added benefit of reduced distortion and aberration. Additionally, a curved image sensor reduces system and pixel vignetting by increasing the amount of light entering the sensor and the decreasing the angle of incidence of light entering each pixel. One more important aspect of the curved imager is its ability to significantly increase the field of view of images being recorded.

The invention described herein, avoids the problems of multilevel registration mentioned in the prior art by providing a method which employs conventional semiconductor processing techniques and tools with a high degree of precision. It also overcomes the persistent problem of most flexible/stretchable electronic device by using high performance single crystal silicon for applications that necessitate reliability and superior functionality under strain in complex geometries.

BRIEF DESCRIPTION OF THE DRAWINGS

The present invention will become more fully apparent from the following description and appended claims, taken in conjunction with the accompanying figures. Understanding that these figures merely depict exemplary embodiments of the present invention they are, therefore, not to be considered limiting of its scope. It will be readily appreciated that the components of the present invention, as generally described and illustrated in the figures herein, could be arranged and designed in a wide variety of different configurations. Nonetheless, the invention will be described and explained with additional specificity and detail through the use of the accompanying figures in which:

FIGS. 6A-F depict a method for controlled adhesion on an elastomeric stamp;

FIGS. 7A-K illustrates the process of creating an image sensor via stretch processing;

FIGS. 16A-H outlines a method for transfer printing of "stretch processed" imaging arrays onto the curved surface of a BGA and the subsequent steps required to fabricate a BGA packaged curved image sensor;

FIGS. 17A-B, 18A-F, 19, and 20A-C outline a method for fabricating curved backside illuminated imagers from stretch processed image sensors an incorporating it into a BGA package;

FIGS. 21A-F is a summary of the process shown in FIGS. 17-20;

FIGS. 22A-E illustrates a process of creating a backside illuminated imager with no color filter or micro-lens;

FIGS. 23A-F illustrates a second method for creating a backside illuminated imager with no color filter or lens;

FIGS. 24A-F illustrates a method for creating a planar backside illuminated image sensor;

FIGS. 25A-B illustrates a method for creating a camera module using a curved imaging array;

DETAILED DESCRIPTION OF THE INVENTION

Figure 1:
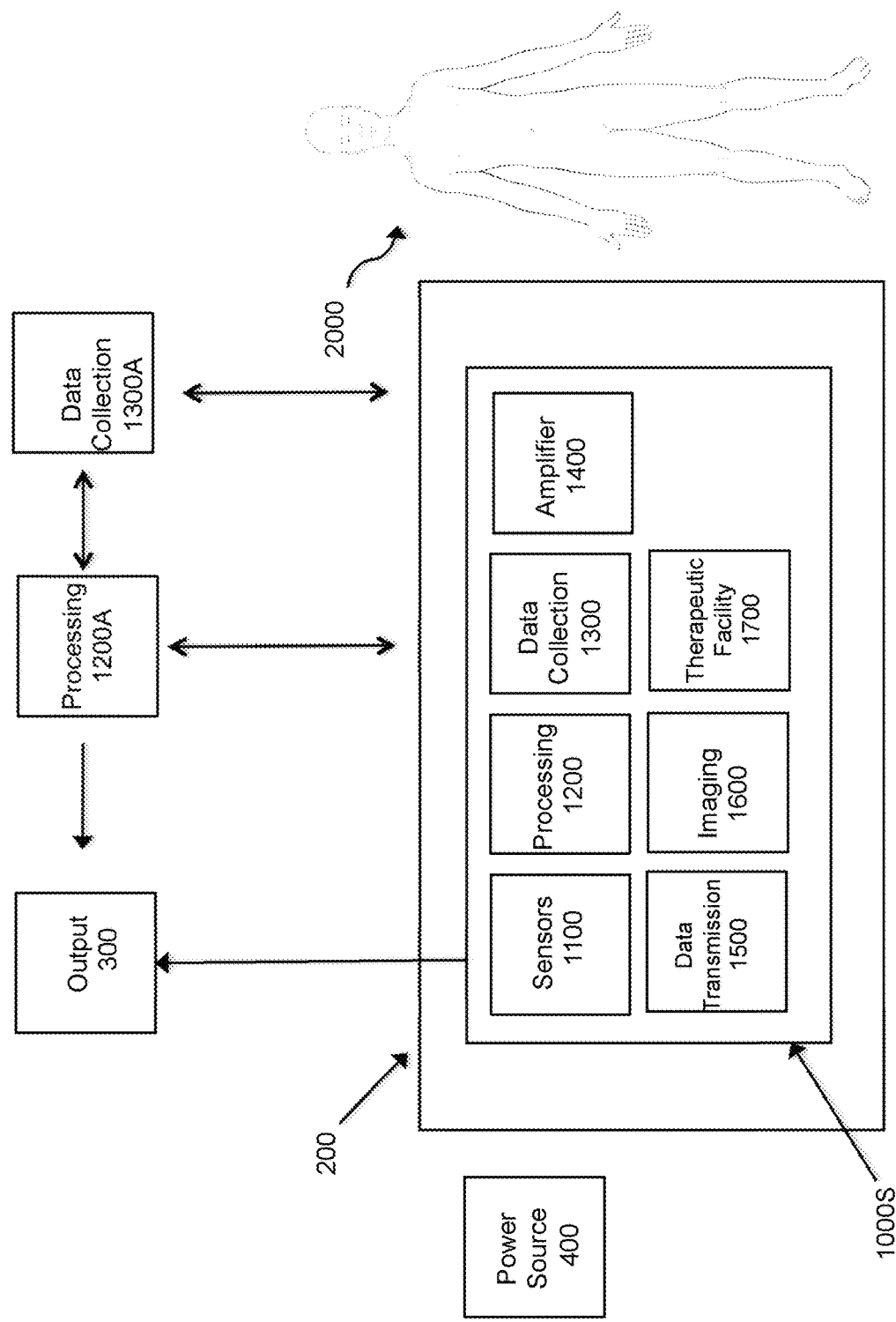
FIG. 1 is a schematic depiction of embodiments of the invention.

Detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting but merely as a basis for the claims and as a representative basis for teaching one skilled in the art to variously employ the present invention in virtually any appropriately detailed structure. Further, the terms and phrases used herein are not intended to be limiting but rather to provide an understandable description of the invention.

The terms "a" or "an," as used herein, are defined as one or more than one. The term "another," as used herein, is defined as at least a second or more. The terms "including" and/or "having" as used herein, are defined as comprising (i.e., open transition). The term "coupled" or "operatively coupled," as used herein, is defined as connected, although not necessarily directly and not necessarily mechanically or physically. "Electronic communication" is the state of being able to convey or otherwise transmit data either through a physical connection, wireless connection, or combinations thereof.

As described herein, the present invention comprises devices, systems, and methods utilizing flexible and/or stretchable electronic circuits on flexible, expandable, or inflatable surfaces. With reference to the present invention, the term "stretchable", and roots and derivations thereof, when used to modify circuitry or components thereof describes circuitry and/or components thereof having soft or elastic properties capable of being made longer or wider without tearing or breaking, and it is also meant to encompass circuitry having components (whether or not the components themselves are individually stretchable as stated above) that are configured in such a way so as to accommodate a stretchable, inflatable, or expandable surface and remain functional when applied to a stretchable, inflatable, or otherwise expandable surface that is stretched, inflated, or otherwise expanded respectively. The term "expandable", and roots and derivations thereof, when used to modify circuitry or components thereof is also meant to have the meaning ascribed above. Thus, "stretch" and "expand", and all derivations thereof, may be used interchangeably when referring to the present invention. The term "flexible", and roots and derivations thereof, when used to modify circuitry or components thereof describes circuitry and/or components thereof capable of bending without breaking, and it is also meant to encompass circuitry having components (whether or not the components themselves are individually flexible as stated above) that are configured in such a way so as to accommodate a flexible surface and remain functional when applied to a flexible surface that is flexed or otherwise bent. In embodiments, at the low end of 'stretchable', this may translate into material strains greater than 0.5% without fracturing, and at the high end to structures that may stretch 100,000% without a degradation of electrical performance. "Bendable" and roots and derivations thereof, when used to modify circuitry or components thereof describes circuitry and/or components thereof able to be shaped (at least in part) into a curve or angle, and may sometimes be used synonymously herein with "flexible".

FIG. 1 is a schematic depiction of embodiments of the invention. Further description of each of the components of FIG. 1 will be included throughout the specification. Circuitry 1000S is applied, secured, or otherwise affixed to substrate 200. In embodiments, substrate 200 is stretchable and or expandable as described herein. As such the substrate 200 can be made of a plastic material or can be made of an elastomeric material, or combinations thereof. Note that the term "plastic" may refer to any synthetic or naturally occurring material or combination of materials that can be molded or shaped, generally when heated, and hardened into a desired shape. The term "elastomer" may refer a naturally occurring material or a synthetic material, and also to a polymeric material which can be stretched or deformed and return to its original shape without substantial permanent deformation. Such elastomers may withstand substantial elastic deformations. Examples of elastomers used in substrate material include polymeric organosilicon compounds (commonly referred to as "silicones") including Polydimethylsiloxane (PDMS).

Other materials suitable for the substrate include polyimide; photopatternable silicone; SU8 polymer; PDS polydustrene; parylene and its derivatives and copolymers (parylene-N); ultrahigh molecular weight polyethylene; poly ether ether ketones (PEEK); polyurethanes (PTG Elasthane®, Dow Pellethane®); polylactic acid; polyglycolic acid; polymer composites (PTG Purisil PTG Bionate®, PTG Carbosil); silicones/siloxanes (RTV 615®, Sylgard 184®)); polytetrafluoroethylene (PTFE, Teflon®); polyamic acid; polymethyl acrylate; stainless steel; titanium and its alloys; platinum and its alloys; and gold. In embodiments, the substrate is made of a stretchable or flexible biocompatible material having properties which may allow for certain devices to be left in a living organism (referred to as the human body 2000) for a period of time without having to be retrieved.

Some of the materials mentioned above, specifically parylene and its derivatives and copolymers (parylene-N); ultrahigh molecular weight polyethylene; poly ether ether ketones (PEEK); polyurethanes (PTG Elasthane®, Dow Pellethane®); polylactic acid; polyglycolic acid; polymer composites (PTG Purisil PTG Bionate®, PTG Carbosil); silicones/siloxanes (RTV 615®, Sylgard 184®); polytetrafluoroethylene (PTFE, Teflon®); polyamic acid; polymethyl acrylate; stainless steel; titanium and its alloys; platinum and its alloys; and gold, are biocompatible. Coatings for the substrate to increase its biocompatibility may include, PTFE, polylactic acid, polyglycolic acid, and poly(lactic-co-glycolic acid).

The materials disclosed for substrate 200 herein may be understood to apply to any of the embodiments disclosed herein that require substrate. It should also be noted that materials can be chosen based on their properties which include degree of stiffness, degree of flexibility, degree of elasticity, or such properties related to the material's elastic moduli including Young's modulus, tensile modulus, bulk modulus, shear modulus, etc., and or their biodegradability.

The substrate 200 can be one of any possible number of shapes or configurations. In embodiments, the substrate 200 is substantially flat and in some embodiments configured to be a sheet or strip. Yet it should be noted that such flat configurations of substrate 200 can be any number of geometric shapes. Other embodiments of flat substrates will be described below including substrates having a tape-like or sheet configuration. Flexible and/or stretchable substrate 200 having a sheet or otherwise substantially flat configuration may be configured such that substrate 200 can be folded, furled, bunched, wrapped or otherwise contained. In embodiments, a substrate 200 configured as such can be folded, furled, bunched, collapsed (such as in an umbrella-like configuration), wrapped, or otherwise contained during delivery through narrow passageways in the subject's body 2000 and then deployed into an unfolded, unfurled, etc. state once in position for deployment.

In embodiments where the substrate 200 is stretchable, circuitry 1000S is configured in the applicable manners described herein to be stretchable and/or to accommodate such stretching of the substrate 200. Similarly, in embodiments where the substrate 200 is flexible, but not necessarily stretchable, circuitry 1000S is configured in the applicable manners described herein to be flexible and/or accommodate such flexing of the substrate 200. Circuitry 1000S can be applied and/or configured using applicable techniques described below, including those described in connection with exemplary embodiments.

As mentioned above, the present invention may employ one or more of a plurality of flexible and/or stretchable electronics technologies in the implementation thereof. Traditionally, electronics have been fabricated on rigid structures, such as on integrated circuits, hybrid integrated circuits, flexible printed circuit boards, and on printed circuit boards. Integrated circuits, also referred to as ICs, microcircuits, microchips, silicon chips, or simple chips, have been traditionally fabricated on a thin substrate of semiconductor material, and have been constrained to rigid substrates mainly due to the high temperatures required in the step of inorganic semiconductor deposition. Hybrid integrated circuits and printed circuit boards have been the main method for integrating multiple ICs together, such as through mounting the ICs onto a ceramic, epoxy resin, or other rigid non-conducting surface. These interconnecting surfaces have traditionally been rigid in order to ensure that the electrical interconnection methods, such as solder joints to the board and metal traces across the boards, do not break or fracture when flexed. In addition, the ICs themselves may fracture if flexed. Thus, the field of electronics has been largely constrained to rigid electronics structures, which then tend to constrain electronics applications that may require flexibility and or stretchability necessary for the embodiments disclosed herein.

Advancements in flexible and bendable electronics technologies have emerged that enable flexible electronics applications, such as with organic and inorganic semiconductors on flexible plastic substrates, and other technologies described herein. Further, stretchable electronics technologies have emerged that enable applications that require the electronics to be stretchable, such as through the use of mounting ICs on flexible substrates and interconnected through some method of stretchable electrical interconnect, and other technologies as described herein. The present invention may utilize one or more of these flexible, bendable, stretchable, and like technologies, in applications that require the electronics to operate in configurations that may not be, or remain, rigid and planar, such as applications that require electronics to flex, bend, expand, stretch and the like.

In embodiments, the circuitry of the invention may be made in part or in full by utilizing the techniques and processes described below. Note that the below description of the various ways to achieve stretchable and/or flexible electronics is not meant to be limiting, and encompasses suitable variants and or modifications within the ambit of one skilled in the art. As such, this application will refer to the following U.S. patents and patent applications, each of which is incorporated by reference herein in its entirety: U.S. Pat. No. 7,557,367 entitled "Stretchable Semiconductor Elements and Stretchable Electrical Circuits", issued Jul. 7, 2009 (the "'367 patent"); U.S. Pat. No. 7,521,292 entitled "Stretchable Form of Single Crystal Silicon for High Performance Electronics on Rubber Substrates", issued Apr. 29, 2009 (the "'292 patent"); United States Published Patent Application No. 20080157235 entitled "Controlled Buckling Structures in Semiconductor Interconnects and Nan membranes for Stretchable Electronics", filed Sep. 6, 2007 (the "'235 application"); U.S. patent application having Ser. No. 12/398,811 entitled "Stretchable and Foldable Electronics", filed Mar. 5, 2009 (the "'811 application"); United States Published Patent Application No. 20040192082 entitled "Stretchable and Elastic Interconnects" filed Mar. 28, 2003 (the "'082 application"); United States Published Patent Application No. 20070134849 entitled "Method For Embedding Dies", filed Nov. 21, 2006 (the "'849 application"); United States Published Patent Application No. 20080064125 entitled "Extendable Connector and Network, filed Sep. 12, 2007 (the "'125 application"); U.S. Provisional Patent Application having Ser. No. 61/240,262 (the '262 application") "Stretchable Electronics", filed Sep. 7, 2009; U.S. patent application having Ser. No. 12/616,922 entitled "Extremely Stretchable Electronics", filed Nov. 12, 2009 (the "'922 application"); U.S. Provisional Patent Application having Ser. No. 61/120,904 entitled "Transfer Printing", filed Dec. 9, 2008 (the "'904 application"); United States Published Patent Application No. 20060286488 entitled "Methods and Devices for Fabricating Three-Dimensional Nanoscale Structures", filed Dec. 1, 2004; U.S. Pat. No. 7,195,733 entitled "Composite Patterning Devices for Soft Lithography" issued Mar. 27, 2007; United States Published Patent Application No. 20090199960 entitled "Pattern Transfer Printing by Kinetic Control of Adhesion to an Elastomeric Stamp" filed Jun. 9, 2006; United States Published Patent Application. No. 20070032089 entitled "Printable Semiconductor Structures and Related Methods of Making and Assembling" filed Jun. 1, 2006; United States Published Patent Application No. 20080108171 entitled "Release Strategies for Making Transferable Semiconductor Structures, Devices and Device Components" filed Sep. 20, 2007; and United States Published Patent Application No. 20080055581 entitled "Devices and Methods for Pattern Generation by Ink Lithography", filed Feb. 16, 2007.

"Electronic device" is used broadly herein to encompass an integrated circuit(s) having a wide range of functionality. In embodiments, the electronic devices may be devices laid out in a device island arrangement, as described herein including in connection to exemplary embodiments. The devices can be, or their functionality can include, integrated circuits, processors, controllers, microprocessors, diodes, capacitors, power storage elements, antennae, ASICs, sensors, image elements (e.g. CMOS, CCD imaging elements), amplifiers, A/D and D/A converters, associated differential amplifiers, buffers, microprocessors, optical collectors, transducer including electro-mechanical transducers, piezoelectric actuators, light emitting electronics which include LEDs, logic, memory, clock, and transistors including active matrix switching transistors, and combinations thereof. The purpose and advantage of using standard ICs (in embodiments, CMOS, on single crystal silicon) is to have and use high quality, high performance, and high functioning circuit components that are also already commonly mass-produced with well known processes, and which provide a range of functionality and generation of data far superior to that produced by a passive means. Components within electronic devices or devices are described herein, and include those components described above. A component can be one or more of any of the electronic devices described above and/or may include a photodiode, LED, TUFT, electrode, semiconductor, other light-collecting/detecting components, transistor, contact pad capable of contacting a device component, thin-film devices, circuit elements, control elements, microprocessors, interconnects, contact pads, capacitors, resistors, inductors, memory element, power storage element, antenna, logic element, buffer and/or other passive or active components. A device component may be connected to one or more contact pads as known in the art, such as metal evaporation, wire bonding, application of solids or conductive pastes, and the like.

Components incapable of controlling current by means of another electrical signal are called passive devices. Resistors, capacitors, inductors, transformers, and diodes are all considered passive devices For purposes of the invention, an active device is any type of circuit component with the ability to electrically control electron flow. Active devices include, but are not limited to, vacuum tubes, transistors, amplifiers, logic gates, integrated circuits, semiconducting sensors and image elements, silicon-controlled rectifiers (SCRs), and triode for alternating current (TRIACs).

"Ultrathin" refers to devices of thin geometries that exhibit flexibility.

"Functional layer" refers to a device layer that imparts some functionality to the device. For example, the functional layer may be a thin film, such as a semiconductor layer. Alternatively, the functional layer may comprise multiple layers, such as multiple semiconductor layers separated by support layers. The functional layer may comprise a plurality of patterned elements, such as interconnects running between device-receiving pads.

Semiconductor materials which may be used to make circuits may include amorphous silicon, polycrystalline silicon, single crystal silicon, conductive oxides, carbon annotates and organic materials.

In some embodiments of the invention, semiconductors are printed onto flexible plastic substrates, creating bendable macro-electronic, micro-electronic, and/or nano-electronic devices. Such bendable thin film electronics devices on plastic may exhibit field effect performance similar to or exceeding that of thin film electronics devices fabricated by conventional high temperature processing methods. In addition, these flexible semiconductor on plastic structures may provide bendable electronic devices compatible with efficient high throughput processing on large areas of flexible substrates at lower temperatures, such as room temperature processing on plastic substrates. This technology may provide dry transfer contact printing techniques that are capable of assembling bendable thin film electronics devices by depositing a range of high quality semiconductors, including single crystal Si ribbons, GaAs, INP wires, and carbon nano-tubes onto plastic substrates. This high performance printed circuitry on flexible substrates enables an electronics structure that has wide ranging applications. The '367 patent and associated disclosure illustrates an example set of steps for fabricating a bendable thin film electronics device in this manner. (See FIG. 26A of the '367 patent for Example).

In addition to being able to fabricate semiconductor structures on plastic, it has been demonstrated that metal-semiconductor electronics devices may be formed with printable wire arrays, such as GaAs micro-wires, on the plastic substrate. Similarly, other high quality semiconductor materials have been shown to transfer onto plastic substrates, including Si nano-wires, micro-ribbons, platelets, and the like. In addition, transfer printing techniques using elastomeric stamps may be employed. The '367 patent provides an example illustration of the major steps for fabricating, on flexible plastic substrates, electronics devices that use arrays of single wires (in this instance GaAs wires) with epitaxial channel layers, and integrated holmic contacts. (See FIG. 41 of the '367 patent). In an example, a semi-insulating GaAs wafer may provide the source material for generating the micro-wires. Each wire may have multiple ohmic stripes separated by a gap that defines the channel length of the resultant electronic device. Contacting a flat, elastomeric stamp of PDMS to the wires forms a van der Waals bond. This interaction enables removal of all the wires from the wafer to the surface of the PDMS when the stamp is peeled back. The PDMS stamp with the wires is then placed against an uncured plastic sheet. After curing, peeling off the PDMS stamp leaves the wires with exposed ohmic stripes embedded on the surface of the plastic substrate. Further processing on the plastic substrate may define electrodes that connect the ohmic stripes to form the source, drain, and gate electrodes of the electronics devices. The resultant arrays are mechanically flexible due to the bendability of the plastic substrate and the wires.

In embodiments, and in general, stretchable electronics may incorporate electrodes, such as connected to a multiplexing chip and data acquisition system. In an example, an electrode may be fabricated, designed, transferred, and encapsulated. In an embodiment, the fabrication may utilize and/or include an SI wafer; spin coating an adhesion layer (e.g. an HMDS adhesion layer); spin coating (e.g. PMMA) patterned by shadow mask, such as in oxygen RIE; spin coating Polyimide; depositing PECVD SiO2; spin 1813 Resist, photolithography patterning; metal evaporation (e.g. Ti, Pt, Au, and the like, or combination of the aforementioned); gold etchant, liftoff in hot acetone; spin Polyimide; PECVD SiO2; spin 1813 Resist, photolithography patterning; RIE etch, and the like. In this embodiment, the fabrication step may be complete with the electrodes on the Si wafer. In embodiments, the Si wafer may then be bathed in a hot acetone bath, such as at 100 C for approximately one hour to release adhesion layer while PI posts keep electrode adhered to the surface of the Si wafer. In embodiments, electrodes may be designed in a plurality of shapes and distributed in a plurality of distribution patterns. Electrodes may be interconnected to electronics, multiplexing electronics, interface electronics, a communications facility, interface connections, and the like including any of the facilities/elements described on connection with FIG. 1 and/or the exemplary embodiments herein. In embodiments, the electrodes may be transferred from the Si wafer to a transfer stamp, such as a PDMS stamp, where the material of the transfer stamp may be fully cured, partially cured, and the like. For example, a partially cured PDMS sheet may be ~350 nm, where the PDMS was spun on at 300 rpm for 60s, cured 65 C for 25 min, and used to lift electrodes off of the PDMS sheet. In addition, the electrodes may be encapsulated, such as wherein the electrodes are sandwiched between a supporting PDMS layer and second PDMS layer while at least one of the PDMS layers is partially cured.

In embodiments, stretchable electronics configurations may incorporate flex PCB design elements, such as flex print, chip flip configurations (such as bonded onto the PCB), and the like, for connections to electrodes and/or devices, and for connections to interface electronics, such as to a data acquisition system (DAQ). For example, a flex PCB may be joined to electrodes by an anisotropic conductive film (ACF) connection, solder joints may connect flex PCB to the data acquisition system via conductive wires, and the like. In embodiments, the electrodes may be connected onto a surface by employing a partially-cured elastomer (e.g. PDMS) as an adhesive.

In embodiments, stretchable electronics may be formed into sheets of stretchable electronics. In embodiments, stretchable sheets may be thin, such as approximately 100 Optionally, amplification and multiplexing may be implemented without substantially heating the contact area, such as with micro-fluidic cooling.

In embodiments, a sheet having arrays of electronic devices comprising electrodes may be cut into different shapes and remain functional, such as through communicating electrode islands which determine the shape of the electrode sheet. Electrodes are laid out in a device island arrangement (as described herein) and may contain active circuitry designed to communicate with each other via inter-island stretchable interconnects so that processing facility (described herein) in the circuitry can determine in real-time the identity and location of other such islands. In this way, if one island becomes defective, the islands can still send out coordinated, multiplexed data from the remaining array. Such functionality allows for such arrays to be cut and shaped based on the size constraints of the application. A sheet, and thus circuitry, may be cut to side and the circuitry will poll remaining electrodes and/or devices to determine which are left and will modify the calibration accordingly. An example of a stretchable electronics sheet containing this functionality, may include electrode geometry, such as a 20×20 array of platinum electrodes on 1 mm pitch for a total area of 20×20 mm$^2$; an electrode impedance, such as 5 kohm at 1 khz (adjustable); a configuration in a flexible sheet, such as with a 50 μm total thickness, and polyimide encapsulated; a sampling rate, such as 2 kHz per channel; a voltage dynamic range, such as +/−6 mV; a dc voltage offset range, such as −2.5 to 5 V, with dc rejection; a voltage noise, such as 0.002 mV, a maximum signal-to-noise ratio, such as 3000; a leakage current, such as 0.3 μA typical, 10 μA maximum, as meets IEC standards, and the like; an operating voltage of 5 V; an operating power per channel, such as less than 2 mW (adjustable); a number of interface wires, such as for power, ground, low impedance ground, data lines, and the like; a voltage gain, such as 150; a mechanical bend radius, such as 1 mm; a local heating capability, such as heating local tissue by up to 1° C.; biocompatibility duration, such as 2 weeks; active electronics, such as a differential amplifier, a multiplexer (e.g. 1000 transistors per channel); a data acquisition system, such as with a 16 bit A/D converter with a 500 kHz sampling rate, less than 2 μV noise, data login and real-time screen display; safety compliance, such as to IEC10601; and the like.

In embodiments of the invention, mechanical flexibility may represent an important characteristic of devices, such as on plastic substrates, for many applications. Micro/nano-wires with integrated ohmic contacts provide a unique type of material for high performance devices that can be built directly on a wide range of device substrates. Alternatively, other materials may be used to connect electrical components together, such as connecting electrically and/or mechanically by thin polymer bridges with or without metal interconnects lines.

In embodiments, an encapsulation layer may be utilized. An encapsulating layer may refer to coating of the device, or a portion of the device. In embodiments, the encapsulation layer may have a modulus that is inhomogeneous and/or that spatially varies. Encapsulation layers may provide mechanical protection, device isolation, and the like. These layers may have a significant benefit to stretchable electronics. For example, low modulus PDMS structures may increase the range of stretchability significantly (described at length in the '811 application). The encapsulation layer may also be used as a passivation later on top of devices for the protection or electrical isolation. In embodiments, the use of low modulus strain isolation layers may allow integration of high performance electronics. The devices may have an encapsulation layer to provide mechanical protection and protection against the environment. The use of encapsulation layers may have a significant impact at high strain. Encapsulants with low moduli may provide the greatest flexibility and therefore the greatest levels of stretchability. As referred to in the '811 application, low modulus formulations of PDMS may increase the range of stretchability at least from 60%. Encapsulation layers may also relieve strains and stresses on the electronic device, such as on a functional layer of the device that is vulnerable to strain induced failure. In embodiments, a layering of materials with different moduli may be used. In embodiments, these layers may be a polymer, an elastomer, and the like. In embodiments, an encapsulation may serve to create a biocompatible interface between an implanted stretchable electronic system, such as Silk encapsulation of electronic devices in contact with tissue.

Returning to flexible and stretchable electronics technologies that may be utilized in the present invention, it has been shown that buckled and wavy ribbons of semiconductor, such as GaAs or Silicon, may be fabricated as part of electronics on elastomeric substrates. Semiconductor ribbons, such as with thicknesses in the submicron range and well-defined, 'wavy' and/or 'buckled' geometries have been demonstrated. The resulting structures, on the surface of, or embedded in, the elastomeric substrate, have been shown to exhibit reversible stretchability and compressibility to strains greater than 10%. By integrating ohmic contacts on these structured GaAs ribbons, high-performance stretchable electronic devices may be achieved. The '292 patent illustrates steps for fabricating stretchable GaAs ribbons on an elastomeric substrate made of PDMS, where the ribbons are generated from a high-quality bulk wafer of GaAs with multiple epitaxial layers (See FIG. 22). The wafer with released GaAs ribbons is contacted to the surface of a pre-stretched PDMS, with the ribbons aligned along the direction of stretching. Peeling the PDMS from the mother wafer transfers all the ribbons to the surface of the PDMS. Relaxing the prestrain in the PDMS leads to the formation of large scale buckles/wavy structures along the ribbons. The geometry of the ribbons may depend on the prestrain applied to the stamp, the interaction between the PDMS and ribbons, and the flexural rigidity of the ribbons, and the like. In embodiments, buckles and waves may be included in a single ribbon along its length, due for example, to thickness variations associated with device structures. In practical applications, it might be useful to encapsulate the ribbons and devices in a way that maintains their stretchability. The semiconductor ribbons on an elastomeric substrate may be used to fabricate high-performance electronic devices, buckled and wavy ribbons of semiconductor multilayer stacks and devices exhibiting significant compressibility/stretchability. In embodiments, the present invention may utilize a fabrication process for producing an array of devices utilizing semiconductor ribbons, such as an array of CMOS inverters with stretchable, wavy interconnects. Also, a strategy of top layer encapsulation may be used to isolate circuitry from strain, thereby avoiding cracking.

In embodiments, a neutral mechanical plane (NMP) in a multilayer stack may define the position where the strains are zero. For instance, the different layers may include a support layer, a functional layer, a neutral mechanical surface adjusting layer, an encapsulation layer with a resultant neutral mechanical surface such as coincident with the functional layer, and the like. In embodiments, the functional layer may include flexible or elastic device regions and rigid island regions. In embodiments, an NMP may be realized in any application of the stretchable electronics as utilized in the present invention.

In embodiments, semiconductor ribbons (also, micro-ribbons, nano-ribbons, and the like) may be used to implement integrated circuitry, electrical interconnectivity between electrical/electronic components, and even for mechanical support as a part of an electrical/electronic system. As such, semiconductor ribbons may be utilized in a great variety of ways in the configuration/fabrication of flexible and stretchable electronics, such as being used for the electronics or interconnection portion of an assembly leading to a flexible and/or stretchable electronics, as an interconnected array of ribbons forming a flexible and/or stretchable electronics on a flexible substrate, and the like. For example, nano-ribbons may be used to form a flexible array of electronics on a plastic substrate. The array may represent an array of electrode-electronics cells, where the nano-ribbons are pre-fabricated, and then laid down and interconnected through metallization and encapsulation layers. Note that the final structure of this configuration may be similar to electronic device arrays as fabricated directly on the plastic, as described herein, but with the higher electronics integration density enabled with the semiconductor ribbons. In addition, this configuration may include encapsulation layers and fabrication steps which may isolate the structure from a wet environment. This example is not meant to limit the use of semiconductor ribbons in any way, as they may be used in a great variety of applications associated with flexibility and stretchability. For example, the cells of this array may be instead connected by wires, bent interconnections, be mounted on an elastomeric substrate, and the like, in order to improve the flexibility and/or stretchability of the circuitry.

Wavy semiconductor interconnects is only one form of a broader class of flexible and stretchable interconnects that may (in some cases) be referred to as 'bent' interconnects, where the material may be semiconductor, metal, or other conductive material, formed in ribbons, bands, wire, traces, and the like. A bent configuration may refer to a structure having a curved shape resulting from the application of a force, such as having one or more folded regions. These bent interconnections may be formed in a variety of ways, and in embodiments, where the interconnect material is placed on an elastomeric substrate that has been pre-strained, and the bend form created when the strain is released. In embodiments, the pre-strain may be pre-stretched or pre-compressed, provided in one, two, or three axes, provided homogeneously or heterogeneously, and the like. The wavy patterns may be formed along pre-strained wavy patterns, may form as 'pop-up' bridges, may be used with other electrical components mounted on the elastomer, or transfer printed to another structure. Alternately, instead of generating a 'pop-up' or buckled components via force or strain application to an elastomeric substrate, a stretchable and bendable interconnect may be made by application of a component material to a receiving surface. Bent configurations may be constructed from micro-wires, such as transferred onto a substrate, or by fabricating wavy interconnect patterns either in conjunction with electronics components, such as on an elastomeric substrate.

Figure 2:
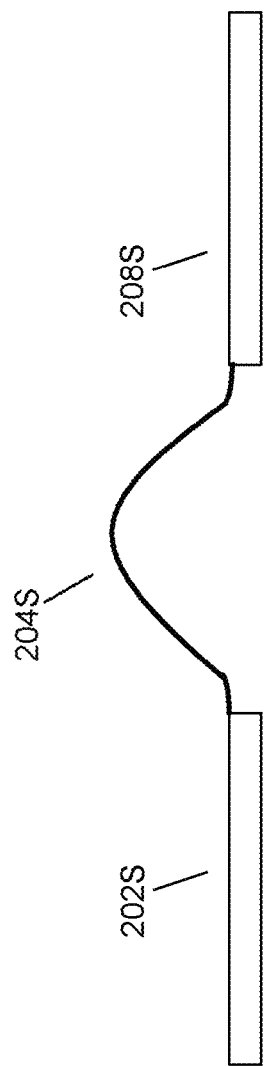
FIG. 2 depicts a buckled interconnection.

Semiconductor nanoribbons, as described herein, may utilize the method of forming wavy 'bent' interconnections through the use of forming the bent interconnection on a pre-strained elastomeric substrate, and this technique may be applied to a plurality of different materials. Another general class of wavy interconnects may utilize controlled buckling of the interconnection material. In this case, a bonding material may be applied in a selected pattern so that there are bonded regions that will remain in physical contact with the substrate (after deformation) and other regions that will not. The pre-strained substrate is removed from the wafer substrate, and upon relaxation of the substrate, the unbounded interconnects buckle ('pop-up') in the unbonded (or weakly bonded) regions. Accordingly, buckled interconnects impart stretchability to the structure without breaking electrical contact between components, thereby providing flexibility and/or stretchability. FIG. 2 shows a simplified diagram showing a buckled interconnection 204S between two components 202S and 208S.

In embodiments, any, all, or combinations of each of the interconnection schemes described herein may be applied to make an electronics support structure more flexible or bendable, such as applying bent interconnects to a flexible substrate, such as plastic or elastomeric substrates. However, these bent interconnect structures may provide for a substantially more expandable or stretchable configuration in another general class of stretchable electronic structures, where rigid semiconductor islands are mounted on an elastomeric substrate and interconnected with one of the plurality of bent interconnect technologies. This technology is presented here, and also in the '262 application, which has been incorporated by reference in its entirety. This configuration also uses the neutral mechanical plane designs, as described herein, to reduce the strain on rigid components encapsulated within the system. These component devices may be thinned to the thickness corresponding to the desired application or they may be incorporated exactly as they are obtained. Devices may then be interconnected electronically and encapsulated to protect them from the environment and enhance flexibility and stretchability.

Figure 3:
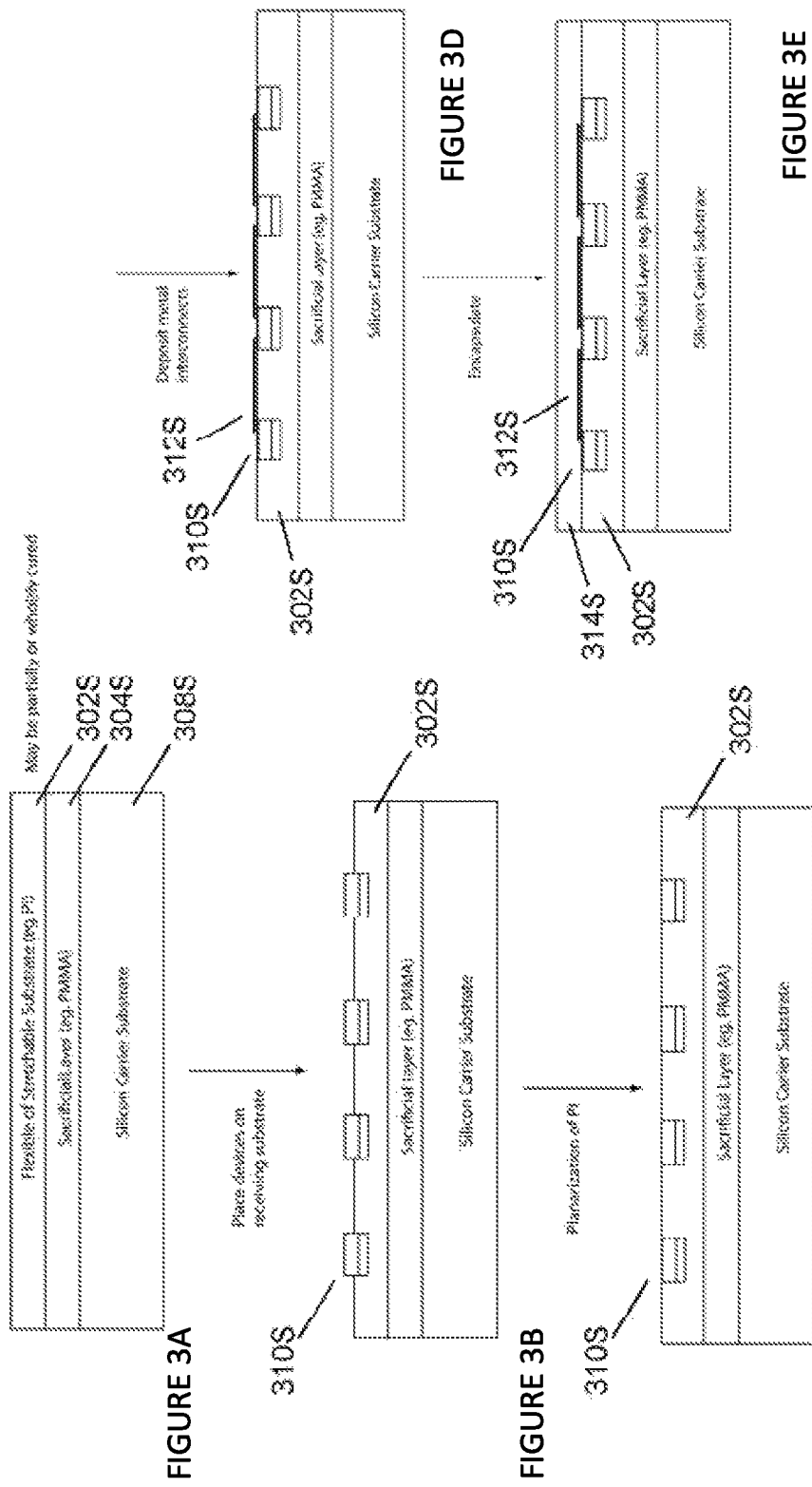
FIGS. 3A-E depict a stretchable electronics configuration with semiconductor; islands mounted on an elastomeric substrate with stretchable interconnects.

In an embodiment, the first step in a process to create stretchable and flexible electronics as described herein involves obtaining required electronic devices and components and conductive materials for the functional layer. The electronics are then thinned (if necessary) by using a back grinding process. Many processes are available that can reliably take wafers down to 50 microns. Dicing chips via plasma etching before the grinding process allows further reduction in thickness and can deliver chips down to 20 microns in thickness. For thinning, typically a specialized tape is placed over the processed part of the chip. The bottom of the chip is then thinned using both mechanical and/or chemical means. After thinning, the chips may be transferred to a receiving substrate, wherein the receiving substrate may be a flat surface on which stretchable interconnects can be fabricated. FIG. 3 illustrates an example process, which begins by creating a flexible substrate 302S on the carrier 308S coated with a sacrificial layer 304S (FIG. 3A), placing devices 310S on the flexible substrate (FIG. 3B), and performing a planarization step in order to make the top surface of the receiving substrate the same height as that of the die surface (FIG. 3C). The interconnect fabrication process follows. The devices 310S deposited on the receiving substrate are interconnected 312S which join bond pads from one device to another (FIG. 3D). In embodiments, these interconnects 312S may vary from 10 microns to 10 centimeters. A polymeric encapsulating layer 314S may then be used to coat the entire array of interconnected electronic devices and components (FIG. 2E). The interconnected electronic devices are then released from the substrate by etching away sacrificial materials with a solvent. The devices are then ready to undergo stretch processing. They are transferred from the rigid carrier substrate to an elastomeric substrate such as PDMS. Just before the transfer to the new substrate, the arrays are pre-treated such that the device/component islands preferentially adhere to the surface leaving the encapsulated interconnects free to be displaced perpendicular to the receiving substrate.

In embodiments, the interconnect system is a straight metal line connecting two or more bond pads. In this case the electronic array is transferred to a pre-strained elastomeric substrate. Upon relaxation of this substrate the interconnects will be displaced perpendicular to the substrate, thus producing outward buckling. This buckling enables stretching of the system.

In another embodiment, the interconnects are a serpentine pattern of conductive metal. These types of interconnected arrays need not be deposited on a pre-strained elastomeric substrate. The stretchability of the system is enabled by the winding shape of the interconnects.

Stretchable/flexible circuits may be formed on paper, plastic, elastomeric, or other materials with the aid of techniques including but not limited to conventional photolithographic techniques, sputtering, chemical vapor deposition, ink jet printing, or organic material deposition combined with patterning techniques. Semiconductor materials which may be used to make circuits may include amorphous silicon, polycrystalline silicon, single-crystal silicon, conductive oxides, carbon nanotubes and organic materials. In embodiments, the interconnects may be formed of electrically conducting film, stripe, pattern, and the like, such as on an elastomer or plastic material, where the film may be made to buckle, deform, stretch, and the like, as described herein. In embodiments, the interconnect may be made of a plurality of films, such as on or embedded in the flexible and/or a stretchable substrate or plastic.

Figure 4:
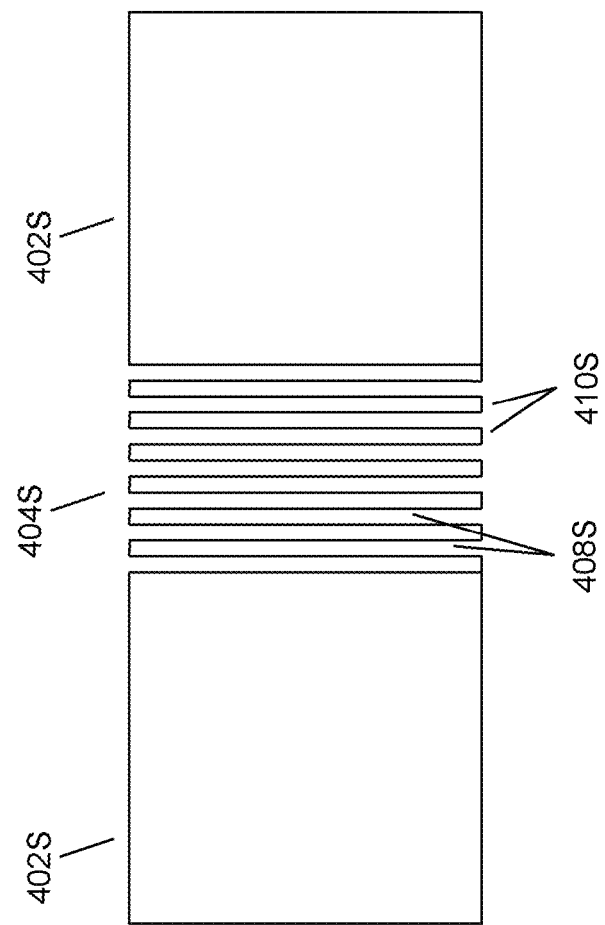
FIG. 4 depicts an extremely stretchable interconnect.

In embodiments, the interconnection of device islands 402S may utilize an extremely stretchable interconnect 404S, such as shown in FIG. 4, and such as the various configurations disclosed in the '922 application. The geometry and the dimension of the interconnects 404S is what makes them extremely compliant. Each interconnect 404S is patterned and etched so that its structural form has width and thickness dimensions that may be of comparable size (such as their ratio or inverse ratio not exceeding about a factor of 10); and may be preferably equal in size. In embodiments, the interconnect may be formed in a boustrophedonic style such that it effectively comprises long bars 408S and short bars 410S. This unique geometry minimizes the stresses that are produced in the interconnect when subsequently stretched because it has the effective form of a wire, and behaves very differently than interconnect form factors having one dimension greatly exceeding the other two (for example plates). Plate type structures primarily relieve stress only about a single axis via buckling, and withstand only a slight amount of shear stress before cracking. This invention may relieve stress about all three axes, including shears and any other stress. In addition, because the interconnect may be formed out of rigid materials, after being stretched it may have a restorative force which helps prevent its wire-like form from getting tangled or knotted when re-compressing to the unstretched state. Another advantage of the boustrophedonic geometry is that it minimizes the initial separation distance between the islands. In embodiments, the interconnects may be formed either monolithically (i.e., out of the same semiconductor material as the device islands) or may be formed out of another material.

Figure 5:
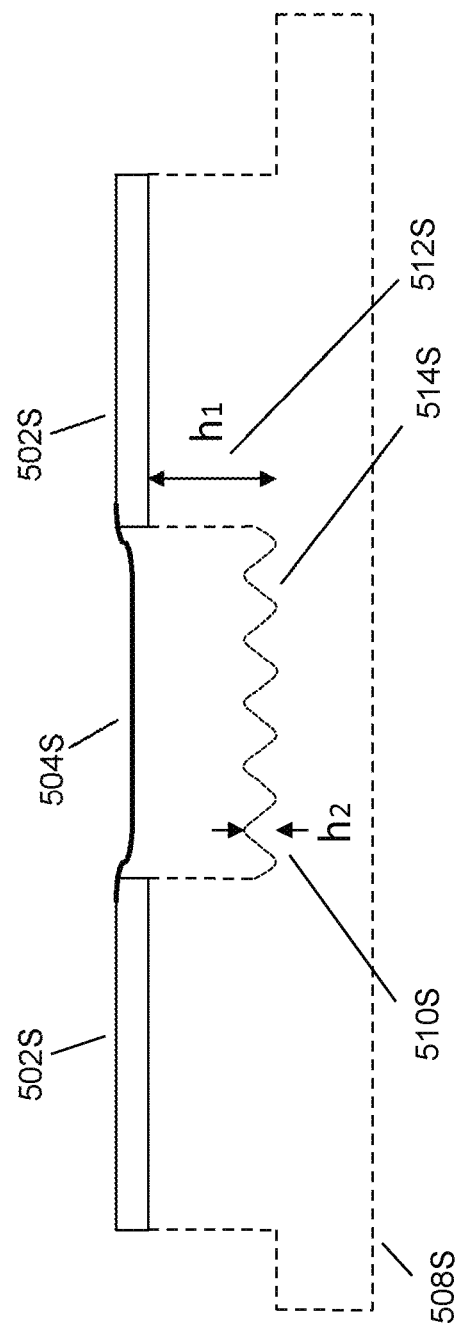
FIG. 5 depicts a raised stretchable interconnect with expandable elastomeric substrate.

In another embodiment the elastomeric substrate may comprise two layers separated by a height 512S, such as shown in FIG. 5. The top "contact" layer contacts the device island 502S, where the device islands 502S are interconnected 504S with one of the interconnection schemes described herein. In addition, the bottom layer may be a "wavy" layer containing ripples 514S or square waves molded into the substrate 508S during elastomer fabrication. These waves enable additional stretching, whose extent may depend on the amplitude 510S and wavelength of the waves pattern-molded in the elastomer.

In embodiments, the device island may be any prefabricated integrated circuit (IC), where the IC may be mounted on, inside, between, and the like, a flexible and/or stretchable substrate. For example, an additional elastomeric layer may be added above the structure as shown in FIG. 5, such as to encapsulate the structure for protection, increased strength, increase flexibility, and the like. Electrical contacts to embedded electrical components may be provided across the embedded layer, through the elastomeric layer(s) from a second electrical interconnection layer, and the like. For example, an IC may be encapsulated in a flexible material where the interconnects are made accessible as described in the '849 application. (See FIG. 1 of the '849 application for example). In this example the embedded IC is fabricated by first placing the IC onto a carrier, such as a rigid carrier, and where the IC may be a thinned IC (either thinned before the mounting on the carrier, or thinned while on the carrier). A second step may involve a coating of the IC with some adhesive, elastomer, or other insulating material that can be flowed onto the IC. A third step may be to gain access to the electrical contacts of the IC, such as by laser drilling or other method known to the art. A fourth step may be to flow electrical conductor into the openings, thus establishing an electrical access to the electrical connections of the IC. Finally, the IC thus encased may be freed from the carrier. Now the structure may be more easily embedded into a flexible substrate while maintaining electrical connectivity. In embodiments, this structure may be a flexible structure, due to the thinness of the IC, the elastic character of the surrounding structure, the elastic configuration of the extended electrical contacts, and the like.

It should be noted that many of the stretchable electronics techniques utilize the process of transfer printing, for example, with a PDMS stamp. In embodiments, the present invention may include a method of dynamically controlling the surface adhesion of a transfer printing stamp, such as described here, and disclosed in the '904 application. Transfer printing stamps have many uses, one of which is to pick up thin films of materials ("targets") from one surface ("initial surface") and deposit them onto another surface ("final surface"). The pickup may be achieved by pressing the transfer printing stamp into contact with the targets, applying some pressure to create Van der Waals bonds between the stamp and the targets, peeling off the stamp with the targets, and then placing the stamp with targets into contact with another surface, applying pressure, and peeling off the stamp without the targets so they remain on the final surface. If the final surface has a higher bonding strength with the targets than the transfer stamp, they will remain on the final surface when the transfer stamp is peeled off. Alternately, the rate of peeling the transfer stamp can be adjusted to vary the target to stamp and target to final surface bonding force ratio. The present invention describes a novel method of depositing the targets, by changing the surface adhesion of the transfer stamp after the targets have been picked up. This may be done while the stamp with targets is in contact with the final surface. In embodiments, the adhesion control can be done by introducing micro-fluidic channels into the transfer stamp, so that water or other fluid can be pumped to the surface of the stamp from within it, thereby changing the surface adhesion from sticky to non-sticky.

In embodiments, the present invention may accomplish transfer printing by using a transfer printing stamp that has been formed with micro-fluidic channels such that a fluid (liquid or gas) can be pumped to the surface of the stamp to wet or chemically functionalize the surface and therefore change the surface adhesion of the stamp surface. The transfer printing stamp may be made out of any material, including but not limited to poly-dimethyl-siloxane (PDMS) and derivatives thereof. In one non-limiting embodiment, the stamp is a piece of PDMS formed into a cuboid, which may have dimensions ranging from about 1 micrometer to 1 meter. For this example, the cuboid is 1 cm×1 cm×0.5 cm (length, width, thickness). One 1 cm×1 cm surface of the cuboid is designated as the stamping face. By using a photolithography mask, or a stencil mask, a pattern of vertical holes (channels) is etched from the stamping face through to the opposing face of the stamp. This may be done with an oxygen reactive ion etch. These holes are the micro-fluidic channels, and may be about 0.1-10 micrometers in diameter. They may be spaced apart by about 1-50 micrometers. Another piece of PDMS may be formed into a reservoir shape (eg. a 1 cm×1 cm×0.5 cm cuboid with a smaller cuboid (about 0.8 cm×0.8 cm×0.3 cm) cut out from one surface). This shape may be formed by pouring the PDMS into a mold, curing it, and removing it from the mold. This additional piece of PDMS may then be placed into contact with the first piece of PDMS and bonded (this may be done via ultraviolet ozone exposure or oxygen plasma exposure of the PDMS prior to contacting the two pieces) such that the two pieces form the shape shown in FIG. 6, step A. Then, one or more holes may be punctured into the top of the reservoir so that a fluidic pipe can be fitted for pumping water into the stamp. In another non-limiting embodiment, the stamp is constructed as described above, except that the first piece of PDMS is formed to have micro-fluidic channels by means of molding. PDMS molding is a well known art. First, a mold is created that is the inverse of the desired shape. In this case, that is an array of vertical posts on a base with four walls. This mold is then filled with PDMS by pouring in the PDMS, allowing it to cure (which may be at elevated temperature), and then removing the PDMS. In another non-limiting embodiment, the stamping surface is also patterned with an array of shallow-etched surface channels. In embodiments, these channels may be about 100-10000 nm wide, and 100-10000 nm etched-into the PDMS. They may form a linear array or a checkerboard grid. The purpose of the channels is to help distribute a liquid from the vertical micro-fluidic channels around the surface of the stamp. In addition, these channels serve to allow an exit for the air that must be displaced to push the liquid to the surface of the stamp. An example of a liquid that may be used includes, but is not limited to, water (which will wet the surface of the stamp and decrease its adhesivity). In the case of a gas fluid, these surface channels may not be necessary. Examples of gasses that can lower the surface adhesion of PDMS are dimethyldichlorosilane (DDMS), perfluorooctyltrichlorosilane (FOTS), perfluorodecyltris(dimethylamino)silane (PF10TAS), and perfluorodecanoic acid (PFDA), and the like.

In embodiments, the stamp may be operated as shown in FIG. 6. First, it is pressed into contact with a substrate that has the target material or devices to be picked up. (FIG. 6A). The target material is picked up by Van der Waal's forces between itself and the stamp as is well known (FIG. 6B,C). Target material is placed in contact with the final substrate, and pressed into contact (FIG. 6D). The fluid (for example, water) is pumped to the stamp surface, to reduce adhesion (FIG. 6E). The stamp may be left in this state (of contact with water) for as long as necessary for the water to fully wet the stamp surface. Finally, the stamp is removed, leaving the target material behind on the final substrate (FIG. 6F). In FIG. 6A-F, the following labels are made for clarity: fluid inlet 601S; PDMS stamp 602S; fluid distribution reservoir 603S; micro-fluidic channels to stamp surface 604S; adhesive stamp surface 605S; devices to be picked up and transfer printed 6; initial substrate 607S; final substrate 608S; pump in water 609S so it reaches the end of the micro-fluidic channels to alter the surface adhesion of the transfer stamp and release the devices. Note that any surface channels on the stamp surface are not shown in the Figure, and the Figure is not drawn to scale.

Another example of configurations to enable stretchable circuitry are as described in the '125 application in connection with an extendable interconnect. (See FIG. 3 of the '125 application). The electrical component may be considered as one of a plurality of interconnected nodes, whose interconnections expand/extend as the underlying flexible substrate expands. In embodiments, flexible and stretchable electronics may be implemented in a great variety of ways, including configurations involving the substrate, the electrical components, the electrical interconnects, and the like, and involve electrical, mechanical, and chemical processes in their development and implementation.

As amply discussed herein, CMOS devices offer a variety sophisticated functionality including sensing, imaging, processing, logic, amplifiers, buffers, A/D converters, memory, clock and active matrix switching transistors. The electronic devices or the "device islands" of the stretchable/flexible circuitry of the present invention may be devices and are themselves capable of performing the functionality described herein, or portions thereof.

In embodiments, devices and device islands, devices are to be understood as "active" as described above.

In embodiments, the electronic devices are optionally laid out in a device island arrangement, as described herein. The functionality described herein with respect to circuitry 1000S and thus electronic devices may thus be present in an electronic device itself, spread across arrays of electronic devices and/or device components, or achieved via electronic communication and cooperation with other electronic devices and/or device components each electronic device (or electronic device and device component combination) having separate or additive, but complementary functions that will become apparent from this disclosure. In embodiments, such electronic communication could be wireless. Therefore, said devices may comprise a transducer, transmitter, or receiver capable of such wireless transmission.

Returning to FIG. 1, this figure schematically depicts the functionality of the circuitry 1000S (and thus the electronic devices, device components, or combinations thereof). Elements 1100-1700 and their sub elements and components including electronic devices, device components, or combinations thereof may be present in the circuitry 1000S individually or in any combination as applicable. Certain combinations will be discussed below; however, the below discussions merely depict exemplary embodiments of the present invention and thus they are therefore not to be considered limiting of its scope. It will be readily appreciated that the elements of circuitry 1000S, as generally described herein, could be arranged and designed in a wide variety of different configurations. Nonetheless, the invention will be described and explained with additional specificity and detail.

Circuitry 1000S comprises sensors (alternatively termed "sensor devices") 1100 to detect various parameters. Thus, to achieve the detection parameters, sensors may include thermistors, thermocouples, silicon band gap temperature sensors, thin-film resistance temperature devices, LED emitters, optical sensors including photodetectors, electrodes, piezoelectric sensors, ultrasonic including ultrasound emitters and receivers; ion sensitive field effect transistors, and microneedles.

The separation distance between sensors (e.g., sensor device islands) can be any that is manufacturable, a useful range may be, but is not limited to, 10 µm-10000 µm. In embodiments, sensors 1100 can be characterized as sensor circuits. Individual sensors may be coupled to a differential amplifier, and/or a buffer and/or an analog to digital converter. The resulting sensor circuits may be formed on the same, or different, devices than the sensors themselves. The circuits may be laid out in an active matrix fashion such that the readings from multiple sensors 1100 can be switched into and processed by one or a few amplifier/logic circuits. Signals from the array of sensors 1100 (or any devices herein) can be processed using multiplexing techniques, including those described in published international patent application WO2009/114689 filed Mar. 12, 2009 the entirety of which is hereby incorporated herein by reference. Multiplexor component circuitry may be located on or within the circuitry 1000S on the substrate 200, or at a location that avoids interference with the operation of the device such as for example at the base of a catheter guide wire although other areas that avoid interference with operation will be apparent.)

Circuitry 1000S comprises processing facility 1200 (alternatively referred to herein as "processor", "processing", and the terms mentioned immediately below) which may include a signal processor, digital processor, embedded processor, microcontroller, microprocessor, ASIC, or the like that may directly or indirectly facilitate execution of program code or program instructions stored thereon or accessible thereto. In addition, the processing facility 1200 may enable execution of multiple programs, threads, and codes. The threads may be executed simultaneously to enhance the performance of the processing facility 1200 and to facilitate simultaneous operations of the application. By way of implementation, methods, program codes, program instructions and the like described herein may be implemented in one or more thread. The thread may spawn other threads that may have assigned priorities associated with them; the processing facility 1200 may execute these threads based on priority or any other order based on instructions provided in the program code. The processing facility 1200 (and/or the circuitry 1000S in general) may include or be in electronic communication memory that stores methods, codes, instructions and programs as described herein and elsewhere. The processing facility 1200 may access a storage medium through an interface that may store methods, codes, and instructions to perform the methods and functionality described herein and elsewhere. Processing facility 1200 comprised in or is in electronic communication with the other elements of the circuitry 1000S including the electronic devices and/or device components. Off-board processing facility 1200A comprises all the functionality described above; however, is physically separate from circuitry 1000S yet in electronic communication thereto.

Data collection facility 1300 (and off-board data collection facility 1300A) are configured to each independently or both collect and store data generated by the circuitry 1000S and the elements thereof including imaging facility 1600 (discussed below), and therapeutic facility 1700. Data transmission facility 1500 includes a means of transmitting (RF and/or wired) the sensor information to processing facility 1200 or off-board processing facility 1200A. Each of the elements 1100-1700 are also configured to be in electronic communication with one another and need not necessarily communicate through the data transmission facility 1500. In embodiments, circuitry 1000S and/or data transmission facility 1500 is in electronic communication with output facility 300 which, in embodiments, can be in electronic communication with processing facility 1200A or a separate processing facility. The various outputs described herein should be understood to emanate from the output facility 300.

In embodiments, circuitry 1000S may be connected or otherwise in electronic communication with external/separate devices and systems by physical connection, including the methods described above and by providing conductive pads on the circuitry 1000S in an accessible location or location that avoids interference with the operation of the device and interfacing anisotropic conductive film (ACF) connectors to the conductive pads. Also, the circuitry 1000S and/or associated devices 1010S may comprise a transducer, transmitter, transceiver, or receiver capable of wireless transmission and thus wireless communication with external/separate devices and systems. In addition, circuitry 1000S islands may be made to perform optical data communication down a waveguide, such as the one described below.

Power source 400 can supply power to circuitry 1000S in any number of ways, including externally optically, with a waveguide and having PV cells made in a stretchable/flexible format in addition to the rest of the circuitry. Alternately, thin film batteries may be used to power the circuitry 1000S, which could enable an apparatus to be left in the body and communicate with the operator. Alternately, RF communication circuits on the apparatus may not only be used to facilitate wirelessly communication between devices within the circuitry and/or to external/separate systems, but they may also receive RF power to power the circuits. Using such approaches, the need for external electrical interfaces may be eliminated.

Circuitry 1000S includes therapeutic facility 1700 in embodiments of the invention, include various elements to effect a desired therapy. In embodiments, circuitry can comprise heat or light activated drug-delivery polymers that when activated could release chemical agents, such as anti-inflammatory drugs, to local sites in the body. Therefore, in embodiments, light emitting electronics (such as LED) could be utilized to activate a drug delivery polymer.

In embodiments of the invention, circuitry 1000S comprises imaging circuitry 1600. Imaging circuitry 1600 in embodiments comprises a packed array of active pixel sensors. Each pixel in the array may contain a photodetector, a pn junction blocking diode, an active amplifier, and an analog to digital converter, formed in a single piece of single crystalline silicon (50×50 µm2; 1.2 µm thick). In embodiments, Imaging circuitry 16000 may be encapsulated with a polymer layer such as PDMS to prevent contact stress induced damage. Imaging circuitry 1600 can comprise an array of photodetectors on the substrate 200 positioned in close proximity to the site of interest within the subject's body 2000 can provide high spatial resolution imaging without the need for a lens-based focusing due to the proximity of the photodetectors to the tissue. Imaging circuitry 1600 comprise a light source comprising or connected to an optical fiber or an LED to provide illumination to the photodetectors for imaging the tissue of interest.

Exemplary configurations for the circuitry 1000S including imaging facility 1600 methods, configurations as well as fabrication techniques will be described below. However, it should be understood that any embodiment of circuitry (and therefore its electronic devices, components, and other functional elements) described herein in shall apply to any of the exemplary embodiments. The exemplary configurations and techniques are not to be considered limiting of scope. It will be readily appreciated that the circuitry elements, configurations, and fabrication techniques of the present invention, as generally described herein, could be utilized, arranged or otherwise implemented in a wide variety of different ways. Also, and by way of clarification, the circuitry configurations and functional elements as well as the fabrication techniques described for this (and all exemplary embodiments) described herein shall be considered to apply to each or any of the embodiments disclosed herein and as such should not be considered as uniquely and exclusively applying to the particular exemplary embodiments being described.

Embodiments of the imaging facility 1600 may involve a non-planar electronic imaging array composed of flexible and stretchable electronic components. The flexibility and stretchability of the array enables curved configurations. These arrays may be integrated into a number of imaging systems including microscopes, surveillance systems, endoscopes, infra-red imagers, telescopes, sophisticated cameras, scanners, machine vision systems, vehicle navigation systems, computer input devices, auto focus systems, star trackers, motion detection systems, image stabilization systems and data compression systems for high-definition television, and the like. The stretchable electronic components are primarily in the form of active and/or passive pixel arrays which can be incorporated into the imaging systems detailed above. The electronic components may be arranged in islands, which house required circuitry and are interconnected mechanically and electronically via interconnects. The interconnects, in turn, preferentially absorb strain and thus channel destructive forces away from the device islands. They provide a mechanism by which the integrated circuits can stretch and flex when a force is applied. The present invention primarily references the device islands which consist of one or more pixel units for imaging purposes. However, stretchable electronic devices and device components which may be incorporated into an "island" are not limited to this description. The device islands and interconnects may be integrated into the structure of the end product or system level device by transfer printing. This is described further herein. Encapsulation of electronic devices and system/device interconnect integration may be performed at any of a number of stages in this process.

The circuitry used in the imaging array and accompanying electronic devices may comprise standard IC sensors, transducers, interconnects and computation/logic elements. These devices are typically made on a silicon-on-insulator (SOI) wafer in accordance with a circuit design implementing the desired functionality. Alternatively, the semiconductor devices may be processed on suitable carrier wafers which provide a top layer of ultrathin semiconductor supported by an easily removed layer (eg. Polymethyl methacrylate, PMMA). These wafers are used to fabricate flex/stretch ICs by standard processes, with island and interconnect placement being tailored to the requirements of a particular application.

A representative, non-limiting example of fabrication steps utilized in creating an electronic device in accordance with the present invention is as follows. It will be appreciated by one skilled in the art that other stretchable electronics methods as described herein may be alternately applied in the creating a non-planar imaging device in accordance with the present invention.

In embodiments, electrical devices may be laid out in a device "island" arrangement. In, one embodiment of the invention, the device islands may typically be 1 µm×1 µm-1000 µm×1000 µm in area. However, other feature sizes may be utilized as required. These islands can accommodate at least one pixel which may include a photo sensing material and associated circuitry (e.g. transistors, in the case of active pixel arrays). Larger islands may have the capacity to hold more than one component or pixel. The islands may be connected to a buffer and/or an amplifier. Islands may accommodate active matrix switches, A/D converters, logic circuitry capable of reading in digital signals and processing them, and are capable of outputting data or storing data in memory cells. Additionally, some islands are simply designed and used as metal contact pads. At least one electrical and/or mechanical interconnection is found between each island.

Figures 7A, 7B:
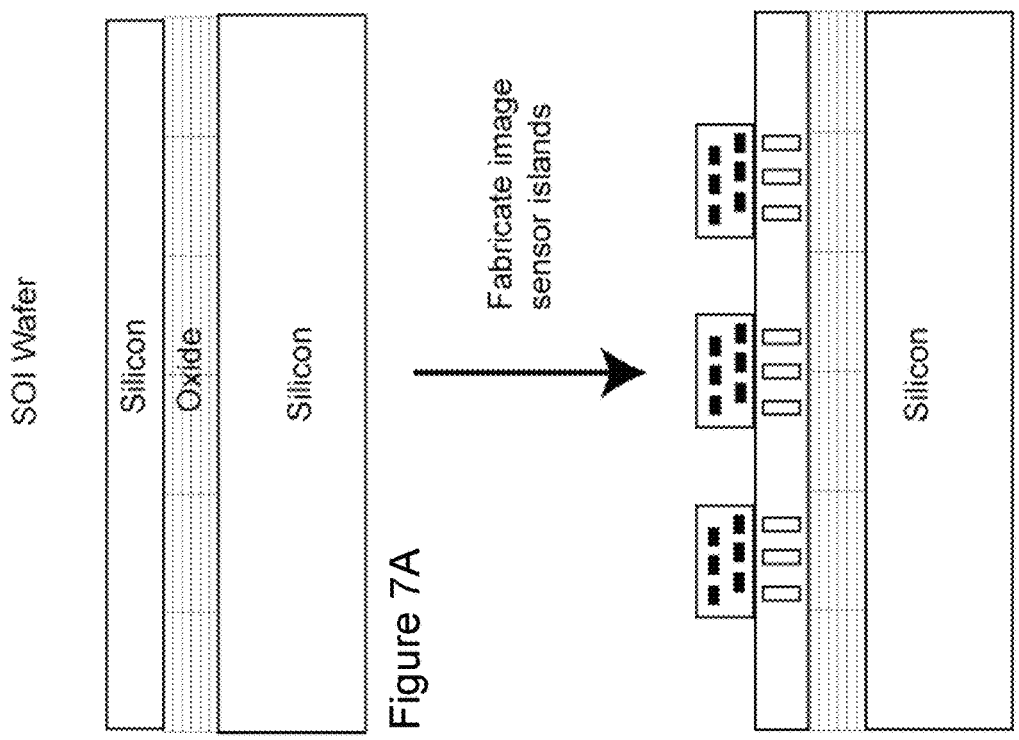

As shown in FIG. 7A, the image sensors may be fabricated on a planar SOI wafer (e.g. thickness from 100 nm to 100 µm thick; this example is a 1.2 µm thick top Si, 1 µm thick buried oxide) using standard CMOS fabrication technology. The image sensors may also be fabricated using non-silicon material such as germanium, gallium arsenide, indium phosphide, lead sulphide, and the like.

Figure 8:
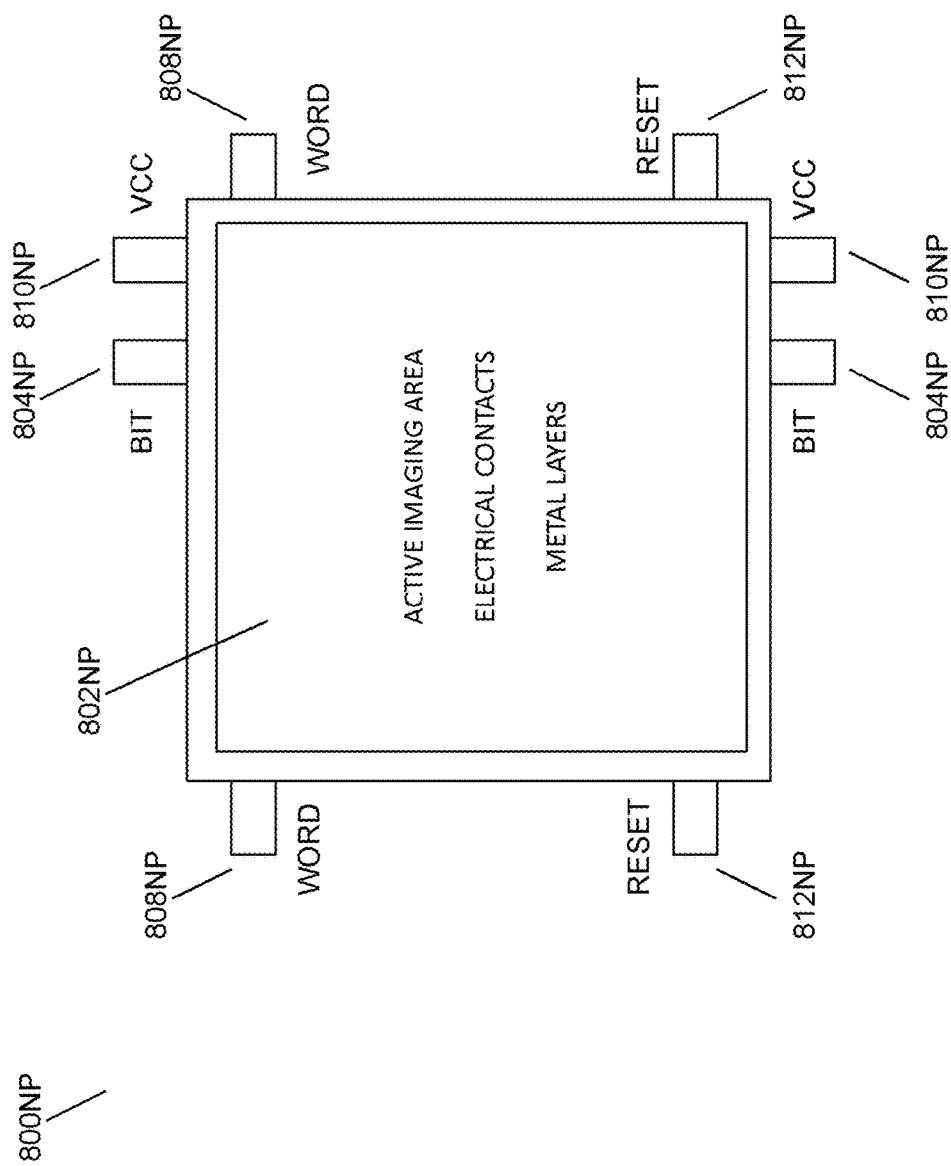
FIG. 8 is an illustration of a CMOS active pixel.
Figure 9:
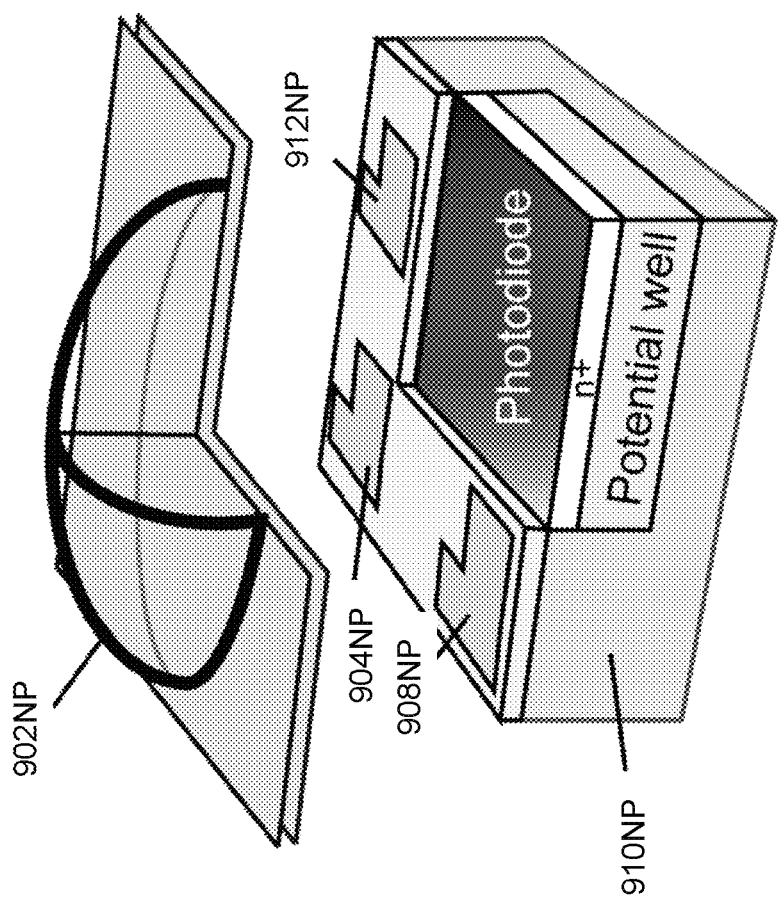
FIG. 9 is an illustration of a second CMOS active pixel.

As shown in FIG. 8, each pixel 800NP may be laid out in an array 802NP. As shown, the pixel may have control and power contacts, such as for bit 804NP and word 808NP selection, and power (Vcc) 810NP and reset 812NP. The array may be laid out such as in a 1 µm×1 µm island array, such as spaced apart by 1-100 µm from any adjacent island, and the like. After stretch processing, this inter island gap may be shrunk due to contraction of the entire array. Pixel dimensions may vary within the limits of island size (e.g. 1 µm×1 µm-1000 µm×1000 µm in area with an exemplary pixel pitch around 2 µm and thus an island of 100 µm2 will contain about 25 pixels). FIG. 9 shows an additional active pixel design that may be used, including a micro-lens 902NP, amplifier transistor 904NP, bus transistor 908NP, silicon substrate 910NP, reset transistor 912NP, and the like.

One embodiment of the imaging array is a CMOS active pixel array made using a 2 metal layer process. The array is designed using rules specified for the integration of mechanical bridges and electrical interconnects into the system. Image sensor grids are fabricated on an SOI wafer separated by gaps (FIG. 7B). These gaps facilitate the formation of stretchable interconnects at a later stage. The silicon under each gap is then etched away to isolate image sensor islands (FIG. 7C). This space may be important when considering the final non-planar shape of the imaging array. In order for the pixels to be evenly spaced in the final non-planar shape, the pixels/island separation may need to be unequal in the planar layout. Hence, the interconnect between islands may be of different lengths. Calculations are done on a case by case basis to determine the optimal layout of islands in the planar design in order to achieve uniform density of pixels in the non-planar imaging array. For instance, the spaces between image sensors may range from 100 nm to 100 µm.

In an example, the image sensor islands are protected by a first polyimide (PI) passivation layer, then a short HF etch step is applied to partially undercut the islands (FIG. 7D). The first passivation layer is removed, and then a thin film of SiO2 (100 nm thick) may be deposited and patterned by PECVD or other deposition technique combined with a lift-off procedure, such that the oxide layer covers most of the space between device islands except for a region that is about 5 µm wide (FIG. 7E). The purpose of this oxide layer is to act as a sacrificial layer during the final etch step so that the PI that is deposited in the next step only adheres to the underlying silicon in a small ~5 □m wide region that has sufficient adhesive force to prevent the devices from floating away in the HF etch but not too much adhesive force to prevent high yield transfer printing.

A second polyimide layer is spun on and patterned to form the shape of the interconnect wires/bridges between the islands (FIG. 7F). Typically one bridge may extend from the center of one island edge to the center of another island edge. This design was used in a passive matrix imaging array. Alternately, two bridges may extend from each corner of the device island to two different device island corners. Other bridge configurations may also be utilized especially for designs which aim to reduce the overall mechanical strain in the final stretchable system (determined by mechanical modeling). One exemplary interconnect design has a tightly packed serpentine layout and connects from one corner of an island to the corner of an adjacent island. In embodiments, interconnect bridges may be about 100 nm to 500 µm wide and may accommodate multiple electrical lines.

Figure 10:
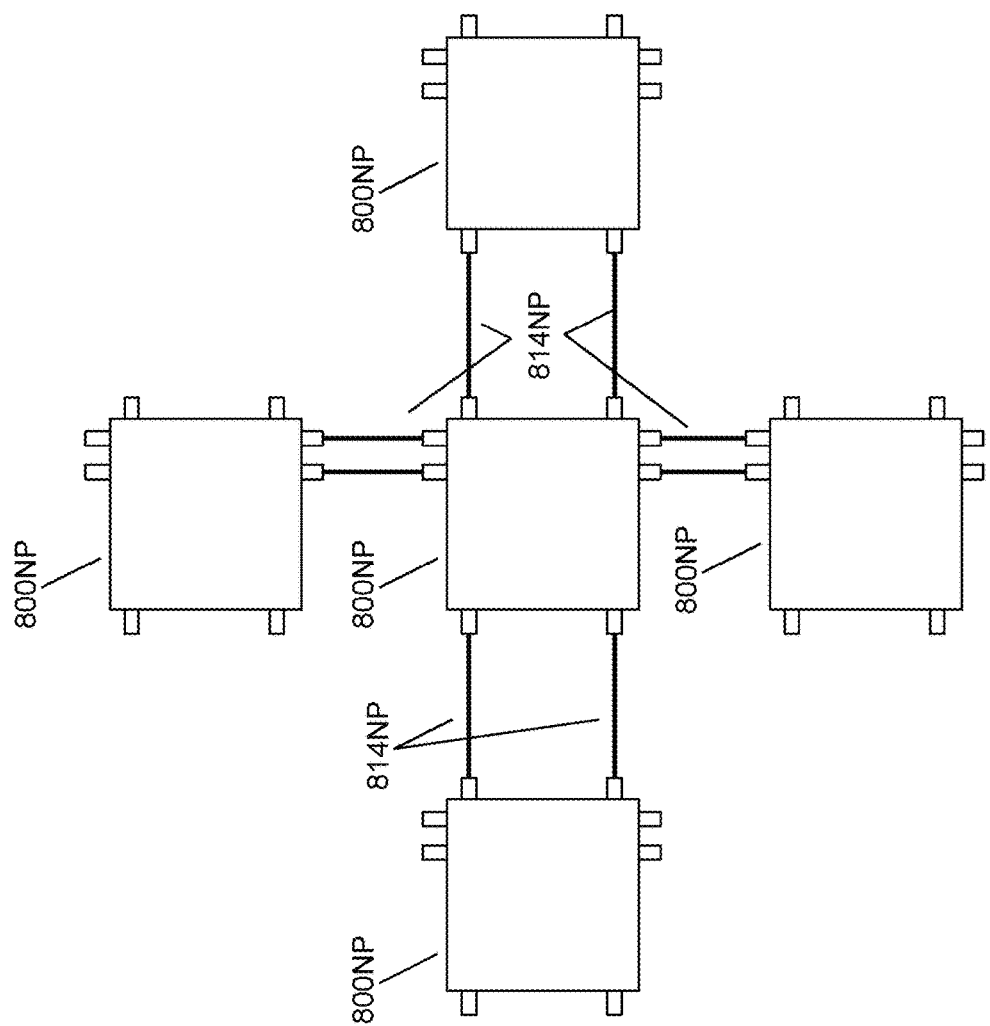
FIG. 10 is an illustration of an interconnected pixel array with one pixel per island.
Figure 11:
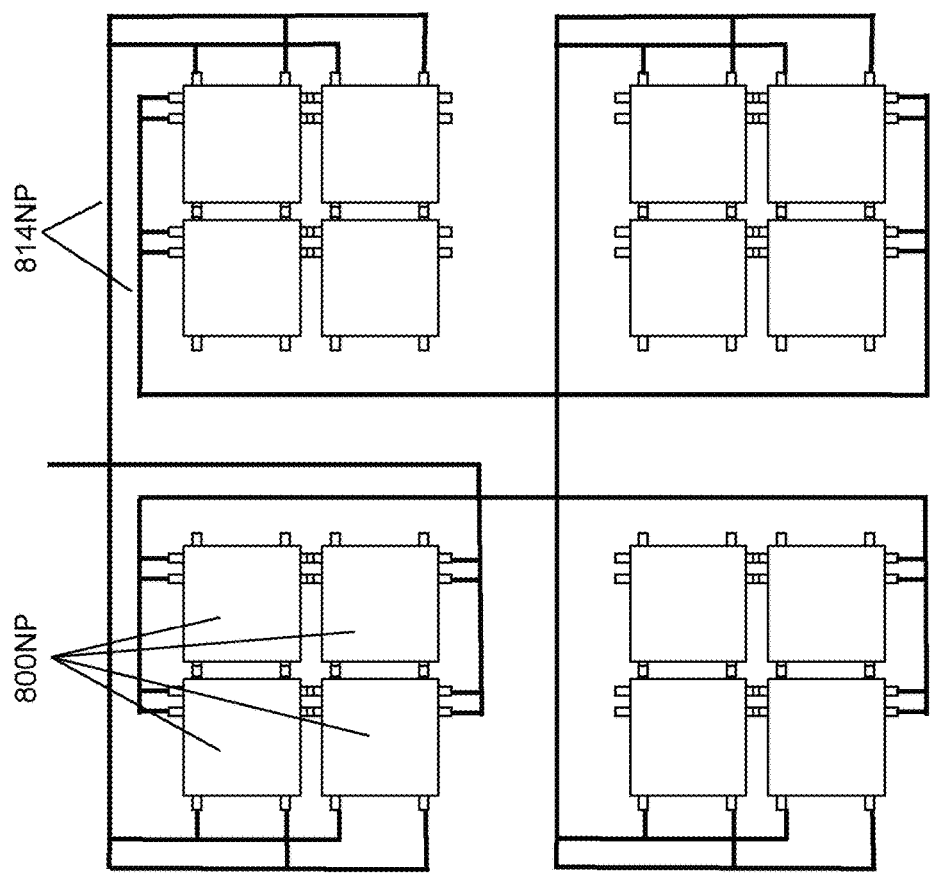
FIGS. 11-13 are illustrations of an interconnected pixel array with 4 pixels per island.
Figure 12:
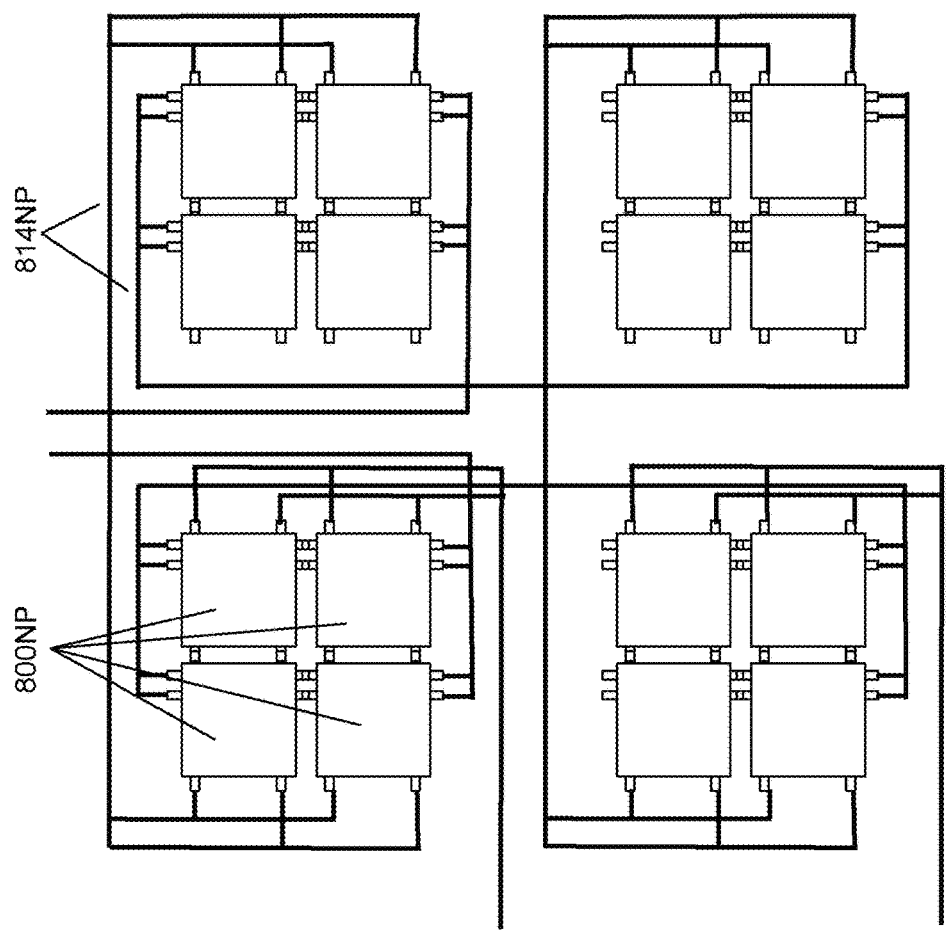
Figure 13:
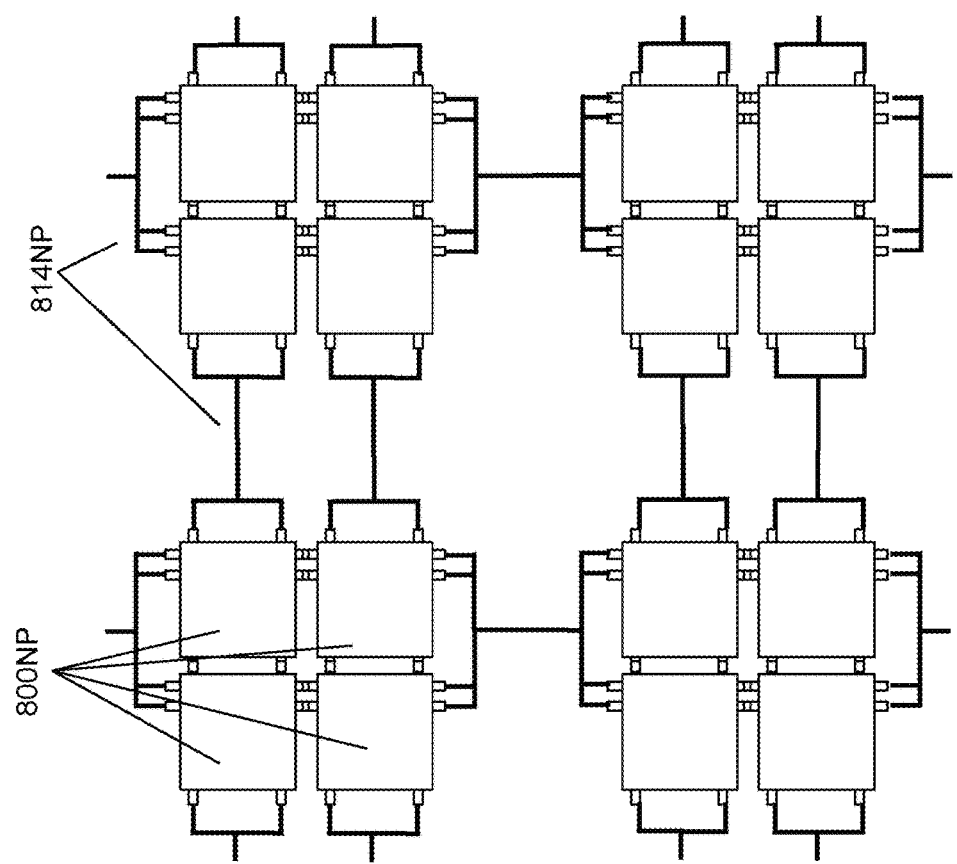

The second polyimide layer partially fills where the device island is undercut; this serves to stabilize the island later in the release process and to prevent its migration. Vias are etched into the second PI layer to make metal interconnects. Next, a third metal layer is patterned to contact the circuits and connect word, bit, reset and vcc lines from one island to another (FIG. 7G). In one embodiment of the invention, the islands are made up of one pixel each. In this example the third metal layer contacts points 1-8 through vias as show in the FIG. 10. Vias are made down to the first and/or second metal layers as required, facilitating electrical contact between the sensor's word, bit, reset and Vcc lines and the third metal layer. In another embodiment of the invention, the islands are comprised of multiple pixels. FIGS. 11-13 illustrate a number of designs which may be useful for interconnecting islands with multiple pixels.

In one embodiment of the image sensor, a color filter array (e.g. Bayer Color filter array) is then deposited onto each pixel (FIG. 7H). This is accomplished by using a pigment infused photoresist (eg. diazonaphthoquinone DNQ-Novolac) as done in conventional color filter deposition. For applications that do not require color images, this step may be omitted.

Figure 7I:
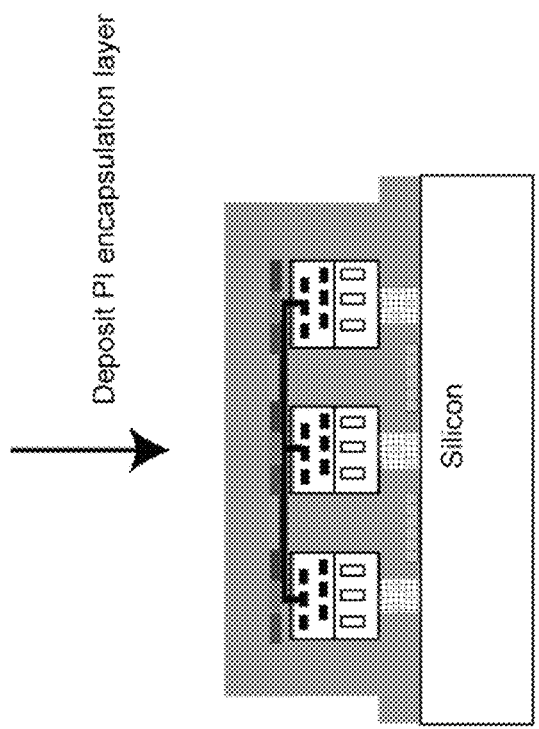
Figure 7J:
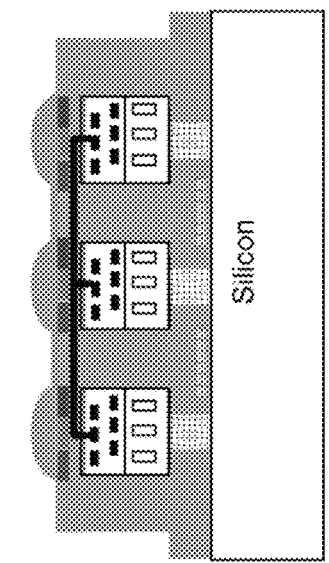

A third PI layer is spun on (covering the wires and everything else) (FIG. 7I). In one embodiment of the invention, the third PI layer may then be processed using laser ablation and thermal reflow to create an array of microlenses as shown in (FIG. 7J).

Figure 7K:
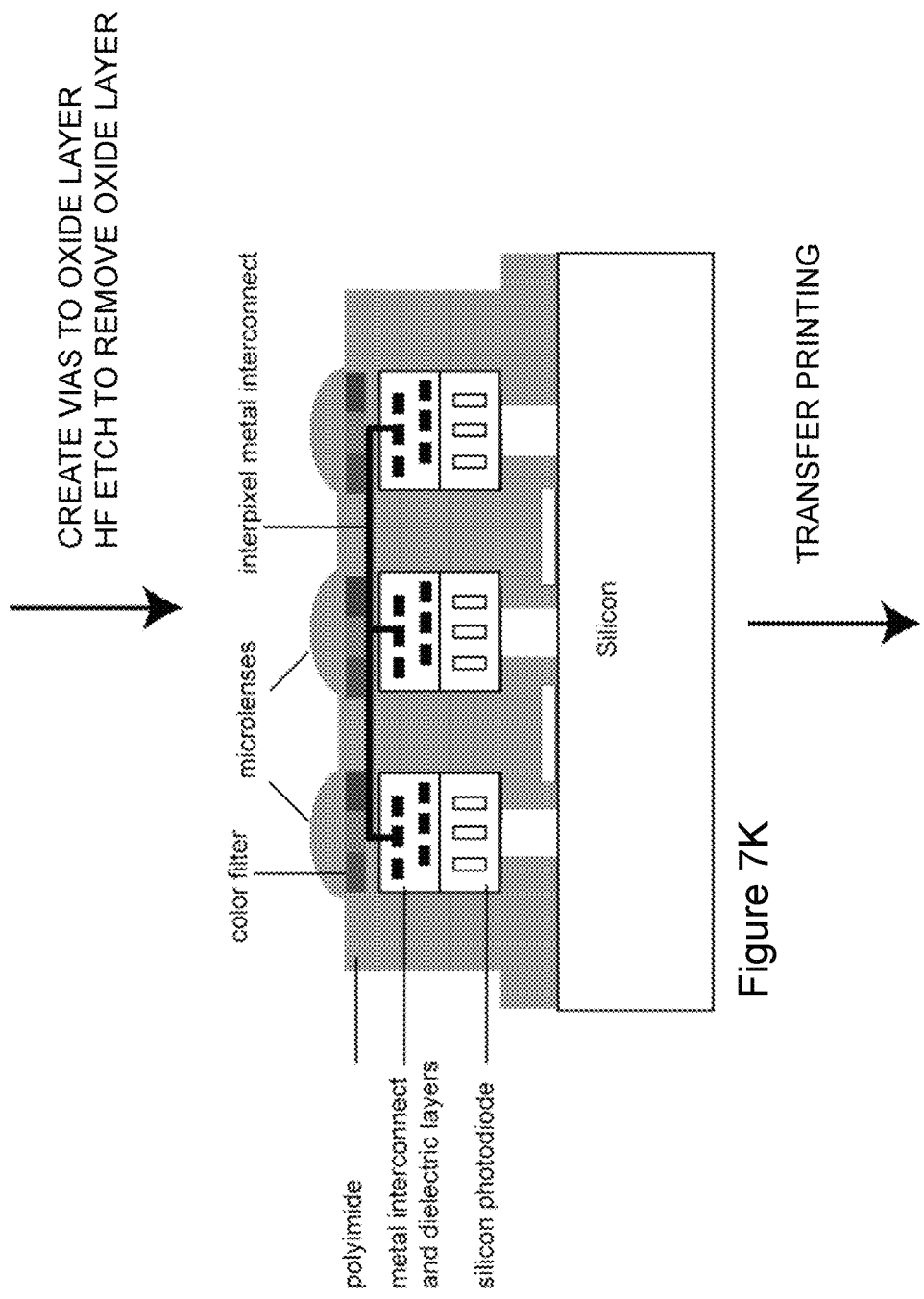

The second and third PI layers are then isolated by etching with a deposited SiO2 hard mask, in O2 RIE. PI located outside device islands and bridges is etched, as well as PI covering areas that are meant to be externally electrically interfaced, and small areas leading to the underlying oxide. Etch holes may be formed if necessary and then transferred through the silicon or metal layers by wet and or dry etching. The underlying buried oxide is etched away using HF etchant to free the devices, which remain attached to the handle substrate due to the second polyimide passivation layer which contacts the handle wafer near the border around the device islands (FIG. 7K).

If the HF etch is not controllable enough and seeps under the PI isolation layer and thereby attacks the CMOS devices, then prior to the second PI passivation a brief Argon sputtering can be done to remove any native oxide followed by amorphous silicon sputtering followed by the PI passivation and rest of the processing. After rinsing, the devices are left to air dry. The end result is a network of islands connected by metal and polymer interconnect system. These islands contain one or more pixels.

It is understood that stretchable circuits may be realized using techniques other than those described above, combinations of the techniques listed above, and minor deviations from the techniques described above. For example, stretchable circuits may be formed on plastic, elastomeric, or other stretchable materials by sputtering, chemical vapor deposition, ink jet printing, or organic material deposition combined with patterning techniques. Semiconductor materials which may be used to make circuits may include amorphous silicon, polycrystalline silicon, single-crystal silicon, conductive oxides, carbon nanotubes and organic materials. All of the methods described above for enabling stretchable circuits will henceforth be referred to as "stretchable processing".

Under-etched, ultrathin partially or fully processed circuits fabricated by one of the methods described above may be transferred from their silicon mother wafers to a desired surface via transfer printing, as described herein.

Figure 14:
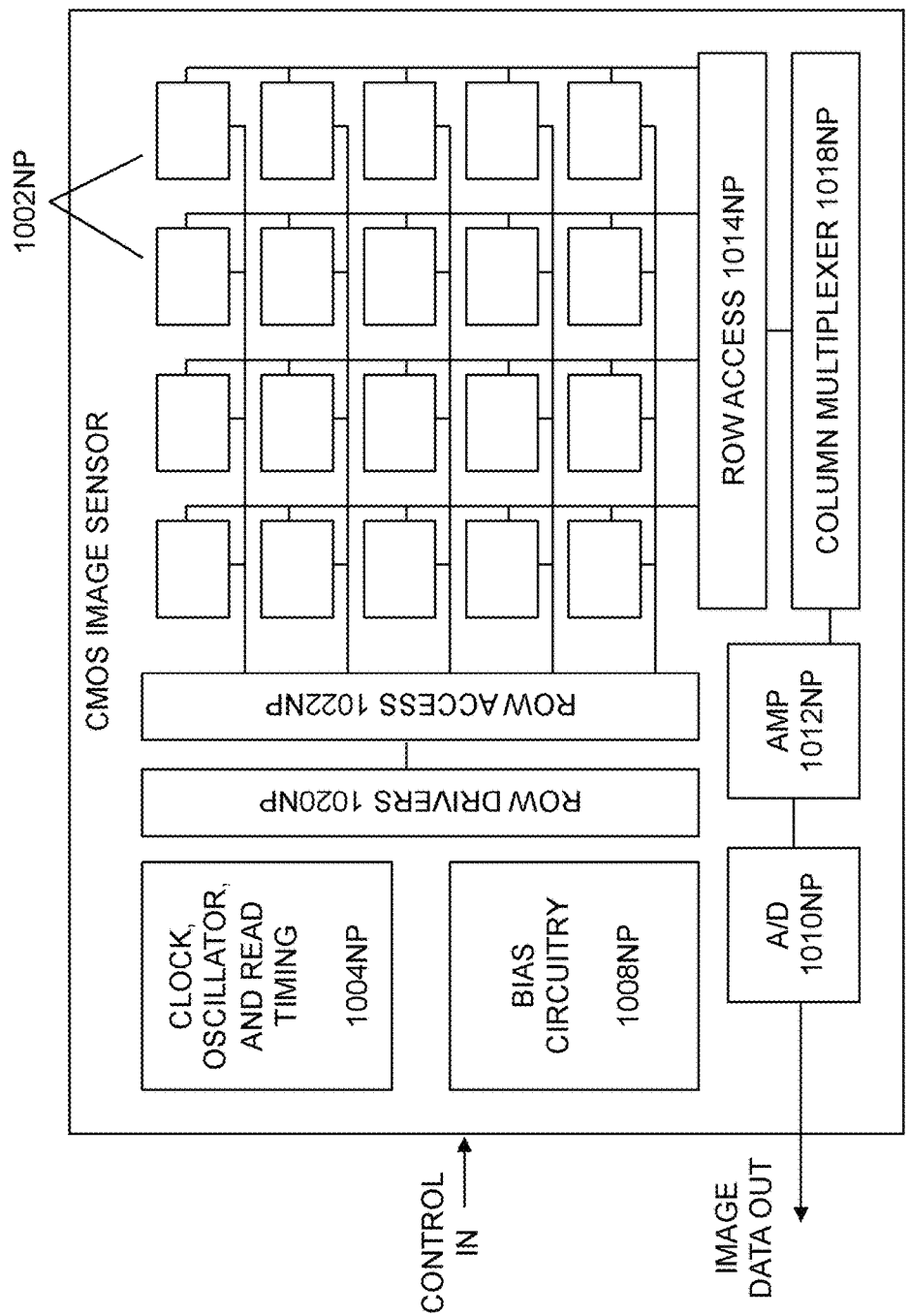
FIG. 14 is an illustration of the typical architecture of a CMOS imager.

One embodiment of the non-planar imaging array comprises a CMOS imaging system. This imaging system may be either active or passive. The components of the CMOS imaging system follows conventional CMOS imaging technology, as known to the art, where the CMOS sensor device converts an image into a digital image. The sensor usually includes a pixel array with transistors and several sensing elements, such as photodiodes. The CMOS image sensor is composed of a photo-sensing means for sensing light and a CMOS logic circuit for processing sensed light into electrical signals to make them as data, where a readout circuit is connected to each pixel cell. One method in which to create an active matrix imaging array is done by joining islands with pixel units similar to those shown in FIGS. 8 and 9. FIG. 10 illustrates how one CMOS active pixel may be connected to a series of neighboring pixels to form an array joined by interconnects which will ultimately enable stretchability and the ability of the array to conform to non-planar configurations. FIGS. 11A-C illustrates the example where there are multiple pixel units on an island connected via metal lines sandwiched between a polymer support such as polyimide. In color camera applications, color filters are required since sensors only measure light intensity. Microlenses are also used to increase the amount of light focused onto each pixel. These layers can be easily incorporated into the non planar pixel array by well known techniques. Ultimately the CMOS imaging array is incorporated into a larger system such as a camera module and would require supporting hardware to create useful information; such as illustrated in FIG. 14, including, image pixels 1002NP, timing 1004NP, bias circuitry 1008NP, A/D converter 1010NP, amplifier 1012NP, column multiplexer 1018NP, row access 1014NP, and the like.

Figure 15B:
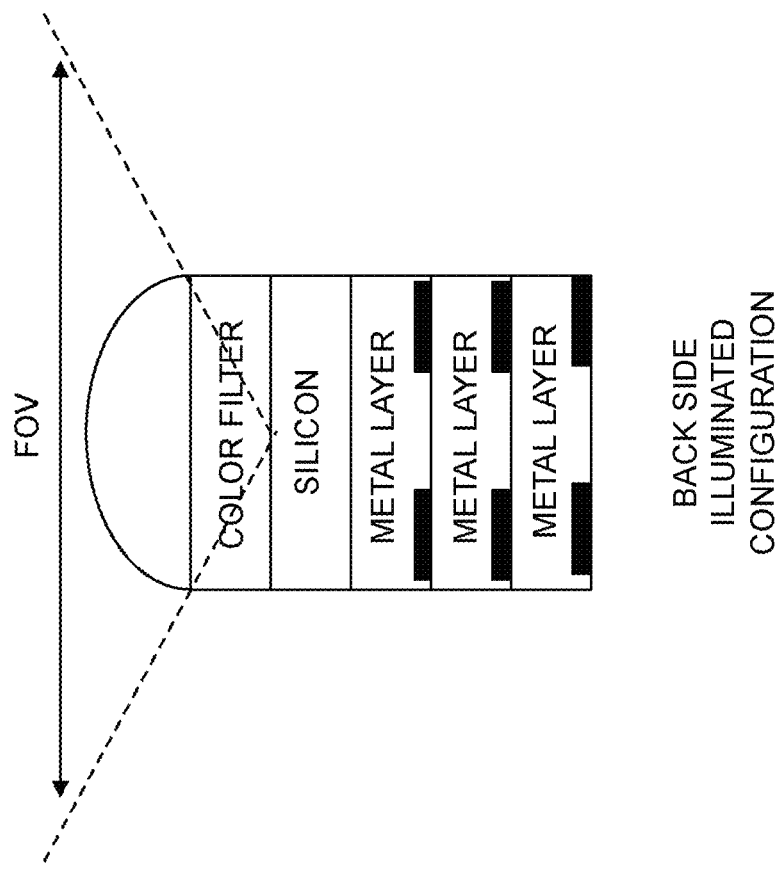
FIGS. 15A-B depict an illustration of the backside illumination concept.
Figure 15A:
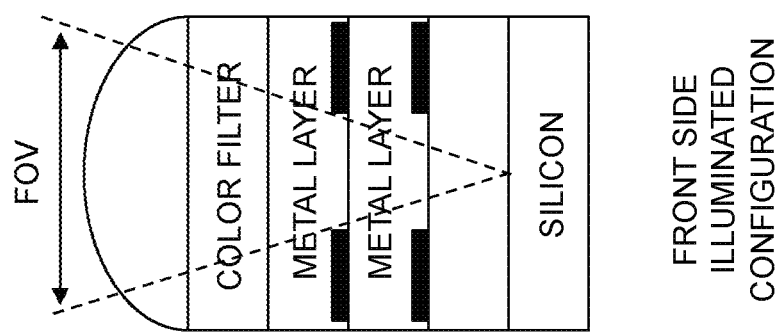

Another embodiment of the CMOS array is the backside illumination configuration. This configuration incorporates aspects of the original design but instead of having light from the image come through the metal layers, the array is flipped and light is channeled onto each pixel from behind (closer to the sensing element). This design significantly increases the amount of light that reaches a photodiode because less light is blocked by metal interconnects and dielectric layers (pixel vignetting) as occurs in conventional front side illuminated imagers as shown in FIG. 15A. This back side illuminated configuration stack design can be seen in FIG. 15B. Similar to the conventional top illuminated image sensor, the backside illuminated pixel requires a color filter in order to produce color images and benefits from having a microlens array on top of the stack to guide more light into the photosensitive parts of the imager.

The idea of backside illuminated photodetectors is not a new one. However, manufacturing these inverted detectors uncovers significant challenges with photodiode/lens/color filter alignment, pad contact forming and wafer thinning which are all required processes. The stretchable processing technique described in this invention provides a method by which some of these challenges may be overcome. It is particularly effective as an alternative to conventional wafer thinning processes which suffer from a significant reduction in sensor yield with reducing thickness. The current invention describes a method which employs undercut etching and polymer encapsulation to create thin devices and avoid the need for backside grinding of devices.

Figure 17A:
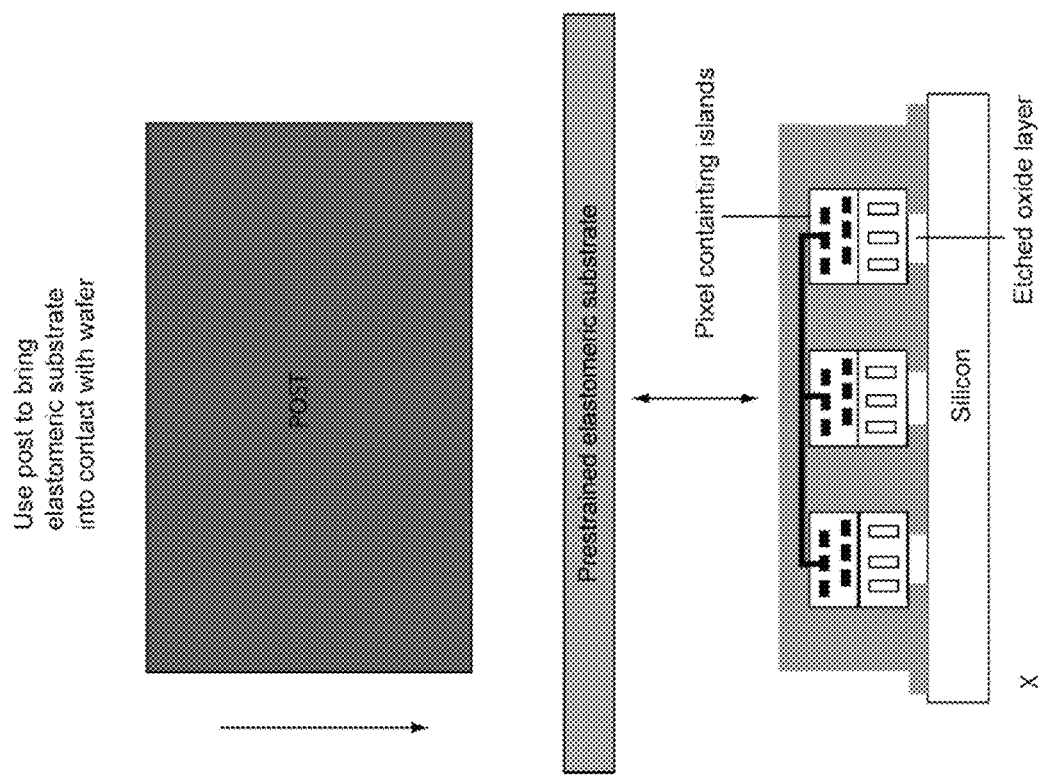
Figure 17B:
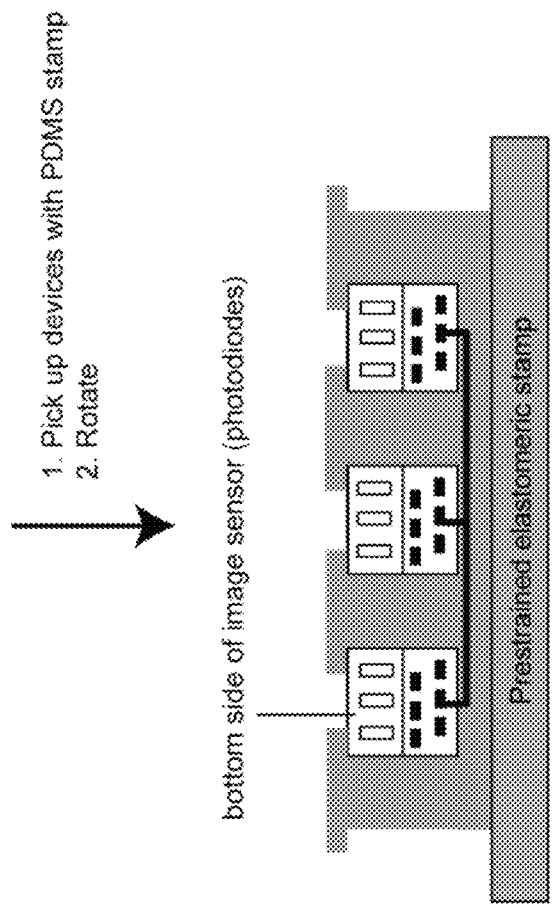
Figure 19:
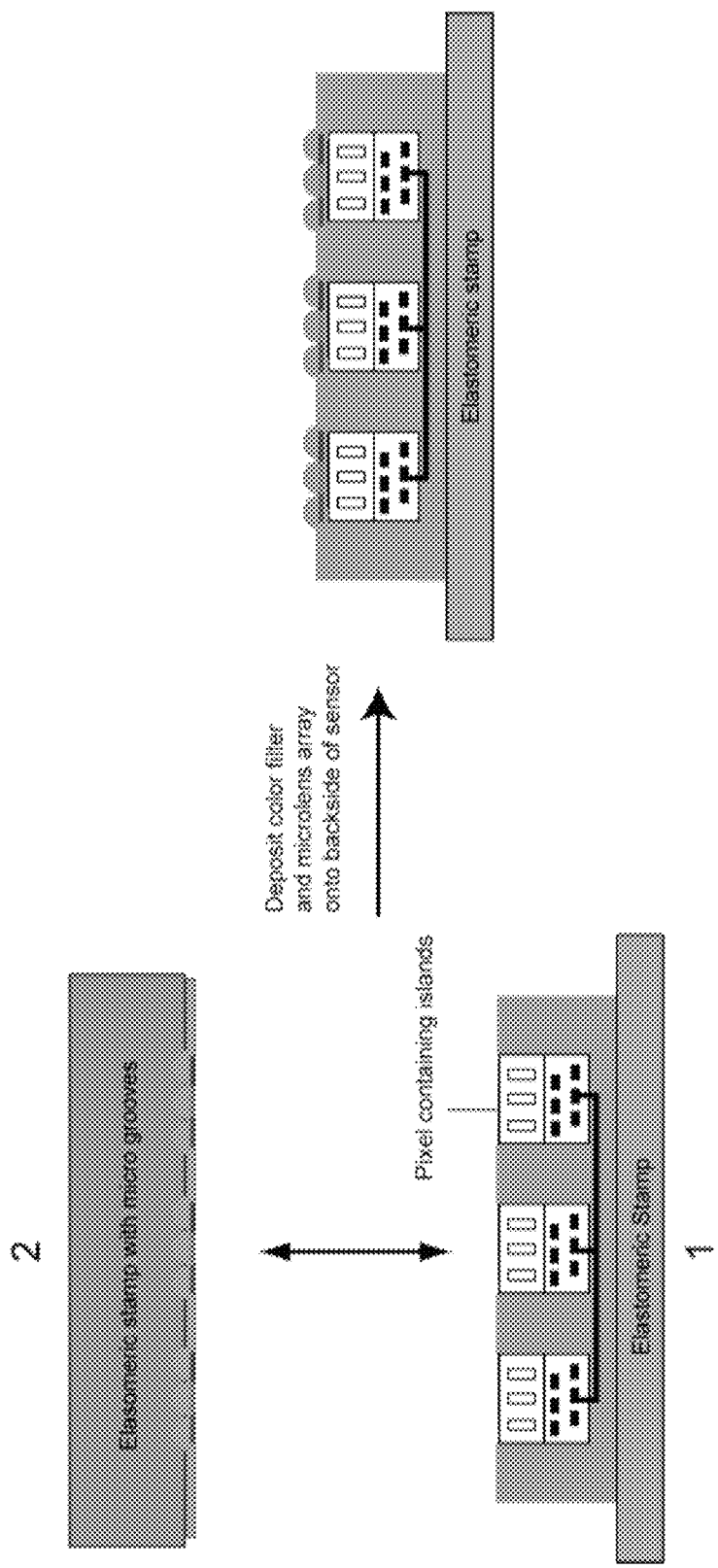
Figure 20A:
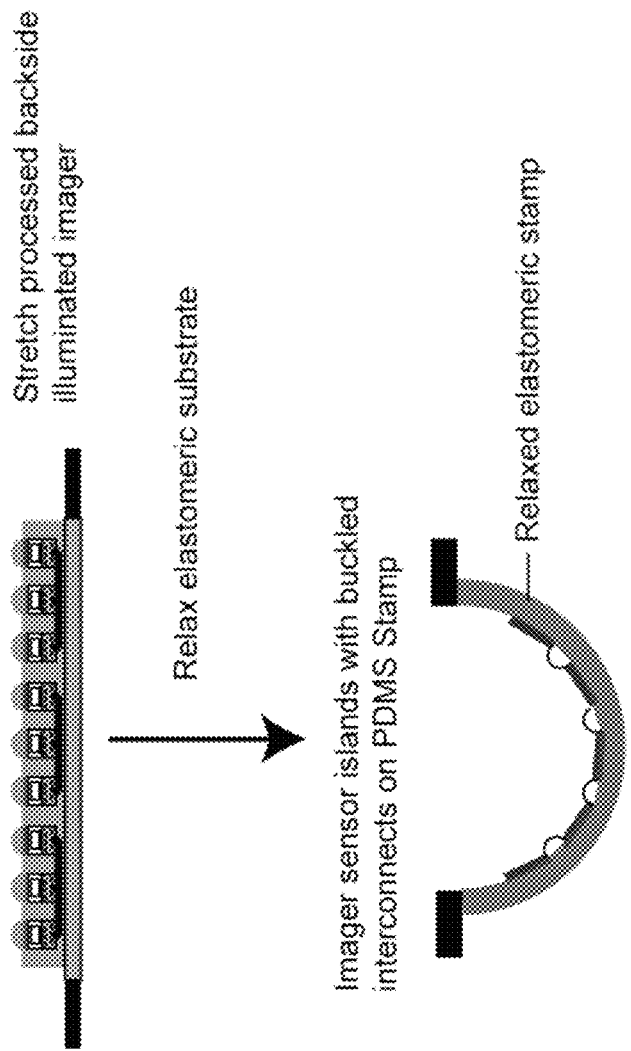
Figure 20B:
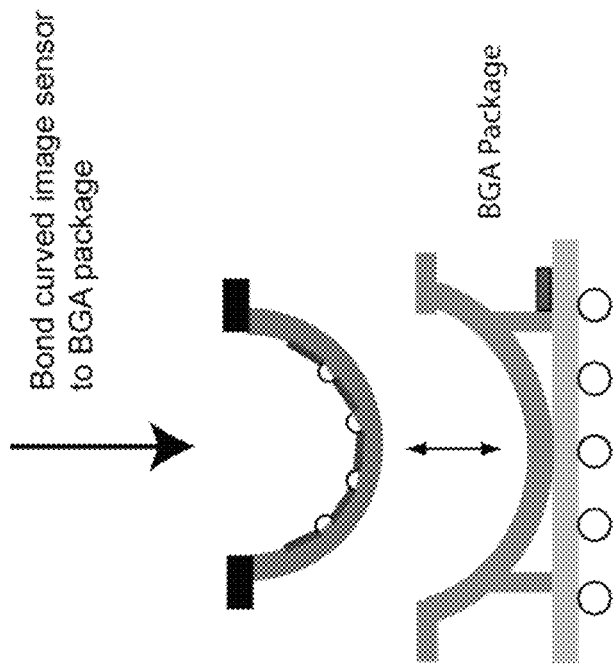
Figure 20C:
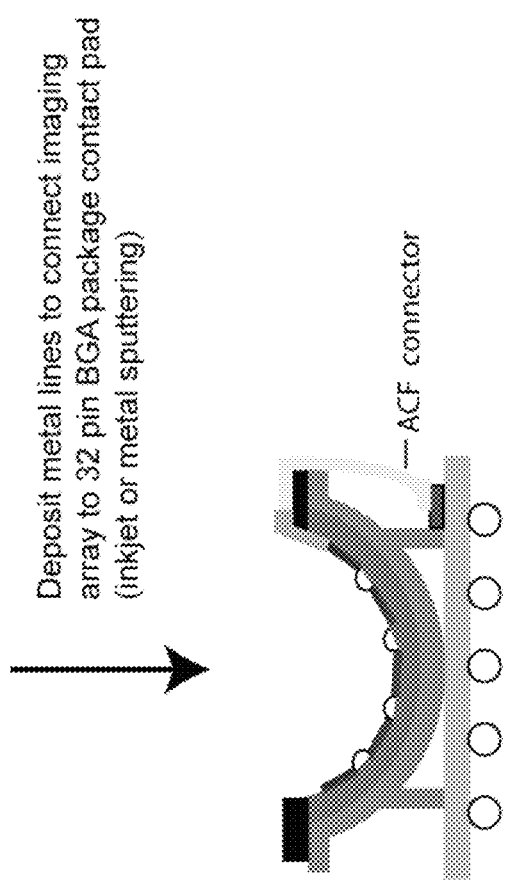
Figure 22E:
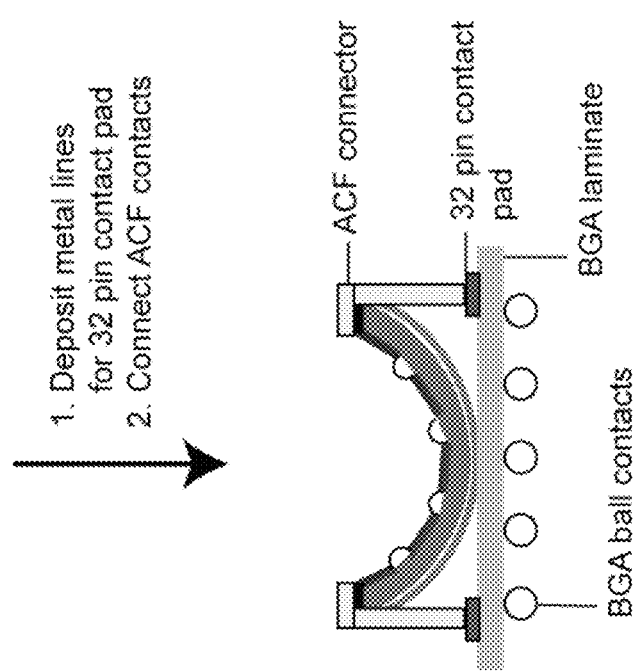
Figure 24C:
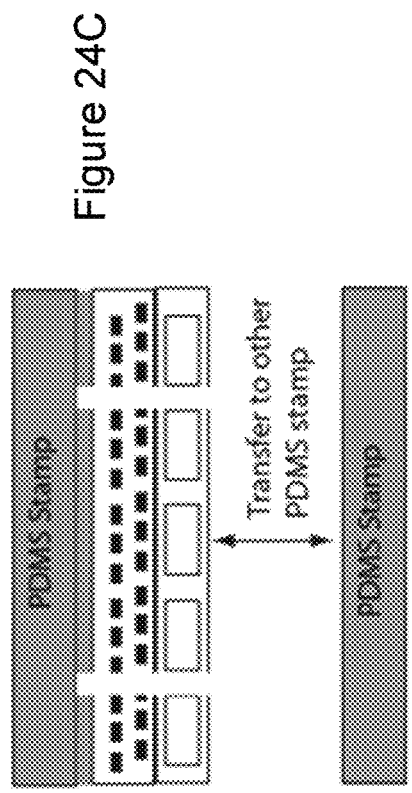
Figure 24D:
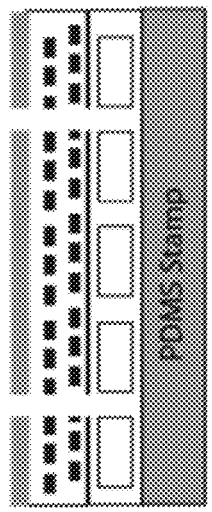

In order to create a backside illuminated imaging array, the same process may be followed for the front side illuminated array (conventional) up to the point of deposition of the inter-pixel metal interconnects as illustrated in FIG. 7G. After the deposition of the final metal layer, vias are drilled to the oxide layer and the image sensor islands are undercut. This undercut releases the islands from the mother wafer but they are supported by the PI posts that lie beneath them. The stretch processed image sensor is then flipped over using a geometric transfer stamp as shown in FIGS. 17A-B. The color filter array and a microlens array can be fabricated via conventional techniques while stacked on top of a sacrificial layer as illustrated in FIGS. 18A-F. The color filter and microlens array are aligned with the sensor array and the both are bonded together to complete the device construction as illustrated in FIG. 19. The next step involves relaxation of the geometric stamp to form the required curved shape. The curved sensor is then packaged as illustrated in FIGS. 20A-C. Other potential process flows for creating a backside illuminated imager are illustrated in FIGS. 21-23.

In embodiments, the present invention may provide for a method for fabricating a planar back-side illuminated imager. As shown in FIGS. 24A-F, the process for creating a backside illuminated imager begins with creating photodiodes on top of a sacrificial layer, supported by a rigid carrier substrate. In this example, silicon photodiodes are fabricated on an SOI wafer. Dielectric and metal lines are then fabricated on top of the photodiodes to complete fabrication of the image sensor. Conventional image sensor designs may be exploited for the previous mentioned steps. A polymeric material is then used to passivate the surface of the image sensor. This polymeric material offers mechanical support. An etch step follows, creating small holes to access the sacrificial layer (eg. SOI oxide layer). The sacrificial layer is then removed by chemical action. The image sensor array is now ready to be flipped, preferably using an elastomeric stamp. The stamp picks up the image sensor form its carrier substrate and transfers it to another stamp which completes the flip. It is subsequently deposited onto a clean second carrier substrate for further processing. At this stage, color filters and micro-lenses may be fabricated using techniques known to those familiar in the art.

The methods described herein to attain non-planar imaging arrays may be applied to numerous other imaging array/pixel designs. Commercially available CMOS imaging array designs may be modified using our stretchable processing method to give non-planar imaging array formats, such as megapixel imagers, full frame imagers, line imagers, CMOS imagers, CCD imagers, and the like. The modification involves connection of islands, each containing at least one imaging pixel, with a series of metal and polymer interconnects as described above. Connections may be made through vias which provide a means of accessing buried metal layers and joining them to an inter-pixel interconnect network which allows deformation of system.

In accordance with embodiments of the present invention, the non-planar imaging systems may be incorporated into a number of products/applications such as microscopes, semiconductor wafer inspection cameras, inspection imaging systems, metrology imaging systems, surveillance cameras, camera modules for compact cameras (cell phones, web cams, discrete security cameras), medical imagers, endoscopes, blood-flow imagers, nuclear medicine imagers, infra-red cameras and other imagers, ground based telescopes, space-based imagers, digital still cameras, video cameras, scanners, machine vision systems, vehicle navigation systems, video telephones, computer input devices, auto focus systems, star trackers, motion detection systems, image stabilization systems, pattern recognition systems, web cameras, high definition TV imagers and imaging systems for unmanned aerial vehicles (UAVs), active pixel arrays for high definition imaging, automotive cameras, night vision imagers, x-ray imagers, gamma ray imagers, radiation detectors, ultrasound imaging, thermal imaging, and the like. The embodiment of the image sensor in each application may be either in the form of a packaged image sensor, a camera module (optics component and imager) or a more complete camera (self sufficient imaging device with all software and hardware required for application specific performance).

The image sensor may be incorporated by two methods. One method involves direct incorporation of the imaging array into the camera of the desired system, thereby replacing the planar imaging array with a non-planar imaging array as described in above embodiments. This is done by depositing metal lines to connect the image sensor's bond pads to the outer rim of its supporting substrate, then bonding an anisotropic conductive film (ACF) connector from these metal lines to the receiving systems' computing modules. There may be at least one ACF connector leaving the imaging array that may be connected to a circuit for image processing. Conductive pads in the imaging array's layout are conveniently placed in easily accessible regions close to the perimeter of the array. If the pads are covered by an encapsulation layer such as PDMS they may be accessed via wet or dry chemical etching, mechanical removal of material, including but not limited to drilling, or by laser/heat ablation.

The second method for incorporating the curved sensor array into a product is to package the image sensor in a more conventional chip scale package such as ball grid array (BGA) as shown in FIGS. 16A-F and 20A-C. In accordance with the above embodiment, metal lines are created to contact the image sensor's bond pads to the outer rim of its supporting substrate. Subsequently, ACF connectors are fused to these metal lines and connected to a 32 pin contact that is linked to the BGA laminate for communication with external components. The BGA substrate typically consists of two or more insulated metal layers (copper covered bismaleimide triazine (BT) laminate). The laminate is bonded to a series of copper balls on its underside. Vias are drilled into the substrate through to the copper balls to facilitate a direct path the 32 pin contact pad and conductive balls. In order to stabilize and secure the underside of the curved image array and its ACF interconnects, a protective epoxy may be applied. The BGA form of the curved imager will be more readily acceptable into a multitude of products and may open the possibility of addressing systems not designed specifically for the uniquely shaped imagers. Other types of BGAs may be used, as well understood by one skilled in the art.

Figure 25A:
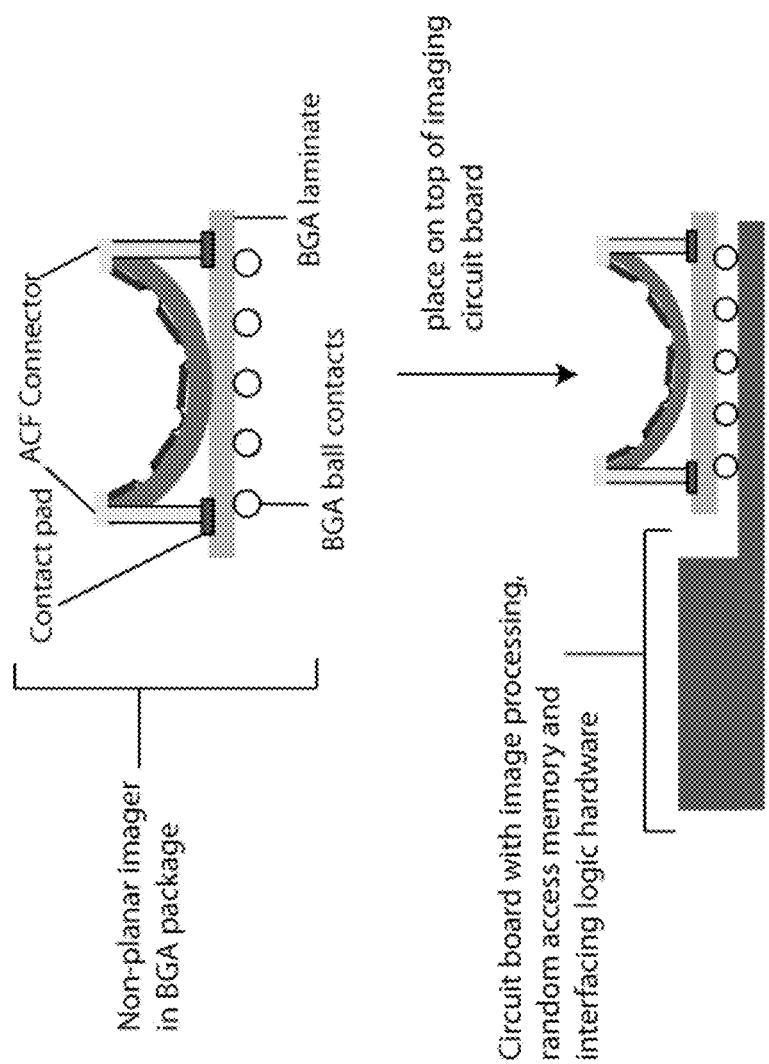

In accordance with the embodiment of the invention referring to a non-planar image sensor incorporated into a camera module as shown in FIGS. 25A-B. The packaged image sensor (e.g. BGA) is directly integrated into a circuit board which houses components including an image processing device, random access memory and interfacing logic hardware. This is done by aligning the ball contacts at the bottom of the BGA with the contacts of the circuit board then applying heat for the balls to melt and make permanent bonds.

Finally, a lens barrel containing at least one lens, is aligned with the image sensor. The lens barrel contains adjustable mounts which can change the distance between the lens(es) and the imaging array to change focus. The three components may be produced separately then assembled. The lens barrel has at least one lens on a moveable mount. This lens may be either glass or plastic. The lens is designed to be easily snapped into the moveable mount during assembly. In one embodiment the lens and its plastic holder may be extruded together.

One embodiment of the camera module has at least one injection molded plastic optic/lens which can be readily made to various curvatures and sizes before insertion into the lens barrel. A metal mold is fabricated with a hollow lens-shaped cavity that is filled by injecting polymer in a semi-liquid form. The polymer is allowed to set or cure before opening the mold and removing the part. This process is done under high pressure and the polymer lens requires little finishing work before it is set into place on the moveable mount of the lens barrel. Yet another embodiment of the camera module has a lens that can change its curvature. This is achieved by using an encapsulated liquid or gel based lens which can be put under different radial tensions, thereby changing the curvature of the lens. Changing the curvature of the lens in this manner gives a greater focusing capability to the camera module. The radial tension may be administered via the moveable mounts upon which the lens is supported.

Another embodiment of the invention relates to a non-planar imaging array that can be bent dynamically while attached to the rest of the camera module. This is achieved by encapsulating the image sensor with a thick (~1 mm) and flexible PDMS substrate. The PDMS layer enables deflections of the imager with little or no effect on the imager performance. The main purpose of such an imager is to morph for different optics heads just as a lens system is adjusted to tune the focus and magnification of an image. The varying of curvature may be performed by an actuator similar to that of the moveable mount in modulating lens curvature in the embodiment discussed above. The application of tension in the imager changes its shape and thus changes the focus of the camera module. Application of equal radial tension may be achieved using a mechanical jig which clamps onto the outer rim of the imaging array and can be expanded or contracted equally in all directions to change the curvature of the array without losing symmetry. The substrate which supports the imaging array will also have to be stretchable in this case.

One embodiment of the invention pertains specifically to ultra compact camera modules for use in cell phones, web cams and discrete security/surveillance cameras. The BGA package is commonly used for housing image sensors that are incorporated into such ultracompact systems thus making integration a very simple procedure.

There is a need to optimize the curvature of the imaging array to meet application specific requirements (e.g. different degrees of imager curvature). Standard configurations for the shape of these non-planar arrays include hemispherical, ellipsoid and paraboloids of revolution. However, the arrays may be fabricated into wider variety of symmetrical and non-symmetrical shapes as long as the system strain does not exceed its maximum capacity which was demonstrated to exceed 150%. There may also be a need to optimize the shape and number of lenses in each system. Finally, minor spatial redesign may be required when changing number or lenses and shape of imager. This modification can be considered minor and most likely would not require a significant amount of innovation.

In embodiments, the present invention may provide for improved methods for fabricating a non-planar imaging array. The advantages of a non-planar, or curved imaging arrays is well understood in the art, including a lower number of optical elements (and thus a reduction in weight, size, cost, complexity), reduced aberrations including astigmatism and coma, an increase in off-axis brightness and sharpness, an increased field of view, and the like. The present invention provides a method by which a non-planar imaging array may be fabricated utilizing image sensors made with standard semiconductor processes as described herein, such as for example, CMOS imaging elements or CCD imaging elements made from single-crystalline semiconductor. The present invention then fabricates and integrates the image sensors into a non-planar image array from stretchable electronics technologies, as described herein, allowing for the creation of an optical system that benefits from both standard high quality semiconductor processing of the image sensor, and from the advantages of non-planar imaging arrays as realized through utilization of stretchable electronics technologies. These benefits may be realized in a plurality of optical systems, such as listed herein, especially where reduced weight and size, and increased field-of-view are important, such as for example, optical systems in security systems, inspection and metrology systems, space applications, manned and unmanned vehicles, medical vision systems such as endoscopy, and the like. In addition, many other imaging applications may benefit from the lower cost/size/weight of a system fabricated by the present invention, such as for mobile devices including cell phones. The present invention may also provide benefits to more sophisticated systems, such as in telescopes, where the benefits as previously mentioned may be realized along with the ability to actuate the image surface, as in for instance, adaptive optics. One skilled in the art will appreciate that combinations of the benefits offered by the present invention can be applied across the spectrum of optical systems, and that these examples are meant to be illustrative, and not limiting in any way.

In embodiments, a medical vision system may be implemented and gain benefit from the present invention, such as for example, in endoscopy. Referring to an endoscopic imager as described herein, it can be seen that a non-planar imager mounted on an endoscope or imaging endoscopic capsule, can be implemented with the present invention. Here, the non-planar imager may be presented on the surface of the endoscope or endoscopic capsule, such as in a concave or convex configuration. A technician reading the images sent back from a procedure utilizing one of these devices may now have all the benefits provided by the present invention, including increased field of view (due in part to the curved image surface), increased image quality (due in part to the benefits of non-planar imaging and from high quality image sensors), increased performance in dim light conditions (due in part to the high quality image sensors), and the like. The non-planar imager of the present invention may enable the image array to be formed on a plurality of medical device surfaces, and still maintain a high quality image product, such as being mounted on different probes, catheters, implants, and the like. In embodiments, the present invention may provide an improvement to both the image quality and field-of-view in medical imaging devices.

In embodiments, security imaging devices may benefit from the present invention. For example, a security imaging device may have the requirements for high resolution, large field-of-view, and small size. Such a set of requirements may be better met with the present invention, such as providing high resolution through standard high quality image sensor elements, large field-of-view through a non-planar focal plane, small size through the minimizing of optics, and the like. The security camera may also benefit from the low light capabilities of standard image elements as integrated into the imaging array In embodiments, the present invention may be applied to inspection and metrology systems, where a larger field-of-view may be required while maintaining high quality and high-resolution imaging. These requirements may typically dictate that a planar imager be placed a significant distance from the objects being imaged in order to maintain field-of-view requirements, and so take up room in a facility that could otherwise be used for other functions, or without which the inspection and/or metrology system might be made smaller. However, a non-planar imager of the present invention may provide for a significantly greater field-of-view, and so the non-planar imager may allow for a shorter object distance for the same field frame. At the same time, the non-planar imager of the present invention may allow for high quality images due to the use of standard image sensor fabrication techniques. In this way, the present invention may provide for high quality images in a smaller space with shorter object distance. In an example, the present invention may provide for metrology imaging in the process of semiconductor chip manufacture. Here, the non-planar imager of the present invention may be mounted closer to the wafer and so demand less volume in which to implement the required imaging system. In addition, the non-planar imager of the present invention may be lighter due to a minimization of lenses required by the system, and so if the imager needs to be placed into motion as part of its function, it will have a lower inertia, and so the drive system requirements may be reduced. In embodiments, the present invention may provide reduced weight and increased field-of-view while maintaining high quality images to inspection and metrology applications. In addition, the reduction in lenses required of the non-planar imager may provide a system that is less costly and more reliable.

In embodiments, the present invention may provide for imaging systems for space-based imaging applications, such as for telescopes in science missions, surveillance imaging for the military, star trackers for space-based navigation, on-board telemetry imaging for spacecraft and payload state of health and operation, and the like. Spacecraft are designed with critical attention given to weight and volume of all components, and use of a non-planar imager of the present invention may provide significant advantages with respect to both of these requirements, where weight and volume are both potentially reduced with the minimization of lenses as a result of the non-planar array. At the same time, image quality need not be compromised as the present invention may allow for the use of high quality semiconductor imaging elements from standard fabrication processes. In an example, a star-tracker is typically required as a part of the spacecraft guidance and navigation system, and uses essentially a telescope to image the star field for celestial navigation. The imaging requirements for a star tracker are therefore quite high, and so the system typically requires a lens system which consumes a significant mass and volume. However, a non-planar imager of the present invention may be able to reduce the mass and volume associated with the optical system, and provide a mass and volume savings to spacecraft design resources. In embodiments, due to the potential for reducing mass and volume due to a minimized need for a lens system, the present invention may provide improved space-based imagers for spacecraft applications.

In embodiments, the present invention may provide benefits to imagers associated with manned and unmanned vehicles, such as for imagers that provide different views from the vehicle. In manned vehicles, such as cars, trucks, trains, subways, busses, boats, and the like, cameras equipped with imagers of the present invention, being potentially smaller and lighter, may be able to more easily be integrated into the vehicle to provide views from which the driver has limited or no visibility, and for unmanned vehicles may provide all or any views from the vehicle. In an example, an automotive designer may provide a non-planar imager on a back of a car, such as on the bumper, on the truck, integrated with a back light, so that the driver can have a view of what is directly behind them, such as for backing up, parking, and the like. The non-planner imager may also provide a wider field of view for the driver than would be provided by a traditional planar imaging system. In embodiments, the present invention may provide for advantages over traditional planar imagers such that cameras are easier and more convenient to install, less expensive, provide for a greater field of view, and the like.

In embodiments, the present invention may be applied to products and components that are constrained in allowable volume or which would benefit from a reduction in size. In an example, cell phone cameras are very constrained with regard to volume, as they need to produce as high a quality of image as possible in a very small volume. The lens of such a camera typically takes up a portion of that volume. However, by using a non-planar imager of the present invention, the lens system may be significantly minimized. This would not only free up the volume previously allocated to the optics system, but also reduce the cost of the phone. In another example, an image device such as a night vision scope is typically constrained to how small it can be made by the optics system. In this case, the present invention may be able to provide an imager that does not require a large optics system, and thus potentially reducing the size, weight, and cost of the device. In embodiments, the present invention may provide a way to reduce the size, weight, and cost of any imaging system that currently utilizes a planar imager and associated optics. As such, the present invention may provide general benefits to any optics system.

The application examples provided herein are meant to be illustrative of the plurality of benefits that may be enabled through the use of non-planar imagers of the present invention. As such they are not meant to be limiting in any way. Given these few examples, one skilled in the art will appreciate that the present invention may be applied to the great scope of today's optical systems, which may each benefit from all or a subset of the benefits provided from use of non-planar image arrays as described herein.

Referring now to a more detailed embodiment for endoscopic imaging applications, the imaging facility 1600 may involve endoscopic imaging devices having improved design efficiencies in terms of power and volume. As such all imaging-related embodiments described above are intended to be used with (be it additionally or alternatively) with the endoscopic imaging device, systems, and methods described below. Therefore, the specific descriptions below are meant to comprise one example of an endoscopic imaging device and shall not limit the endoscopic imaging device to those particular embodiments described below.

Embodiments of the present invention incorporate conformal, curvilinear electronic components for the purpose of volume reduction, imaging enhancement, and increased functionality.

It will be appreciated that the approach of the embodiment described below may be applied to conventional tubular endoscopy devices and capsule endoscopy devices, as well as any device utilizing the herein described curved focal plane arrays of photodetectors that are comprised in an imager, such as a CMOS, CCD, and the like imager as described herein. Note that the terms 'curved focal plane array' and 'curved optical sensor array' are used interchangeably with 'non-planar imager' as described herein. It should be noted that such curved focal plane arrays can be utilized in conjunction with any embodiment described herein and that all other embodiments described herein including those related to the circuitry including and the elements thereof are intended to be utilized as applicable in the endoscopy embodiment described below. As described herein, curved silicon optical sensor arrays have significant advantages over conventional planar arrays. These advantages include a reduced number of optical elements, reduced aberrations including astigmatism and coma, and increased off-axis brightness and sharpness.

In embodiments of the invention, an endoscopy device is fitted with a curvilinear array of sensors and/or transducers, e.g., on the exterior surface thereof, thereby reducing the required volume of the device. This approach is particularly advantageous in reducing the overall size of an endoscopy device, allowing integration of additional diagnostic and therapeutic and/or sensing functionality including any described herein and the following examples, ultrasound, pressure sensing, temperature sensing, pH, chemical sensing, targeted drug delivery, electrocautery, biopsy, laser, and heating), and increasing the allowable battery size. Increasing the power storage of a capsule endoscopy device can lead to improvements in image quality, image compression, transmission rate, number of images captured, and the intensity of illumination produced by the LEDs.

In embodiments of the invention, a capsule endoscopy device and its internal circuitry are both made flexible and/or stretchable from any of the materials described for substrates including other biocompatible materials apparent to those skilled in the art. Such a flexible/stretchable endoscopy device may have increased ease of motion along the GI tract and also increased viable volume. In other embodiments, the device may have a rigid capsule-like structure with electronics conformally fitted in the inner and/or outer shell of the capsule. The exposed surface—either a rigid ellipsoid shell or a flexible or stretchable layer—is fabricated from a material resistant to the harsh digestive environment that the endoscopy device will encounter, but which is also is biocompatible and harmless to the patient's internal anatomy. Other properties of biocompatibility of the outer surface are described herein.

The stretchable electronic components of the endoscopy device have been described herein in connection with the discussion of circuitry in all embodiments. In embodiments, circuitry comprises sensing and imaging arrays for monitoring features that are inside of bodily cavities and lumen such as the GI tract. As described above, the functionality may reside in circuitry comprising devices which may comprise device islands or vice verse. The islands house required circuitry and are interconnected mechanically and electronically via interconnects such as those described herein. The interconnects, in turn, preferentially absorb strain and thus channel destructive forces away from the device islands. They provide a mechanism by which the integrated circuits can stretch and flex when a force is applied. The device islands and interconnects may be integrated into the casing or encapsulating shell of the endoscopy device by transfer printing, as described below. Encapsulation of electronic devices and system/device interconnect integration can be performed at any of a number of stages in this process.

As with other embodiments described herein, the circuitry used in the electronic devices may comprise standard IC sensors, transducers, interconnects and computation/logic elements. In embodiments, electronic devices are typically made on a silicon-on-insulator (SOI) wafer in accordance with a circuit design implementing the desired functionality. Semiconductor devices may be processed on suitable carrier wafers which provide a top layer of ultrathin semiconductor supported by an easily removed layer (eg. PMMA). These wafers are used to fabricate flex/stretch ICs by standard processes, with particular island and interconnect placement being tailored to the requirements of a particular application. "Ultrathin" refers to devices of thin geometries that exhibit extreme levels of bendability. They are typically less than 10 μm in thickness.

The above discussions of fabrication of circuitry applies to endoscopy embodiments. However, the following discussion will describe a transfer step for embodiments related to endoscopy (but not necessarily limited thereto). In such embodiments, the circuitry is primarily used to enhance the imaging system of the device.

Imaging with a curved optical sensor array (instead of a planar array) may be used in conjunction with a lens, illuminating LEDs, battery, computing unit, antenna and a radio transmitter. Wired telemetry is used for conventional tube endoscopy. A passive or active matrix focal plane array is fabricated using one of the stretchable processing techniques described above. The array includes single-crystal silicon photo-detectors and current-blocking p-n junction diodes. Images captured using the array are minimally processed by onboard computing and transmitted (wired or wireless) to an external receiver for further processing.

The focal plane array described below could be considered part of any imaging facility described above. The individual photo detectors or elements may be networked via interconnect systems in accordance with the present invention. These devices are found on islands and are connected by interconnects such as those interconnects described herein. In embodiment, films of polyimide support certain regions and encapsulate the entire system. Such a focal plane array can thus be incorporated into the endoscopy device.

Figure 34:
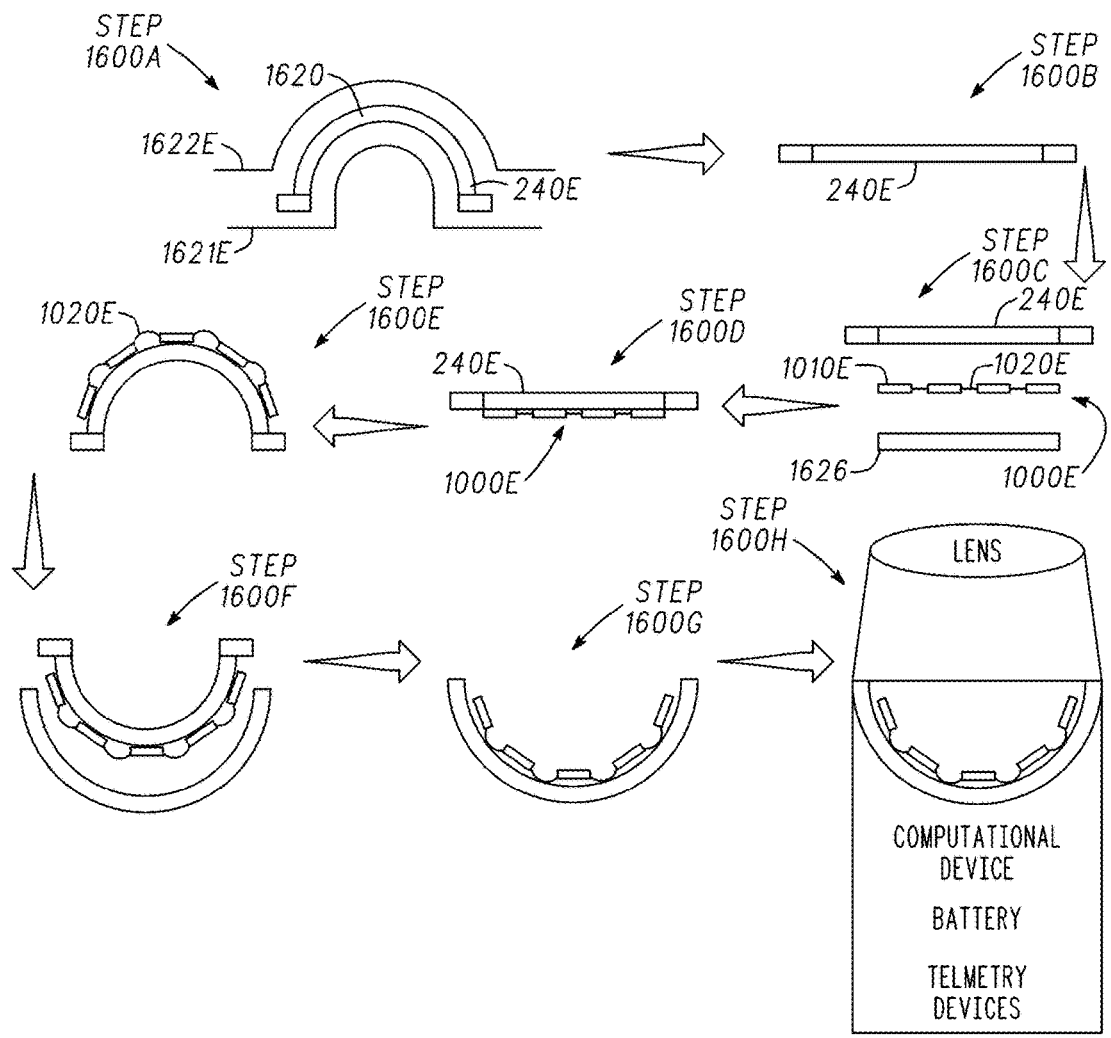
FIG. 34 depicts a process for assembling curvilinear circuitry according to an embodiment of the invention.

FIG. 34 illustrates a process of making such focal plane array. The first step is fabricating the necessary circuitry 1000E, which in this embodiment is a focal plane array, is the creation of a suitable geometric transfer stamp to facilitate this process. In this embodiment, the circuitry is represented herein as 1000E (although it should be understood that is contemplated that this circuitry 1000E relates to and may be used with other circuitry embodiments described herein).

At Step 1600A, an appropriate stamp (also referred to as transfer element) 240E is created by casting and curing poly(dimethylsiloxane) (PDMS) in the gap between opposing convex and concave lenses with matching radii of curvature (1621E and 1622E respectively). The radius of curvature should reflect the optimal parabolic curvature useful for a non-coplanar imager. At step 1600B, the cured curved transfer element 240E (the removal of which from lenses stamping mechanism not shown) can be stretched using a specially designed mechanism which provides outward radial forces (in embodiments equal outward forces) along the rim of the stamp to create the planar pre-strained geometric transfer element. The transfer element should return to its initial size when relaxed. Transfer element 240E should also be large enough in its planar configuration to contact the entire area of electronic device islands on the donor substrate.

A component of the circuitry 1000E in this embodiment is the processed electronic devices joined by interconnects 1020E. At step 1600C, the circuitry 1000E is brought into contact with the planar transfer element 240E, which adheres to the former via sufficiently strong van der Waals interactions. The transfer element 240E is peeled back, thereby removing the focal plane array, i.e., circuitry 1000E, from its handle wafer 1626, shown at 1600D. After the focal plane array 1000E is removed from the handle wafer, the tension in the stamp is released and the contacting layers, i.e., the focal plane array and the stamp, both take initial geometric form of the stamp (shown at 1600E). The focal plane array 1000E compresses and the networked interconnects 1020E of the array buckle to accommodate the strain. The buckled focal plane array 1000E is then transferred to its final substrate (shown in steps 1600F-H) which has a matching radius of curvature and is also in communication with the battery, antenna and a radio transmitter via electrical contacts. This transfer occurs by contacting both surfaces and is aided by the use of a photocurable adhesive. The adhesive provides sufficient attraction such that when the PDMS stamp is removed, it releases the curvilinear array of photodetectors onto the imaging system port. The curved focal plane array is then connected to the rest of the imaging electronic components via electrode contact pads on the outer perimeter of the array.

Figure 34A:
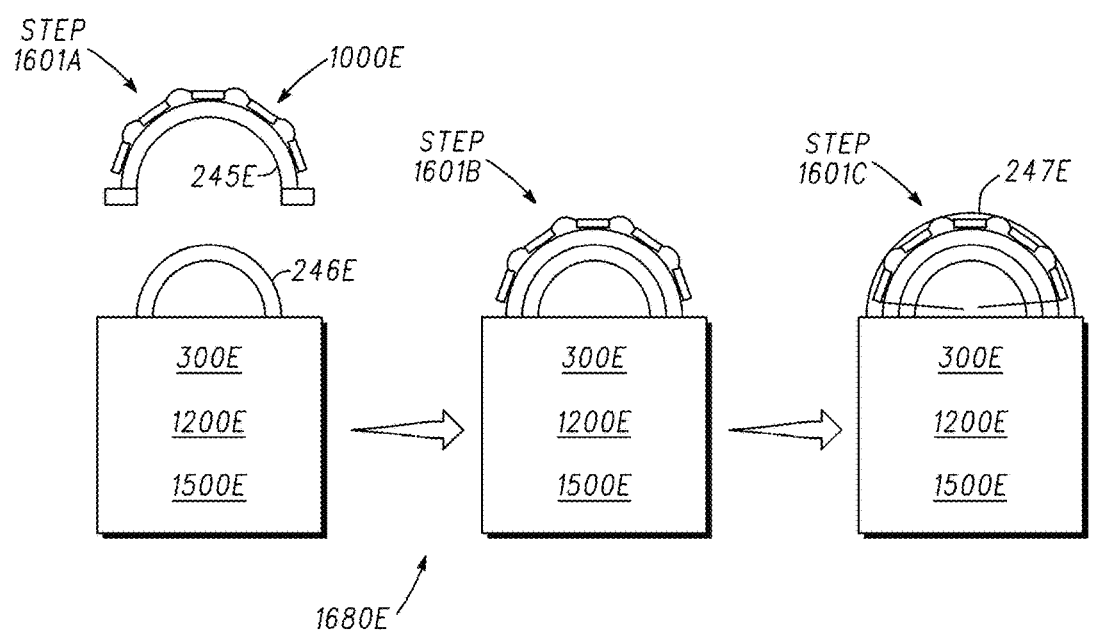
FIGS. 34A and 34B depicts the process for applying a curvilinear array of circuitry to an endoscopic device according to an embodiment of the invention.

In another embodiment shown in FIG. 34A, and endoscopy device 1680E comprising power 300E in the form of a battery, processing facility 1200E, and data transmission facility 1500E is shown. Step 1601A shows convex focal plane array 1000E that is adhered to the outer shell of the endoscopy device 1680E by, for example, a geometric transfer stamp 245E. After lifting the focal plane array off the handle wafer with the planar pre-strained PDMS (as described in connection with previous FIG. 34), it can be relaxed and directly deposited onto the distal end of the endoscopy device 1680E, which is provided with a receiving substrate 246E having, for example, a photocurable adhesive. After deposition onto the endoscopy device 1680E (status shown as 1601B), electrical contacts are made from the array 1000E to the internal circuitry of the endoscopy device 1680E. At 1601C, all of the exposed circuitry can be sealed with a suitable polymer and/or metal layer (eg. parylene, polyurethane, platinum, gold) 247E.

Micro-lens arrays may be required for such optical array systems. However, with proper illumination and negligible distance between the optical array and the surface being imaged (e.g. near field imaging), this requirement may be nullified.

In yet another embodiment, a focal plane array, also referred to as circuitry 1000E (as described above) is conformally wrapped around an endoscopy device such that it points in an outward radial direction from the long axis of the device. This is achieved by completing the same planar stretchable processing steps mentioned above and transferring the circuit with a different specialized polymeric stamp. The transfer stamp may take the form of a planar rectangular strip. Each polymeric strip is pre-strained by thermal expansion (heat to around 160° C.) or by applying uniform radial strain. This pre-strained polymer is then positioned in direct contact with the processed focal array. The elastomer is subsequently peeled back to release the array from its handle wafer. The stamp is then relaxed via cooling to room temperature or gradual release of the mechanically induced strain. Release of this strain causes the elastomer to return to its initial shape, which in turn forces the device islands of the array to draw closer. In embodiments, the interconnects are forced to buckle, enabling stretching and bending characteristics. In embodiments, the area upon which the array is meant to adhere is pre-treated with a photo-curable adhesive. Alternatively, a layer of PDMS may be used to enhance adhesion.

Figure 34B:
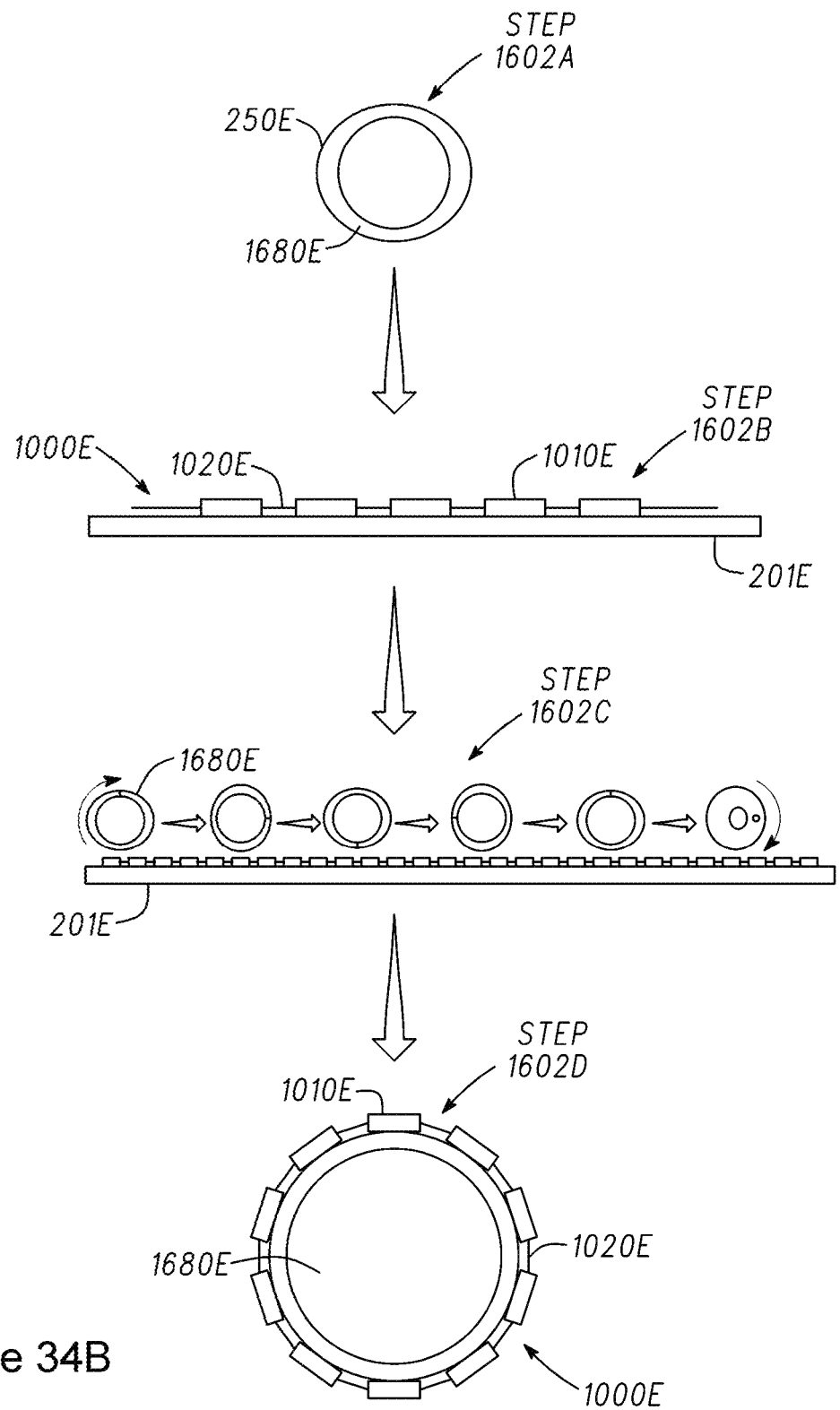

FIG. 34B details an embodiment of the process for transferring circuitry to the endoscopy device. The transfer is achieved by stamping the planar array of device islands and interconnects onto a curvilinear surface such as an endoscopic device 1680E. 1602A shows the endoscopy device having a thin PDMS shell or adhesive outer layer 250E. 1602B shows the circuitry 1000E on a carrier substrate 201E. 1602C shows the step of rotating the endoscopic device 1680E around a single revolution over the substrate 201E containing planar array of device islands, the array of photodetectors and interconnects will preferentially adhere to the surface of the endoscopy device 1680E in a curvilinear manner as shown in Step 1602D.

In another embodiment, micro-lens arrays may be required for optimal focusing and image quality. However, with proper illumination and negligible distance between the optical array and the surface being imaged, this requirement may be nullified. In the case where micro-lens arrays are required, they may be created directly as the encapsulating layer of the photodetector arrays during stretchable processing. They may also be stamped on after the endoscopic devices are made. This optical array is then encapsulated and electronically integrated with the rest of the endoscopic device in the following manner: electronic devices which have been processed for stretching, can be picked up with a planar pre-strained PDMS stamp. The pre-strained PDMS stamp is then relaxed and brought into contact with the acceptor substrate for transfer printing. This acceptor surface may be the surface of the endoscopy device, said surface coated with a thin PDMS layer, or a separate thin appropriately shaped PDMS layer that may later be wrapped around the endoscope. In the case where the devices are facing outwards on the endoscopy device substrate, they may be encapsulated (while in their compressed state) with another layer of PDMS, or a liquid layer of PDMS followed by an upper layer of solid PDMS to make a fluid encapsulation. Other materials/methods may also be applied. In the case where the devices are facing outwards on the endoscopy device substrate, they may be electrically externally interfaced at conductive pads that should be designed to be located at a convenient location. Anisotropic conductive film (ACF) connectors can be used to interface to these conductive pads, by pressing and heating the film onto the pads.

In the case where the devices are fully encapsulated or facing inwards, they may be electrically externally interfaced by first removing part of the encapsulating polymer over the conductive pads through wet or dry chemical etching, or physical mechanical removal of material, including but not limited to drilling. At this point, the ACF may be incorporated. Alternatively, the stretchable electronics may be electrically interfaced to an ACF prior to the transfer or encapsulation process.

Figure 35:
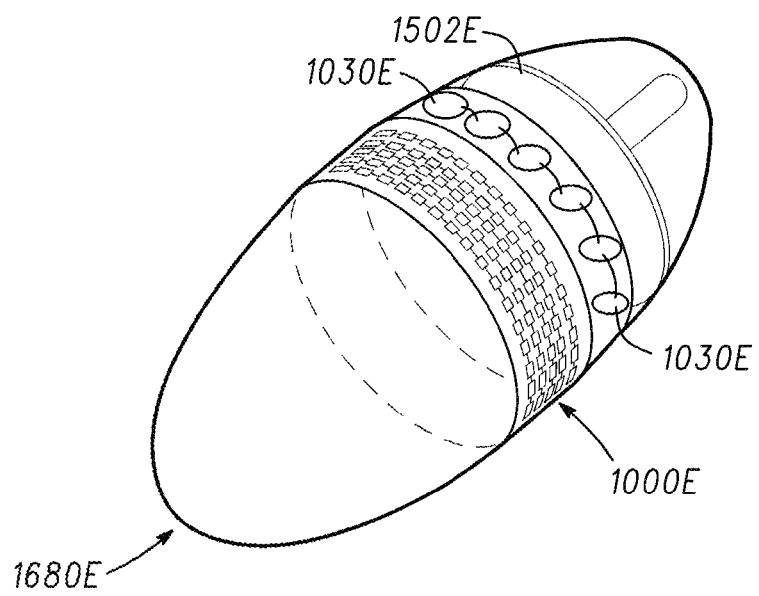
FIG. 35 depicts an embodiment of an endoscopic device according to the present invention.

In embodiments, circuitry 1000E may include a flexible LED array on the outer surface of the endoscopy device 1680E, as shown in FIG. 35. Such an array provides illumination required for optical image capture. A representative process for creating a flexible LED system is as follows:

LEDs are made from quantum well (QW) structures on a GaAs substrate. In between the GaAs substrate and the QW structure is an AlAs sacrificial layer. The QW structure is etched with reactive ion etching (ME) to down to the sacrificial layer to form isolated square islands which may be in the range of, for example, 10-1000 μm on an edge. A partial release/undercut of the islands with HF etching is performed. Photoresist is spun onto the substrate and patterned to form squares around the corners of the islands, to serve as anchors. A full HF release etch is performed to free the islands from the GaAs bulk substrate; the photoresist anchors prevent the islands from floating away during etch, rinse and dry steps. An elastomeric stamp (for example PDMS) is used to pick up the islands and transfer them to another substrate. The transfer may be done in multiple steps, picking up a fraction of the GaAs islands at a time, to rearrange them geometrically. The substrate onto which the islands are transferred for further processing may be a layer of PET (polyethylene plastic) on a glass substrate that can be later peeled off, or a layer of polyimide on top of a PMMA (polymethylmethacrylate) sacrificial layer, or a layer of PDMS etc. Parts of the LED islands are then patterned and wet etched so that the bottom n-type contact is exposed; this may be done with, for example, a H3PO4+H2O2 combination. Parts of the islands are unetched so that the upper p-type material can be contacted electrically as well. Next, a planarization layer of polyimide is spun on, patterned so that vias extend down to the p and n type contact regions of the device. Thin film wires are deposited and patterned such that the wires to the p-type regions run in one direction, and the wires to the n-type regions run in an orthogonal direction. One of the other wires should have a gap so as not to cross-circuit. This gap is bridged by spinning another planarization layer thereover and patterning it with vias to each side of the gap, and metal is patterned over the planarization layer to make the connection. Another passivation layer is spun on top, and the entire stack is etched so that the bridges and islands remain encapsulated with polymer but the intervening areas are completely etched away. This allows the bridges to be flexible. The PMMA sacrificial layer is undercut, or the PET layer is peeled off, and the entire sheet with circuits may be picked up again by PDMS stamp, and flipped over. The backside of the lower polyimide, or bottom of the circuits, is coated with Cr/SiO2; coating of the bridges is avoided by using a shadow mask evaporation procedure. The samples are subjected to a UV ozone treatment to impart dangling bonds to the SiO2, facilitating formation of covalent bonds with the next substrate to which the circuits are transferred. This final substrate may be thermally or mechanically pre-strained PDMS, such that after transfer, the strain is relaxed and the devices move closer together and the bridges pop up and buckle to accommodate the strain.

The stretchable LED array is transferred to the endoscopy device in a manner similar to that of the cylindrical optical sensor array. It is then encapsulated and integrated at the device level according to the methods described herein in connection with the micro-lens array. FIG. 35 shows an endoscopy device 1680E wherein circuitry 1000E comprises and array of photodetector and array of LED's (individually shown as 1030E. The LED array may utilize processing 1200E in the form of a logic device so that it only illuminates areas of interest during the operation and can be turned off when not in use as a power-saving mechanism. Device also includes a data transmission facility which includes RF antenna 1502 to wireless communicate with external devices.

In another embodiment of the present invention, the endoscopy device is equipped with an array of sensors which can be selected from those herein including those in connection with the discussion of 1100. Said sensors working in conjunction with circuitry 1000E to monitor pH, the presence of chemicals, and/or enzyme activity. IN embodiments, the data collected by this sensor array is processed by local computing devices and transmitted via RF antenna or wired telemetry to an external receiver for further analysis.

At least some of the sensors in the array may comprise an ion-sensitive field effect transistor (ISLET), which generate data relating to changes in ion concentration. The output signals are typically a voltage and/or current difference, the magnitude of which varies with the change of sensed ion (eg. hydronium) and/or enzyme. Other types of chemical sensors may be also or alternatively be utilized.

Another embodiment of the present invention relates to a capsule endoscopy device with a plurality of electronic components conformally fitted to the inside and/or outside walls of the capsule shell in order to conserve space. Conformal components are created by first performing stretchable processing on suitable materials as described herein. The basic components of such an endoscopy device include a passive or active matrix focal plane array, lens, illuminating LEDs, battery and telemetry devices (antenna and a radio transmitter). Optional components may include sensors described herein including ultrasound transducers, pressure sensors (eg. silicon-based devices utilizing piezo-resistive or capacitive sensing mechanism, polymer-based sensors, and/or optically based sensors that measure physical deflections), temperature sensors (eg. silicon band-gap temperature sensors, Pt resistance temperature devices), Ph/enzymatic/chemical sensors (eg. Islets, as discussed above), targeted drug delivery components, electrocautery devices, biopsy devices, lasers, and heating devices. Components that benefit from contact with the GI wall and fluids (eg. chemical sensors, LED, optical arrays) are situated in such a manner as to communicate fluidly or optically with the outer environment. This may be accomplished, for example, by placing the devices conformally on the outer surface of the capsule or through the use of electrodes which relay information from the outer region to the inside of the capsule. The remaining components (e.g. battery, telemetry devices) are preferably located on the inside of the capsule.

Methods for creating stretchable focal plane arrays and incorporating them into a desired substrate are described above. The same methods used to process and transfer focal plane arrays (stretchable processing) may be employed for various single-crystal silicon based electronic devices (e.g. antenna, RF transmitter, ISFET), with circuits being laid out (eg. using CAD tools) in a manner that accommodates mechanical deformation and stretching.

In embodiments where it is desired to incorporate heterogeneous integrated circuits (non-silicon based devices), a slightly different approach may be employed. When creating a device that requires heterogeneous integration (e.g. LEDs), circuits are typically created on different substrates. After stretchable processing, the electronic devices are combined onto the same substrate using stamping methods previously described. This substrate may be the final destination of the devices (product integration) or may instead be intermediate (i.e. A rigid, flexible or stretchable material which will be incorporated into the product at a later time). At this point interconnects may be required to keep all of the heterogeneous components in electrical communication. These may be provided using soft lithography or another low-impact, low-temperature-processing (<400° C.) method with accurate alignment (<5 µm). The integrated circuit is then appropriately encapsulated and system/device interconnect integration can be executed as described above in connection with the micro-lens array.

As mentioned above, materials for the substrate used in the embodiments herein may be biocompatible. Such is the case with substrates including outer coatings of endoscopy device. In addition to biocompatibility, any part of the device housing that comes between the imager array and the object being monitored is preferably transparent. Further, the material in the outer shell of the endoscopy device facilitates easy travel through the GI tract. Examples of suitable biocompatible materials are given above.

It is to be understood that the housing of the device described above may also be the substrate and vice verse. Therefore, the skilled artisan will appreciate that certain discussions related to the substrate's material may—in certain embodiments—be understood as to apply to said housing.

Figure 26:
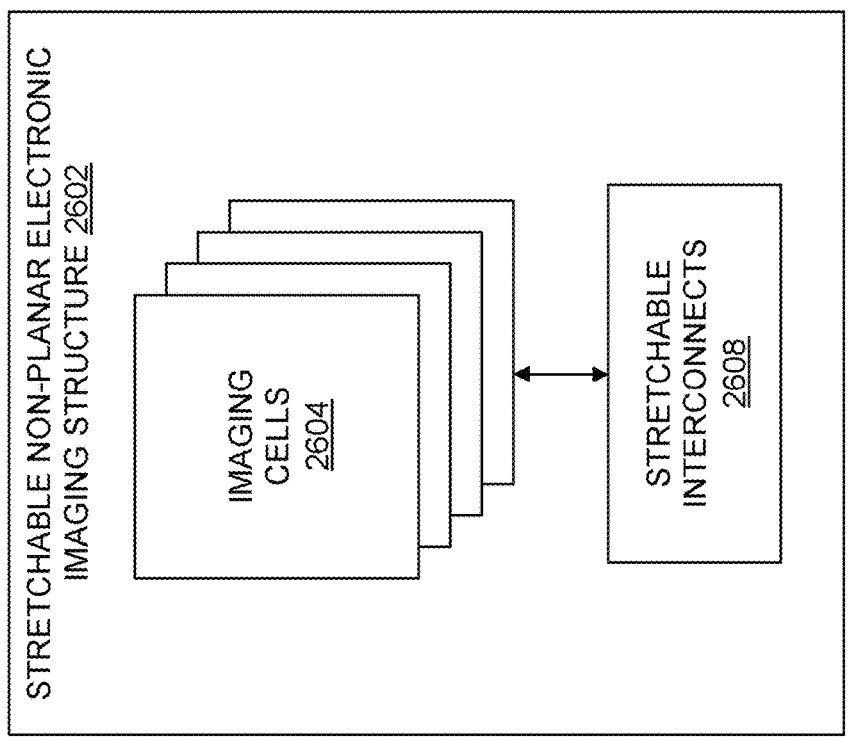
FIG. 26 depicts an embodiment for a stretchable interconnect non-planar electronic structure.

Referring to FIG. 26, in embodiments the present invention may provide for an imaging array structure, comprising a stretchable non-planar electronic imaging structure 2602, where the structure includes semiconductor imaging cells 2604 electrically interconnected with stretchable interconnections 2608. The semiconductor may be a single-crystalline semiconductor. The semiconductor may be a non-single crystal silicon material used for photo-detection, such as an amorphous silicon material, polycrystalline silicon material, single-crystal silicon material, conductive oxide material, organic material, carbon nano-tube material, and the like. The semiconductor imaging cells may include at least one imaging pixel and support electronics for controlling and reading out the image from the at least one imaging pixel. Light may impinge the front-side of the imaging cells as provided in the non-planar electronic imaging structure. Light may impinge the back-side of the imaging cells as provided in the non-planar electronic imaging structure, where the imaging cells have at least one of color filters and micro-lenses transfer printed onto the backside of the imaging cells. The imaging structure may be actuated, such as to change the curvature of the imaging structure. A curved imaging system imager packaging may be provided, such as a chip scale packaging, a ball grid array, and the like. The fabrication of the imaging cells may be on at least one of a silicon-on-insulator (SOI) and a rigid stack, where the fabrication structure may be a layered order of Silicon, then Polymethyl Methacrylate (PMMA), then polyimide (PI), then Silicon. The imaging cells include color filters, such as to provide for color image capabilities. The imaging cells may include micro-lenses, such as to provide for enhanced image quality. The imaging cells may be arranged as sensor islands, such as comprised of one pixel per sensor island, or more than one pixel per sensor island. The imaging array may be shaped in symmetrical non-planar geometry, such as a paraboloid of revolution, a hemisphere, an ellipsoid, and the like. The imaging array structure may be used to create a camera module, such as including a lens barrel with at least one lens on a moveable mount, and a circuit for image processing and transmission. The camera module may include a lens, such as a plastic molded lens. The lens shape may be changed via the application of a force, such as a radial tension force, a radial compression force, and the like. The imaging array may be actuated, such as to change the curvature of the imaging structure.

Figure 27:
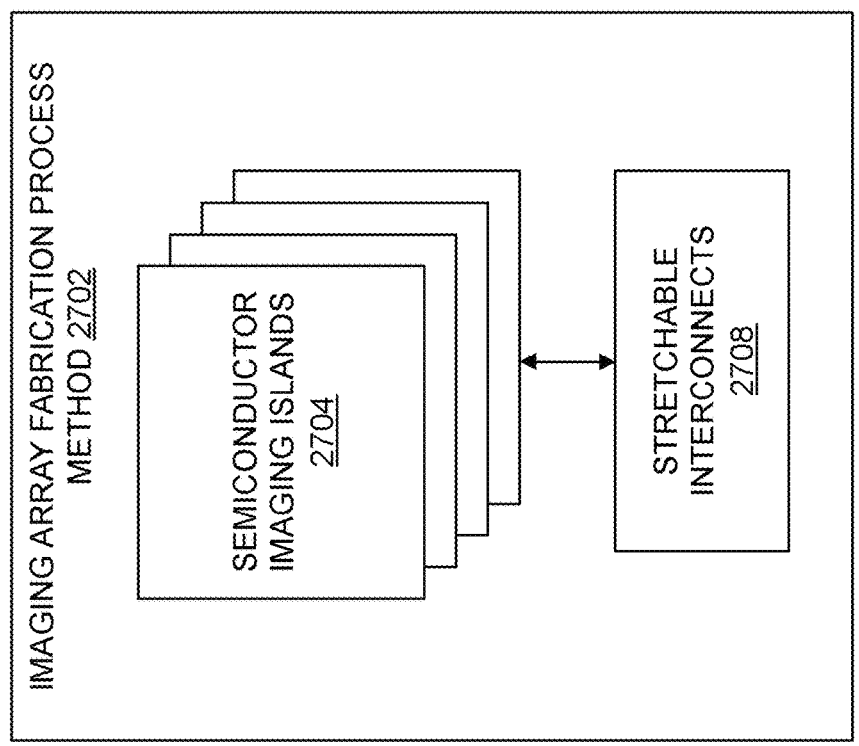
FIG. 27 depicts an embodiment for a stretchable non-planar electronic imaging device fabrication process using interconnected islands of semiconductor elements.

Referring to FIG. 27, in embodiments the present invention may provide for an imaging array fabrication process 2702 method, comprising fabricating an array of semiconductor imaging islands 2704 from a single-crystal semiconductor substrate, and interconnecting the imaging islands with stretchable interconnections 2708. The semiconductor imaging islands may include at least one imaging pixel and support electronics for controlling and reading out the image from the at least one imaging pixel. The semiconductor may be a single-crystalline semiconductor. The semiconductor may be a non-single crystal silicon material used for photo-detection, such as an amorphous silicon material, polycrystalline silicon material, single-crystal silicon material, conductive oxide material, organic material, carbon nano-tube material, and the like. The semiconductor imaging cells may include at least one imaging pixel and support electronics for controlling and reading out the image from the at least one imaging pixel. Light may impinge the front-side of the imaging cells as provided in the non-planar electronic imaging structure. Light may impinge the back-side of the imaging cells as provided in the non-planar electronic imaging structure, where the imaging cells have at least one of color filters and micro-lenses transfer printed onto the backside of the imaging cells. The imaging structure may be actuated, such as to change the curvature of the imaging structure. A curved imaging system imager packaging may be provided, such as a chip scale packaging, a ball grid array, and the like. The fabrication of the imaging cells may be on at least one of a silicon-on-insulator (SOI) and a rigid stack, where the fabrication structure may be a layered order of Silicon, then Polymethyl Methacrylate (PMMA), then polyimide (PI), then Silicon. The imaging cells include color filters, such as to provide for color image capabilities. The imaging cells may include micro-lenses, such as to provide for enhanced image quality. The imaging cells may be arranged as sensor islands, such as comprised of one pixel per sensor island, or more than one pixel per sensor island. The imaging array may be shaped in symmetrical non-planar geometry, such as a paraboloid of revolution, a hemisphere, an ellipsoid, and the like. The imaging array structure may be used to create a camera module, such as including a lens barrel with at least one lens on a moveable mount, and a circuit for image processing and transmission. The camera module may include a lens, such as a plastic molded lens. The lens shape may be changed via the application of a force, such as a radial tension force, a radial compression force, and the like. The imaging array may be actuated, such as to change the curvature of the imaging structure.

Figure 28:
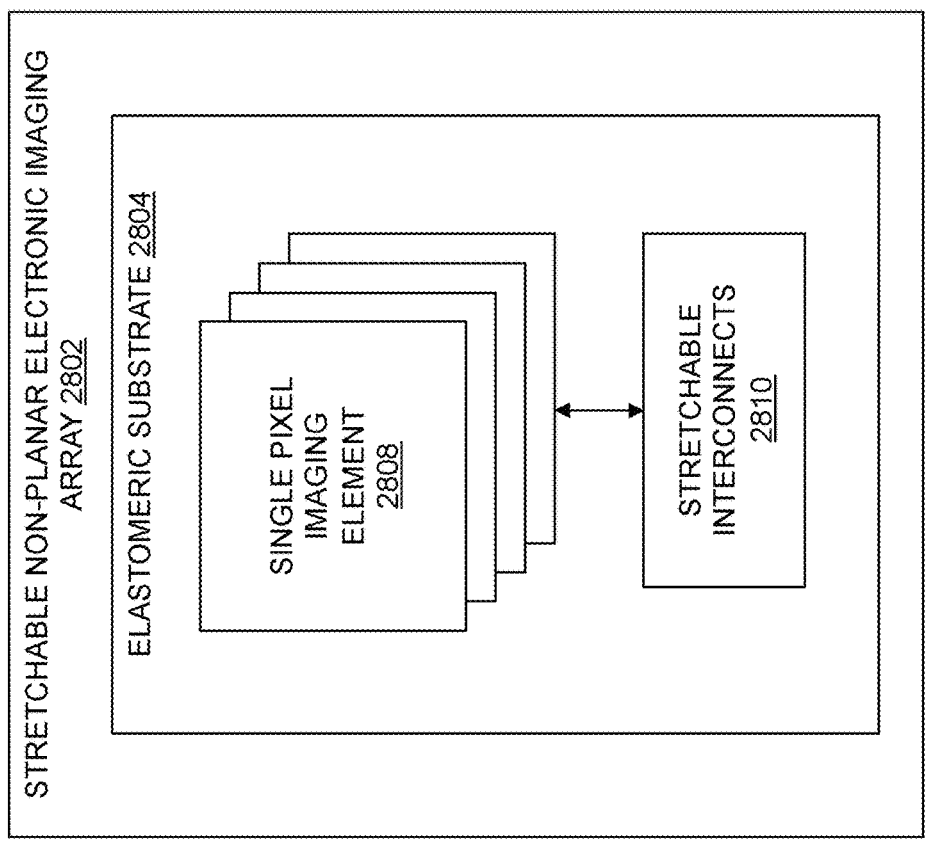
FIG. 28 depicts an embodiment for a single-pixel non-planar electronic imaging array with stretchable interconnects.

Referring to FIG. 28, in embodiments the present invention may provide for an imaging array facility, comprising a stretchable non-planar electronic imaging array 2802, where the array may be made up of a plurality of single pixel semiconductor imaging elements 2808 electrically interconnected with stretchable interconnections 2810 and mounted on an elastomeric substrate 2804. Each of the single pixel semiconductor imaging elements may include support electronics. The semiconductor may be a single-crystalline semiconductor. The semiconductor may be a non-single crystal silicon material used for photo-detection, such as an amorphous silicon material, polycrystalline silicon material, single-crystal silicon material, conductive oxide material, organic material, carbon nano-tube material, and the like. The semiconductor imaging cells may include at least one imaging pixel and support electronics for controlling and reading out the image from the at least one imaging pixel. Light may impinge the front-side of the imaging cells as provided in the non-planar electronic imaging structure. Light may impinge the back-side of the imaging cells as provided in the non-planar electronic imaging structure, where the imaging cells have at least one of color filters and micro-lenses transfer printed onto the backside of the imaging cells. The imaging structure may be actuated, such as to change the curvature of the imaging structure. A curved imaging system imager packaging may be provided, such as a chip scale packaging, a ball grid array, and the like. The fabrication of the imaging cells may be on at least one of a silicon-on-insulator (SOI) and a rigid stack, where the fabrication structure may be a layered order of Silicon, then Polymethyl Methacrylate (PMMA), then polyimide (PI), then Silicon. The imaging cells include color filters, such as to provide for color image capabilities. The imaging cells may include micro-lenses, such as to provide for enhanced image quality. The imaging cells may be arranged as sensor islands, such as comprised of one pixel per sensor island, or more than one pixel per sensor island. The imaging array may be shaped in symmetrical non-planar geometry, such as a paraboloid of revolution, a hemisphere, an ellipsoid, and the like. The imaging array structure may be used to create a camera module, such as including a lens barrel with at least one lens on a moveable mount, and a circuit for image processing and transmission. The camera module may include a lens, such as a plastic molded lens. The lens shape may be changed via the application of a force, such as a radial tension force, a radial compression force, and the like. The imaging array may be actuated, such as to change the curvature of the imaging structure.

Figure 29:
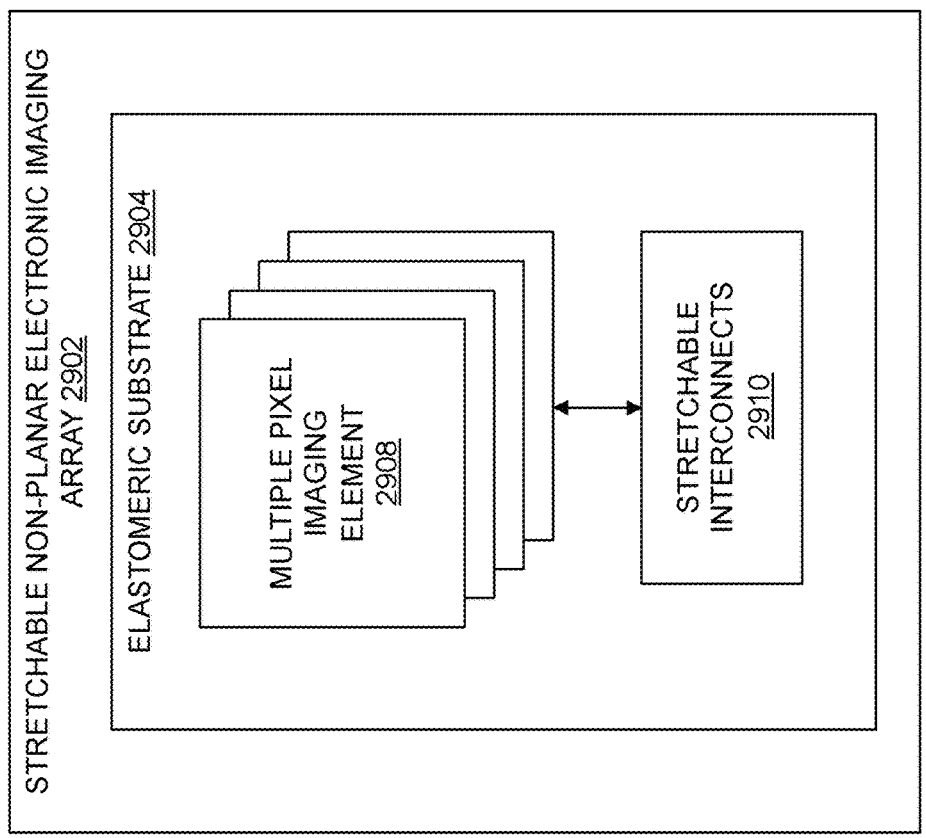
FIG. 29 depicts an embodiment for a multiple-pixel non-planar electronic imaging array with stretchable interconnects.

Referring to FIG. 29, in embodiments the present invention may provide for an imaging array facility, comprising a stretchable non-planar electronic imaging array 2902, where the array may be made up of a plurality of multiple pixel semiconductor imaging elements 2908, and where the imaging elements may be electrically interconnected with stretchable interconnections 2910 and mounted on an elastomeric substrate 2904. Each of the multiple pixel semiconductor imaging elements may include support electronics. The semiconductor may be a single-crystalline semiconductor. The semiconductor may be a non-single crystal silicon material used for photo-detection, such as an amorphous silicon material, polycrystalline silicon material, single-crystal silicon material, conductive oxide material, organic material, carbon nano-tube material, and the like. The semiconductor imaging cells may include at least one imaging pixel and support electronics for controlling and reading out the image from the at least one imaging pixel. Light may impinge the front-side of the imaging cells as provided in the non-planar electronic imaging structure. Light may impinge the back-side of the imaging cells as provided in the non-planar electronic imaging structure, where the imaging cells have at least one of color filters and micro-lenses transfer printed onto the backside of the imaging cells. The imaging structure may be actuated, such as to change the curvature of the imaging structure. A curved imaging system imager packaging may be provided, such as a chip scale packaging, a ball grid array, and the like. The fabrication of the imaging cells may be on at least one of a silicon-on-insulator (SOI) and a rigid stack, where the fabrication structure may be a layered order of Silicon, then Polymethyl Methacrylate (PMMA), then polyimide (PI), then Silicon. The imaging cells include color filters, such as to provide for color image capabilities. The imaging cells may include micro-lenses, such as to provide for enhanced image quality. The imaging cells may be arranged as sensor islands, such as comprised of one pixel per sensor island, or more than one pixel per sensor island. The imaging array may be shaped in symmetrical non-planar geometry, such as a paraboloid of revolution, a hemisphere, an ellipsoid, and the like. The imaging array structure may be used to create a camera module, such as including a lens barrel with at least one lens on a moveable mount, and a circuit for image processing and transmission. The camera module may include a lens, such as a plastic molded lens. The lens shape may be changed via the application of a force, such as a radial tension force, a radial compression force, and the like.

Figure 30:
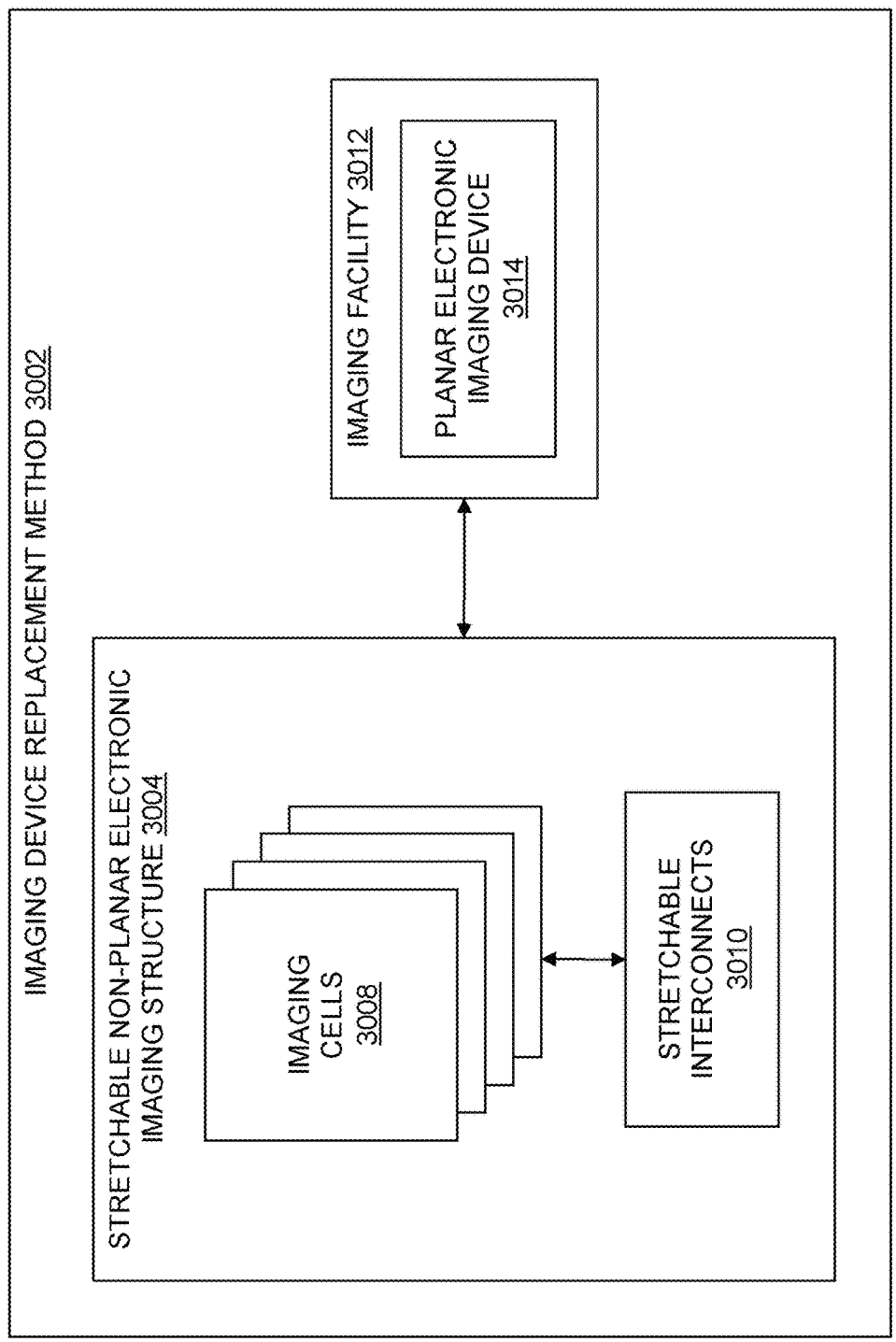
FIG. 30 depicts an embodiment for a stretchable non-planar electronic imaging device for replacement of a planar electronic imaging device.

Referring to FIG. 30, in embodiments the present invention may provide for an imaging device replacement method 3002, comprising a stretchable non-planar electronic imaging device 3004, where the structure may include semiconductor imaging cells 3008 electrically interconnected with stretchable interconnections 3010, and replacing a planar electronic imaging device 3014 in an imaging facility 3012 to improve the imaging performance of the imaging facility. The replacement may be an integrated replacement with the imaging facility, an imaging sensor within the imaging facility, and the like. The semiconductor may be a single-crystalline semiconductor. The semiconductor may be a non-single crystal silicon material used for photo-detection, such as an amorphous silicon material, polycrystalline silicon material, single-crystal silicon material, conductive oxide material, organic material, carbon nano-tube material, and the like. The semiconductor imaging cells may include at least one imaging pixel and support electronics for controlling and reading out the image from the at least one imaging pixel. Light may impinge the front-side of the imaging cells as provided in the non-planar electronic imaging structure. Light may impinge the back-side of the imaging cells as provided in the non-planar electronic imaging structure, where the imaging cells have at least one of color filters and micro-lenses transfer printed onto the backside of the imaging cells. The imaging structure may be actuated, such as to change the curvature of the imaging structure. A curved imaging system imager packaging may be provided, such as a chip scale packaging, a ball grid array, and the like. The fabrication of the imaging cells may be on at least one of a silicon-on-insulator (SOI) and a rigid stack, where the fabrication structure may be a layered order of Silicon, then Polymethyl Methacrylate (PMMA), then polyimide (PI), then Silicon. The imaging cells include color filters, such as to provide for color image capabilities. The imaging cells may include micro-lenses, such as to provide for enhanced image quality. The imaging cells may be arranged as sensor islands, such as comprised of one pixel per sensor island, or more than one pixel per sensor island. The imaging array may be shaped in symmetrical non-planar geometry, such as a paraboloid of revolution, a hemisphere, an ellipsoid, and the like. The imaging array structure may be used to create a camera module, such as including a lens barrel with at least one lens on a moveable mount, and a circuit for image processing and transmission. The camera module may include a lens, such as a plastic molded lens. The lens shape may be changed via the application of a force, such as a radial tension force, a radial compression force, and the like. The imaging array may be actuated, such as to change the curvature of the imaging structure.

Figure 31:
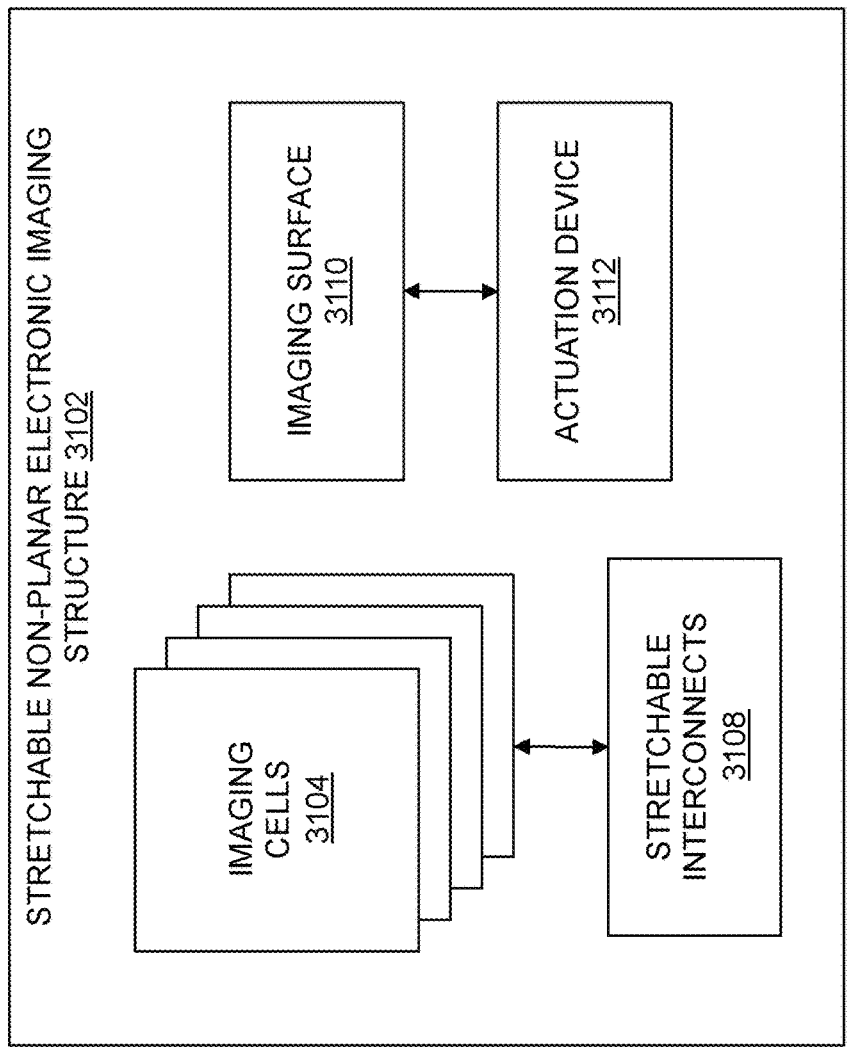
FIG. 31 depicts an embodiment for a stretchable non-planar electronic imaging structure whose surface is altered by mechanical actuation.

Referring to FIG. 31, in embodiments the present invention may provide for an imaging facility, comprising a stretchable non-planar electronic imaging structure 3102, where the structure may include semiconductor imaging cells 3104 electrically interconnected with stretchable interconnections 3108, and at least one mechanical actuation device 3112 attached to the imaging structure, where the actuation device may be capable of changing the shape of an imaging surface 3110 of the imaging structure. The semiconductor may be a single-crystalline semiconductor. The semiconductor may be a non-single crystal silicon material used for photo-detection, such as an amorphous silicon material, polycrystalline silicon material, single-crystal silicon material, conductive oxide material, organic material, carbon nano-tube material, and the like. The semiconductor imaging cells may include at least one imaging pixel and support electronics for controlling and reading out the image from the at least one imaging pixel. Light may impinge the front-side of the imaging cells as provided in the non-planar electronic imaging structure. Light may impinge the back-side of the imaging cells as provided in the non-planar electronic imaging structure, where the imaging cells have at least one of color filters and micro-lenses transfer printed onto the backside of the imaging cells. The imaging structure may be actuated, such as to change the curvature of the imaging structure. A curved imaging system imager packaging may be provided, such as a chip scale packaging, a ball grid array, and the like. The fabrication of the imaging cells may be on at least one of a silicon-on-insulator (SOI) and a rigid stack, where the fabrication structure may be a layered order of Silicon, then Polymethyl Methacrylate (PMMA), then polyimide (PI), then Silicon. The imaging cells include color filters, such as to provide for color image capabilities. The imaging cells may include micro-lenses, such as to provide for enhanced image quality. The imaging cells may be arranged as sensor islands, such as comprised of one pixel per sensor island, or more than one pixel per sensor island. The imaging array may be shaped in symmetrical non-planar geometry, such as a paraboloid of revolution, a hemisphere, an ellipsoid, and the like. The imaging array structure may be used to create a camera module, such as including a lens barrel with at least one lens on a moveable mount, and a circuit for image processing and transmission. The camera module may include a lens, such as a plastic molded lens. The lens shape may be changed via the application of a force, such as a radial tension force, a radial compression force, and the like. The imaging array may be actuated, such as to change the curvature of the imaging structure.

Figure 32:
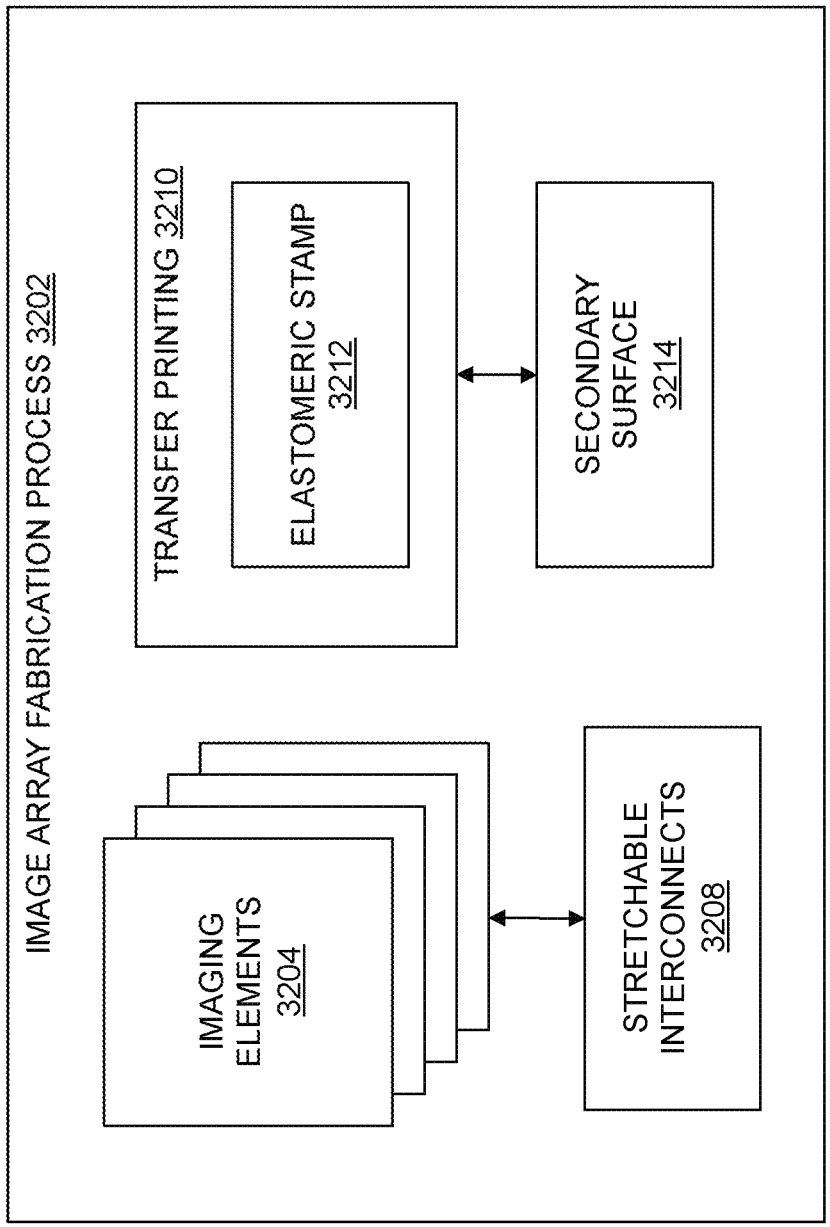
FIG. 32 depicts an embodiment for a stretchable non-planar electronic imaging device fabrication process using transfer printing.

Referring to FIG. 32, in embodiments the present invention may provide for an imaging array fabrication process 3202 method, comprising fabricating an array of semiconductor imaging elements 3204, interconnecting the elements with stretchable interconnections 3208, and transfer printing 3210 the array with a pre-strained elastomeric stamp 3212 to a secondary non-planar surface 3214. The semiconductor may be a single-crystalline semiconductor. The semiconductor may be a non-single crystal silicon material used for photo-detection, such as an amorphous silicon material, polycrystalline silicon material, single-crystal silicon material, conductive oxide material, organic material, carbon nano-tube material, and the like. The semiconductor imaging cells may include at least one imaging pixel and support electronics for controlling and reading out the image from the at least one imaging pixel. Light may impinge the front-side of the imaging cells as provided in the non-planar electronic imaging structure. Light may impinge the back-side of the imaging cells as provided in the non-planar electronic imaging structure, where the imaging cells have at least one of color filters and micro-lenses transfer printed onto the backside of the imaging cells. The imaging structure may be actuated, such as to change the curvature of the imaging structure. A curved imaging system imager packaging may be provided, such as a chip scale packaging, a ball grid array, and the like. The fabrication of the imaging cells may be on at least one of a silicon-on-insulator (SOI) and a rigid stack, where the fabrication structure may be a layered order of Silicon, then Polymethyl Methacrylate (PMMA), then polyimide (PI), then Silicon. The imaging cells include color filters, such as to provide for color image capabilities. The imaging cells may include micro-lenses, such as to provide for enhanced image quality. The imaging cells may be arranged as sensor islands, such as comprised of one pixel per sensor island, or more than one pixel per sensor island. The imaging array may be shaped in symmetrical non-planar geometry, such as a paraboloid of revolution, a hemisphere, an ellipsoid, and the like. The imaging array structure may be used to create a camera module, such as including a lens barrel with at least one lens on a moveable mount, and a circuit for image processing and transmission. The camera module may include a lens, such as a plastic molded lens. The lens shape may be changed via the application of a force, such as a radial tension force, a radial compression force, and the like. The imaging array may be actuated, such as to change the curvature of the imaging structure.

Figure 33:
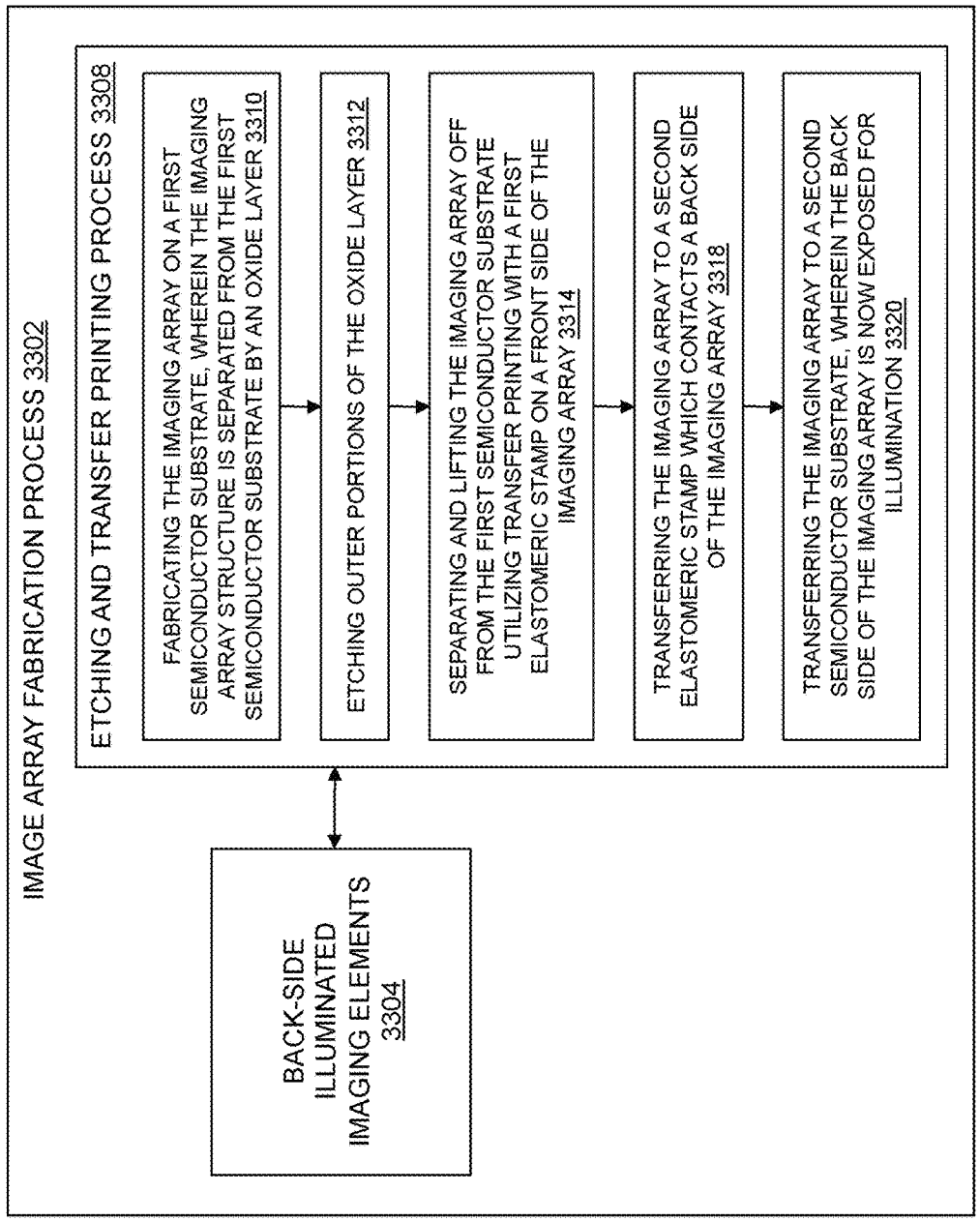
FIG. 33 depicts an embodiment for a planar electronic back-side illumination imaging device fabrication process using transfer printing.

Referring to FIG. 33, in embodiments the present invention may provide for an imaging array fabrication process 3302 method, comprising fabricating an imaging array of semiconductor back side illumination imaging elements 3304, where the fabrication of the imaging array may includes etching and transfer printing 3308 steps: (1) a first step 3310 fabricating the imaging array on a first semiconductor substrate, where the imaging array structure is separated from the first semiconductor substrate by an oxide layer, (2) a second step 3312 etching outer portions of the oxide layer, (3) a third step 3314 separating and lifting the imaging array off from the first semiconductor substrate utilizing transfer printing with a first elastomeric stamp on a front side of the imaging array, (4) a forth step 3318 transferring the imaging array to a second elastomeric stamp which contacts a back side of the imaging array; and (5) a fifth step 3320 transferring the imaging array to a second semiconductor substrate, where the back side of the imaging array is now exposed for illumination. In embodiments, a lens may be attached to at least one of the back side illumination imaging elements, such as a micro-lens. A filter may be attached to at least one of the back side illumination imaging elements, such as a color filter. The semiconductor may be a single-crystalline semiconductor. The semiconductor may be a non-single crystal silicon material used for photo-detection, such as an amorphous silicon material, polycrystalline silicon material, single-crystal silicon material, conductive oxide material, organic material, carbon nano-tube material, and the like. The semiconductor imaging cells may include at least one imaging pixel and support electronics for controlling and reading out the image from the at least one imaging pixel. Light may impinge the front-side of the imaging cells as provided in the non-planar electronic imaging structure. Light may impinge the back-side of the imaging cells as provided in the non-planar electronic imaging structure, where the imaging cells have at least one of color filters and micro-lenses transfer printed onto the backside of the imaging cells. The imaging structure may be actuated, such as to change the curvature of the imaging structure. A curved imaging system imager packaging may be provided, such as a chip scale packaging, a ball grid array, and the like. The fabrication of the imaging cells may be on at least one of a silicon-on-insulator (SOI)

and a rigid stack, where the fabrication structure may be a layered order of Silicon, then Polymethyl Methacrylate (PMMA), then polyimide (PI), then Silicon. The imaging cells include color filters, such as to provide for color image capabilities. The imaging cells may include micro-lenses, such as to provide for enhanced image quality. The imaging cells may be arranged as sensor islands, such as comprised of one pixel per sensor island, or more than one pixel per sensor island. The imaging array may be shaped in symmetrical non-planar geometry, such as a paraboloid of revolution, a hemisphere, an ellipsoid, and the like. The imaging array structure may be used to create a camera module, such as including a lens barrel with at least one lens on a moveable mount, and a circuit for image processing and transmission. The camera module may include a lens, such as a plastic molded lens. The lens shape may be changed via the application of a force, such as a radial tension force, a radial compression force, and the like. The imaging array may be actuated, such as to change the curvature of the imaging structure.

Certain of the methods and systems described in connection with the invention described (hereinafter referred to as the "Subject Methods and Systems") may be deployed in part or in whole through a machine that executes computer software, program codes, and/or instructions on a processor integrated with or separate from the electronic circuitry described herein. Said certain methods and systems will be apparent to those skilled in the art, and nothing below is meant to limit that which has already been disclosed but rather to supplement it.

The active stretchable or flexible circuitry described herein may be considered the machine necessary to deploy the Subject Methods and System in full or in part, or a separately located machine may deploy the Subject Methods and Systems in whole or in part. Thus, "machine" as referred to herein may be applied to the circuitry described above, a separate processor, separate interface electronics or combinations thereof.

The Subject Methods and Systems invention may be implemented as a method on the machine, as a system or apparatus as part of or in relation to the machine, or as a computer program product embodied in a computer readable medium executing on one or more of the machines. In embodiments, the processor may be part of a server, client, network infrastructure, mobile computing platform, stationary computing platform, or other computing platform. A processor may be any kind of computational or processing device capable of executing program instructions, codes, binary instructions and the like. The processor may be or include a signal processor, digital processor, embedded processor, microprocessor or any variant such as a co-processor (math co-processor, graphic co-processor, communication co-processor and the like) and the like that may directly or indirectly facilitate execution of program code or program instructions stored thereon. In addition, the processor may enable execution of multiple programs, threads, and codes. The threads may be executed simultaneously to enhance the performance of the processor and to facilitate simultaneous operations of the application. By way of implementation, methods, program codes, program instructions and the like described herein may be implemented in one or more thread. The thread may spawn other threads that may have assigned priorities associated with them; the processor may execute these threads based on priority or any other order based on instructions provided in the program code. The processor, or any machine utilizing one, may include memory that stores methods, codes, instructions and programs as described herein and elsewhere. The processor may access a storage medium through an interface that may store methods, codes, and instructions as described herein and elsewhere. The storage medium associated with the processor for storing methods, programs, codes, program instructions or other type of instructions capable of being executed by the computing or processing device may include but may not be limited to one or more of a CD-ROM, DVD, memory, hard disk, flash drive, RAM, ROM, cache and the like. Nothing in this paragraph or the paragraphs below is meant to limit or contradict the description of the processing facility described herein and throughout.

A processor may include one or more cores that may enhance speed and performance of a multiprocessor. In embodiments, the process may be a dual core processor, quad core processors, other chip-level multiprocessor and the like that combine two or more independent cores (called a die).

The Subject Methods and Systems described herein may be deployed in part or in whole through a machine that executes computer software on a server, client, firewall, gateway, hub, router, or other such computer and/or networking hardware. The software program may be associated with a server that may include a file server, print server, domain server, internet server, intranet server and other variants such as secondary server, host server, distributed server and the like. The server may include one or more of memories, processors, computer readable media, storage media, ports (physical and virtual), communication devices, and interfaces capable of accessing other servers, clients, machines, and devices through a wired or a wireless medium, and the like. The methods, programs or codes as described herein and elsewhere may be executed by the server. In addition, other devices required for execution of methods as described in this application may be considered as a part of the infrastructure associated with the server.

The server may provide an interface to other devices including, without limitation, clients, other servers, printers, database servers, print servers, file servers, communication servers, distributed servers and the like. Additionally, this coupling and/or connection may facilitate remote execution of program across the network. The networking of some or all of these devices may facilitate parallel processing of a program or method at one or more location without deviating from the scope of the invention. In addition, any of the devices attached to the server through an interface may include at least one storage medium capable of storing methods, programs, code and/or instructions. A central repository may provide program instructions to be executed on different devices. In this implementation, the remote repository may act as a storage medium for program code, instructions, and programs.

If the Subject Methods and Systems are embodied in a software program, the software program may be associated with a client that may include a file client, print client, domain client, internet client, intranet client and other variants such as secondary client, host client, distributed client and the like. The client may include one or more of memories, processors, computer readable media, storage media, ports (physical and virtual), communication devices, and interfaces capable of accessing other clients, servers, machines, and devices through a wired or a wireless medium, and the like. The methods, programs or codes as described herein and elsewhere may be executed by the client. In addition, other devices required for execution of methods as described in this application may be considered as a part of the infrastructure associated with the client.

The client may provide an interface to other devices including, without limitation, servers, other clients, printers, database servers, print servers, file servers, communication servers, distributed servers and the like. Additionally, this coupling and/or connection may facilitate remote execution of program across the network. The networking of some or all of these devices may facilitate parallel processing of a program or method at one or more location without deviating from the scope of the invention. In addition, any of the devices attached to the client through an interface may include at least one storage medium capable of storing methods, programs, applications, code and/or instructions. A central repository may provide program instructions to be executed on different devices. In this implementation, the remote repository may act as a storage medium for program code, instructions, and programs.

The Subject Methods and Systems described herein may be deployed in part or in whole through network infrastructures. The network infrastructure may include elements such as computing devices, servers, routers, hubs, firewalls, clients, personal computers, communication devices, routing devices and other active and passive devices, modules and/or components as known in the art. The computing and/or non-computing device(s) associated with the network infrastructure may include, apart from other components, a storage medium such as flash memory, buffer, stack, RAM, ROM and the like. The processes, methods, program codes, instructions described herein and elsewhere may be executed by one or more of the network infrastructural elements.

The methods, program codes, and instructions pertaining to the Subject Methods and Systems described herein and elsewhere may be implemented on a cellular network having multiple cells. The cellular network may either be frequency division multiple access (FDMA) network or code division multiple access (CDMA) network. The cellular network may include mobile devices, cell sites, base stations, repeaters, antennas, towers, and the like. The cell network may be a GSM, GPRS, 3G, EVDO, mesh, or other networks types.

The methods, program codes, and instructions pertaining to the Subject Methods and Systems described herein and elsewhere may be implemented on or through mobile devices. The mobile devices may include navigation devices, cell phones, mobile phones, mobile personal digital assistants, laptops, palmtops, netbooks, pagers, electronic books readers, music players and the like. These devices may include, apart from other components, a storage medium such as a flash memory, buffer, RAM, ROM and one or more computing devices. The computing devices associated with mobile devices may be enabled to execute program codes, methods, and instructions stored thereon. Alternatively, the mobile devices may be configured to execute instructions in collaboration with other devices. The mobile devices may communicate with base stations interfaced with servers and configured to execute program codes. The mobile devices may communicate on a peer to peer network, mesh network, or other communications network. The program code may be stored on the storage medium associated with the server and executed by a computing device embedded within the server. The base station may include a computing device and a storage medium. The storage device may store program codes and instructions executed by the computing devices associated with the base station.

The computer software, program codes, and/or instructions pertaining to the Subject Methods and Systems may be stored and/or accessed on machine readable media that may include: computer components, devices, and recording media that retain digital data used for computing for some interval of time; semiconductor storage known as random access memory (RAM); mass storage typically for more permanent storage, such as optical discs, forms of magnetic storage like hard disks, tapes, drums, cards and other types; processor registers, cache memory, volatile memory, non-volatile memory; optical storage such as CD, DVD; removable media such as flash memory (e.g. USB sticks or keys), floppy disks, magnetic tape, paper tape, punch cards, stand-alone RAM disks, Zip drives, removable mass storage, off-line, and the like; other computer memory such as dynamic memory, static memory, read/write storage, mutable storage, read only, random access, sequential access, location addressable, file addressable, content addressable, network attached storage, storage area network, bar codes, magnetic ink, and the like.

The Subject Methods and Systems described herein may transform physical and/or or intangible items from one state to another. The methods and systems described herein may also transform data representing physical and/or intangible items from one state to another.

The elements described and depicted herein and the functions thereof may be implemented on machines through computer executable media having a processor capable of executing program instructions stored thereon as a monolithic software structure, as standalone software modules, or as modules that employ external routines, code, services, and so forth, or any combination of these, and all such implementations may be within the scope of the present disclosure. Examples of such machines may include, but may not be limited to, personal digital assistants, laptops, personal computers, mobile phones, other handheld computing devices, medical equipment, wired or wireless communication devices, transducers, chips, calculators, satellites, tablet PCs, electronic books, gadgets, electronic devices, devices having artificial intelligence, computing devices, networking equipments, servers, routers and the like. Furthermore, the elements depicted in the flow chart and block diagrams or any other logical component may be implemented on a machine capable of executing program instructions. Thus, while the foregoing descriptions set forth functional aspects of the disclosed systems, no particular arrangement of software for implementing these functional aspects should be inferred from these descriptions unless explicitly stated or otherwise clear from the context. Similarly, it will be appreciated that the various steps identified and described above may be varied, and that the order of steps may be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

The Subject Methods and Systems, and steps associated therewith, may be realized in hardware, software or any combination of hardware and software suitable for a particular application. The hardware may include a general purpose computer and/or dedicated computing device or specific computing device or particular aspect or component of a specific computing device. The processes may be realized in one or more microprocessors, microcontrollers, embedded microcontrollers, programmable digital signal processors or other programmable device, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as a computer executable code capable of being executed on a machine readable medium.

The computer executable code may be created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software, or any other machine capable of executing program instructions.

Thus, in one aspect, methods described above in connection with the Subject Systems and Methods and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. In another aspect, the means for performing the steps associated with the processes described above may include any of the hardware and/or software described above. All such permutations and combinations are intended to fall within the scope of the present disclosure.

While the invention has been described in connection with certain preferred embodiments, other embodiments would be understood by one of ordinary skill in the art and are encompassed herein.

All documents referenced herein are hereby incorporated by reference.

What is claimed is:

1. A flexible imaging sensor to sense an area of tissue, the sensor comprising:
   at least one imaging element including a semiconductor based photo detector;
   a processor in electrical communication to the at least one imaging element to capture an image of the area of tissue; and
   at least one stretchable interconnect, the at least one stretchable interconnect coupling the at least one imaging element to the processor.

2. The flexible imaging sensor of claim 1, wherein the at least one imaging element is one of a plurality of imaging elements arranged in an array, the array being flexible to adhere to the area of tissue.

3. The flexible imaging array of claim 2, wherein each imaging element includes a pn junction blocking diode, an active amplifier, and an analog to digital converter each coupled to the photo detector.

4. The flexible imaging array of claim 1, wherein the at least one imaging element is formed on a crystalline silicon substrate.

5. The flexible imaging array of claim 1, wherein the at least one imaging element is encapsulated with a polymer layer.

6. The flexible imaging array of claim 2, wherein each imaging element is an active pixel sensor.

7. The flexible imaging array of claim 1, further comprising a light source to provide illumination to the at least one imaging element for illuminating the tissue of interest.

8. The flexible imaging array of claim 7, wherein the light source is an optical fiber or a light emitting diode (LED).

9. The flexible imaging array of claim 1, wherein the at least one imaging element includes a micro lens disposed over the photo detector.

10. The flexible imaging array of claim 1, wherein the processor determines blood flow from the sensed optical characteristic of the tissue.

11. The flexible imaging array of claim 1, wherein the processor determines a pulse or a photoplethysmography (PPG) based on the sensed optical characteristic of the tissue.

12. A blood flow sensor for attachment to an area of tissue, the sensor comprising:
    a photo detector based pixel sensor operable for sensing the area of tissue when the area of tissue is in sufficient proximity to the photo detector;
    a processor coupled to the pixel sensor to sense the blood flow through the area of tissue based on changes in the optical signal from the area of tissue detected by the pixel sensor; and
    at least one stretchable interconnect, the at least one stretchable interconnect coupling the pixel sensor to the processor.

13. The flexible imaging sensor of claim 12, wherein the pixel sensor is one of a plurality of pixel sensors arranged in an array, the array being flexible to adhere to the area of tissue.

14. A blood pressure sensor for attachment to an area of tissue, the sensor comprising:
    a photo detector based pixel sensor operable for sensing the area of tissue when the area of tissue is in sufficient proximity to the pixel sensor;
    a processor coupled to the pixel sensor to sense blood pressure or photoplethysmography (PPG) based on changes in the optical signals from the area of tissue detected by the pixel sensor; and
    at least one stretchable interconnect, the at least one stretchable interconnect coupling the pixel sensor to the processor.

15. The blood pressure sensor of claim 14, wherein the pixel sensor is one of a plurality of pixel sensors arranged in an array, the array being flexible to adhere to the area of tissue.

* * * * *